US012773050B2

(12) United States Patent
Karschnik et al.

(10) Patent No.: US 12,773,050 B2
(45) Date of Patent: Oct. 27, 2026

(54) MATTRESS ADJUSTMENT BASED ON USER SLEEP STATES

(71) Applicant: SNBR INC., Minneapolis, MN (US)

(72) Inventors: Kody Lee Karschnik, Plymouth, MN (US); Gary N. Garcia Molina, Madison, WI (US)

(73) Assignee: SNBR INC., Minneapolis, MN (US)

(*) Notice: Subject to any disclaimer, the term of this patent is extended or adjusted under 35 U.S.C. 154(b) by 1113 days.

(21) Appl. No.: 17/729,312

(22) Filed: Apr. 26, 2022

(65) Prior Publication Data

US 2022/0346565 A1 Nov. 3, 2022

Related U.S. Application Data

(60) Provisional application No. 63/181,590, filed on Apr. 29, 2021.

(51) Int. Cl.
*A47C 27/08* (2006.01)
*A47C 27/10* (2006.01)
(Continued)

(52) U.S. Cl.
CPC .......... *A47C 27/083* (2013.01); *A47C 27/082* (2013.01); *A47C 31/123* (2013.01);
(Continued)

(58) Field of Classification Search
CPC ...... A61M 2021/0027; A61M 21/0094; A61M 2021/0022; A61M 2021/0044;
(Continued)

(56) References Cited

U.S. PATENT DOCUMENTS 5,136,740 A 8/1992 Kraft
7,103,933 B2 9/2006 Gladney et al.
(Continued)

FOREIGN PATENT DOCUMENTS

CN 108420228 8/2018
CN 112236180 1/2021

OTHER PUBLICATIONS

International Preliminary Report on Patentability in International Appln. No. PCT/US2022/026303, mailed on Nov. 9, 2023, 8 pages.
(Continued)

*Primary Examiner* — Sunita Reddy
(74) *Attorney, Agent, or Firm* — Norton Rose Fulbright US LLP

(57) ABSTRACT

A bed has a mattress. A sensor system is configured to sense at least one physical phenomenon through a sleep session. A controller may include at least one processor and memory, the controller configured to receive, through the sleep session, the sensor data; select, from a plurality of optional algorithms, a selected algorithm based on at least one of the sensor data, user input, and checking a clock, where the optional algorithms include (i) a state-based algorithm and (ii) a schedule-based algorithm; update, through the sleep session, using the selected algorithm, a current sleep state of the sleeper; track the sleep session based on the update of the current sleep state of the sleeper through the sleep session; update, through the sleep session, using the tracking of the sleep session, a target environmental-parameter; and send, through the sleep session, automation instructions to an environmental controller.

18 Claims, 26 Drawing Sheets

(51) Int. Cl.
*A47C 31/12* (2006.01)
*A61B 5/00* (2006.01)

(52) U.S. Cl.
CPC .......... *A61B 5/4812* (2013.01); *A61B 5/6892* (2013.01); *A47C 27/10* (2013.01)

(58) Field of Classification Search
CPC .. A61M 2021/0066; A61M 2021/0083; A61M 2202/0233; A61M 2205/07; A61M 2205/18; A61M 2205/3306; A61M 2205/332; A61M 2205/3331; A61M 2205/3368; A61M 2205/3375; A61M 2205/3553; A61M 2205/3584; A61M 21/00; A61M 21/02; A61M 2021/005; A61M 2205/3592; A61M 2205/3606; A61M 2205/362; A61M 2205/505; A61M 2205/52; A61M 2205/587; A61M 2205/609; A61M 2205/8206; A61M 2205/8212; A61M 2209/01; A61M 2209/088; A61M 2230/06; A61M 2230/30; A61M 2230/40; A61M 2230/42; A61M 2230/04; A61M 2230/50; A61M 2230/62; A61M 2230/63; A61M 2230/005
USPC ........................................................ 600/26–28
See application file for complete search history.

(56) References Cited

U.S. PATENT DOCUMENTS 7,513,003 B2 4/2009 Mossbeck
8,444,558 B2 5/2013 Young et al.
8,672,853 B2 3/2014 Young
8,984,687 B2 3/2015 Stusynski et al.
9,005,101 B1 * 4/2015 Van Erlach .......... A47C 31/123 600/9
9,370,457 B2 6/2016 Nunn et al.
9,392,879 B2 7/2016 Nunn et al.
9,445,751 B2 9/2016 Young et al.
9,504,416 B2 11/2016 Young et al.
9,510,688 B2 12/2016 Nunn et al.
9,635,953 B2 5/2017 Nunn et al.
9,770,114 B2 9/2017 Brosnan et al.
9,844,275 B2 12/2017 Nunn et al.
9,931,085 B2 4/2018 Young et al.
10,058,467 B2 8/2018 Stusynski et al.
10,092,242 B2 10/2018 Nunn et al.
10,149,549 B2 12/2018 Erko et al.
10,182,661 B2 1/2019 Nunn et al.
10,201,234 B2 2/2019 Nunn et al.
10,251,490 B2 4/2019 Nunn et al.
10,314,407 B1 6/2019 Main et al.
10,342,358 B1 7/2019 Palashewski et al.
10,441,086 B2 10/2019 Nunn et al.
10,441,087 B2 10/2019 Karschnik et al.
10,448,749 B2 10/2019 Palashewski et al.
10,492,969 B2 12/2019 Stusynski et al.
10,632,032 B1 4/2020 Stusynski et al.
10,646,050 B2 5/2020 Nunn et al.
10,674,832 B2 6/2020 Brosnan et al.
10,716,512 B2 7/2020 Erko et al.
10,729,255 B2 8/2020 Erko et al.
10,736,432 B2 8/2020 Brosnan et al.
10,750,875 B2 8/2020 Palashewski et al.
10,827,846 B2 11/2020 Karschnik et al.
10,881,219 B2 1/2021 Nunn et al.
10,957,335 B2 3/2021 Demirli et al.
10,959,535 B2 3/2021 Karschnik et al.
D916,745 S 4/2021 Stusynski et al.
10,980,351 B2 4/2021 Nunn et al.
11,096,849 B2 8/2021 Stusynski et al.
11,122,909 B2 9/2021 Palashewski et al.
11,160,683 B2 11/2021 Nunn et al.
11,206,929 B2 12/2021 Palashewski et al.
11,253,079 B1 * 2/2022 Kahn .................. A47C 27/083
D954,725 S 6/2022 Stusynski et al.
2008/0077020 A1 3/2008 Young et al.
2008/0093784 A1 4/2008 Rawls-Meehan
2010/0170043 A1 7/2010 Young et al.
2011/0010014 A1 * 1/2011 Oexman .................. F24F 11/63 600/301
2011/0144455 A1 6/2011 Young et al.
2012/0296156 A1 * 11/2012 Auphan ................ A61M 21/02 600/26
2013/0234823 A1 * 9/2013 Kahn ................ G06Q 10/1093 340/3.1
2014/0277822 A1 9/2014 Nunn et al.
2016/0015184 A1 1/2016 Nunn et al.
2016/0100696 A1 * 4/2016 Palashewski ........ A61B 5/4809 5/706
2016/0242562 A1 * 8/2016 Karschnik ............ A47C 27/082
2016/0367039 A1 12/2016 Young et al.
2017/0065220 A1 3/2017 Young et al.
2017/0128001 A1 5/2017 Torre et al.
2017/0143269 A1 5/2017 Young et al.
2018/0125256 A1 * 5/2018 Tsemn ................ A47C 27/083
2019/0053761 A1 2/2019 Torre et al.
2019/0069840 A1 3/2019 Young et al.
2019/0200777 A1 7/2019 Demirli et al.
2019/0201265 A1 7/2019 Sayadi et al.
2019/0201266 A1 7/2019 Sayadi et al.
2019/0201267 A1 7/2019 Demirli et al.
2019/0201268 A1 7/2019 Sayadi et al.
2019/0201269 A1 * 7/2019 Sayadi ................ A61B 5/4809
2019/0201270 A1 7/2019 Sayadi et al.
2019/0201271 A1 7/2019 Grey et al.
2019/0328146 A1 10/2019 Palashewski et al.
2019/0328147 A1 10/2019 Palashewski et al.
2019/0336720 A1 11/2019 Tsern et al.
2020/0100682 A1 * 4/2020 Abreu ................ A61B 5/6803
2020/0205580 A1 7/2020 Sayadi et al.
2020/0315367 A1 10/2020 Demirli et al.
2020/0336010 A1 10/2020 Holmvik et al.
2020/0359807 A1 11/2020 Brosnan et al.
2020/0367663 A1 11/2020 Nunn et al.
2020/0405070 A1 12/2020 Palashewski et al.
2020/0405240 A1 12/2020 Palashewski et al.
2021/0000261 A1 1/2021 Erko et al.
2021/0034989 A1 2/2021 Palashewski et al.
2021/0045541 A1 2/2021 Nunn et al.
2021/0068552 A1 3/2021 Palashewski et al.
2021/0112992 A1 4/2021 Nunn et al.
2021/0267380 A1 9/2021 Stusynski
2021/0282570 A1 9/2021 Karschnik et al.
2021/0289947 A1 9/2021 Karschnik et al.
2021/0314405 A1 10/2021 Demirli et al.
2021/0346218 A1 11/2021 Stusynski et al.
2022/0000273 A1 1/2022 Palashewski et al.
2022/0000654 A1 1/2022 Nunn et al.

OTHER PUBLICATIONS

U.S. Appl. No. 16/719,177, filed Dec. 18, 2019, Nunn et al.
U.S. Appl. No. 17/523,349, filed Nov. 10, 2021, Dixon et al.
U.S. Appl. No. 17/561,150, filed Dec. 23, 2021, Palashewski et al.
U.S. Appl. No. 17/704,537, filed Mar. 25, 2022, Stusynski et al.
U.S. Appl. No. 17/738,818, filed May 6, 2022, Molina et al.
U.S. Appl. No. 17/741,023, filed May 10, 2022, Palashewski et al.
U.S. Appl. No. 17/745,508, filed May 16, 2022, Nunn et al.
U.S. Appl. No. 17/834,493, filed Jun. 7, 2022, Molina et al.
U.S. Appl. No. 17/835,444, filed Jun. 8, 2022, Siyahjani et al.
U.S. Appl. No. 29/676,117, filed Jan. 8, 2019, Stusynski et al.
U.S. Appl. No. 29/777,084, filed Apr. 2, 2021, Stusynski et al.
U.S. Appl. No. 29/814,835, filed Nov. 9, 2021, Dixon et al.
U.S. Appl. No. 29/837,293, filed May 4, 2022, Stusynski et al.
Bader et al., "The influence of bed firmness on sleep quality," Applied Ergonomics, Oct. 2000, 31(5): 487-497.
Garcia-Molina et al., "Probabilistic characterization of sleep architecture: Home Based study on healthy volunteers," 2016 38th

(56) References Cited

OTHER PUBLICATIONS

Annual International Conference of the IEEE Engineering in Medicine and Biology Society (EMBC), Aug. 2016, 2834-2838.
Lee et al., "Quantitative effects of mattress types (comfortable vs. uncomfortable) on sleep quality through polysomnography and skin temperature," International Journal of Industrial Ergonomics, Nov. 2006, 36(11): 943-949.
International Search Report and Written Opinion in International Appln. No. PCT/US2022/026303, mailed on Aug. 1, 2022, 13 pages.

* cited by examiner

410c

Hypnogram 2400

Time Dependent Sleep Stage Probability 2500

MATTRESS ADJUSTMENT BASED ON USER SLEEP STATES

CROSS-REFERENCE TO RELATED APPLICATIONS

This application claims the benefit of U.S. Provisional Application Ser. No. 63/181,590, filed Apr. 29, 2021. The disclosure of the prior application is considered part of (and is incorporated by reference in) the disclosure of this application The present document relates to systems, methods, and techniques for adjusting mattress settings based on sleep states of a mattress user.

BACKGROUND

In general, a bed is a piece of furniture used as a location to sleep or relax. Many modern beds include a soft mattress on a bed frame. The mattress may include springs, foam material, and/or an air chamber to support the weight of one or more users. Some mattresses can be firm. Some mattresses can be less firm. Some mattresses can have adjustable firmness settings. Mattress firmness can play a role in a user's sleep quality and overall sleep comfort. Mattress firmness can also feel different to users based on the users' muscle tone. The users' muscle tone can change throughout a sleep session, based on the current sleep states of the users. Sometimes, soft mattresses (e.g., low firmness) can provide a user with some comfort but may not provide enough support for proper spine alignment during different sleep states of the user.

SUMMARY

The present document generally relates to adjusting mattress firmness based on sleep states (e.g., sleep stages such as NREM or REM) of a user (e.g., sleeper). More particularly, this disclosure describes dynamically adjusting mattress firmness based on identifying a current sleep state of the user in order to optimize sleep quality and comfort. Mattress firmness can feel different to the user based on the user's muscle tone. Moreover, the user's muscle tone can change throughout a sleep session based on a current sleep stage of the user. For example, the user's muscle tone can be substantially reduced during REM sleep. When the user's muscle tone is absent, the user may not have proper spinal alignment on a softer, less firm mattress. Therefore, the disclosed technology can provide for automatically increasing the mattress firmness to accommodate for the user's lack of muscle tone during REM sleep. By increasing the mattress firmness during REM sleep, the user's sleep quality and comfort can be optimized.

As another example, during some sleep states and/or at the beginning of sleep onset, the user's muscle tone may be present. Therefore, the disclosed technology can provide for automatically decreasing the mattress firmness from a previously increased mattress firmness setting. The mattress firmness adjustments can thus include setting lower pressure settings for the mattress during early sleep onset and increasing firmness of the mattress by increasing the pressure settings for the mattress during other sleep states (e.g., NREM sleep stages). In some implementations, the disclosed technology can also provide for maintaining the mattress firmness at a user-defined or user-preferred firmness setting. In yet other implementations, the disclosed technology can provide for resetting the mattress firmness to the user-defined or user-preferred firmness setting.

The disclosed technology can provide for determining when to adjust mattress firmness based on a sleep-state approach and/or a time-based approach. In the sleep-state approach, the disclosed technology can determine current sleep stages of the user based on sensed data about the user in the bed. The sensed data can include pressure changes in the mattress, temperature of the user, temperature of the mattress, heartrate, heart rate variability, respiration rate, breathing rate, etc. The disclosed technology can then determine firmness adjustments based on the determined current sleep stages of the user.

In the time-based approach, the disclosed technology can make a determination of whether the user is asleep or awake based on how much time the user is in the bed and based on how much time has passed since sleep onset. Since deep sleep establishes approximately one hour after sleep onset, first changes in mattress firmness can begin at that time. Subsequent firmness changes can also be measured from that time. The disclosed technology can then determine firmness adjustments based on how much time passes between different sleep stages that the user is expected to be in. Moreover, regardless of whether the sleep-state or the time-based approach is used, the disclosed technology can provide for resetting the mattress firmness to the user-defined or user-preferred firmness setting(s) once the user is within a predetermined timeframe before waking up to an alarm.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a bed having a mattress configured to support a sleeper in a sleep environment; a sensor system configured to sense at least one physical phenomenon through a sleep session and transmit sensor data to a controller based on the sensed physical phenomenon through the sleep session; and the controller, where the controller may include at least one processor and memory, the controller configured to receive, through the sleep session, the sensor data; select, from a plurality of optional algorithms, a selected algorithm based on at least one of the sensor data, user input, and checking a clock, where the optional algorithms include (i) a state-based algorithm and (ii) a schedule-based algorithm; update, through the sleep session, using the selected algorithm, a current sleep state of the sleeper; track the sleep session based on the update of the current sleep state of the sleeper through the sleep session; update, through the sleep session, using the tracking of the sleep session, a target environmental-parameter; and send, through the sleep session, automation instructions to an environmental controller based on the update of the target environmental-parameter. Other embodiments of this aspect include corresponding computer systems, apparatus, and computer programs recorded on one or more computer storage devices, each configured to perform the actions of the methods.

Implementations may include one or more of the following features. The environmental controller configured to: receive the automation instructions from the controller; and engage one or more devices according to the automation instructions such that the sleep environment of the sleeper is updated through the sleep session. The mattress includes at least one air chamber, where engaging the one or more devices according to the automation instructions include engaging a pump to increase pressure to the at least one air chamber of the mattress such that the firmness of the mattress is increased. Engaging the one or more devices according to the automation instructions includes engaging the pump to decrease pressure to the at least one air chamber of the mattress such that the firmness of the mattress is decreased. The target environment-parameter is a firmness of the mattress. The at least one physical phenomenon includes a heartrate, a respiration rate, a breathing rate, snoring, bodily movement of the sleeper, a determination that the sleeper has fallen asleep, a duration of time that has passed since sleep onset, a pressure change in the mattress, a temperature of the sleeper, and a temperature of a top surface of the mattress. The selected algorithm is the state-based algorithm, where the controller is configured to: update, through the sleep session, using the sensor data, the current sleep state of the sleeper; and track the sleep session through a sleep-state schedule based on the update of the current sleep state of the sleeper through the sleep session. The sleep-state schedule is defined using successive phases, each phase specifying i) one or more values for the current sleep state; and ii) one or more values for the target environmental-parameter. Tracking the sleep session through a sleep-state schedule based on the update of the current sleep state of the sleeper through the sleep session may include: maintaining identification of the current sleep state as a first phase of the successive phases; determining that the current sleep state matches the one or more values for the current sleep state specified by a second phase; and updating the identification of the current sleep state to a second phase that is successive to the first phase in the successive phases. The successive phases may include i) an initial sleep phase, ii) a middle sleep phase, and iii) a near-wakeup phase. The initial sleep phase is at least thirty minutes after the sleeper has entered the bed. The near-wakeup phase is between thirty and forty minutes before an alarm set by the sleeper. The initial sleep phase specifies i) an NREM sleep state for less than a threshold time period; and ii) a user-specified pressure setting; the middle sleep phase specifies i) an NREM sleep state for greater than the threshold time period; and ii) an increased pressure setting that is greater than the user-specified pressure setting; and the near-wakeup sleep phase specifies i) an REM sleep less than a threshold period of time near a scheduled wake-up time; and ii) the user-specified pressure setting. The selected algorithm is the schedule-based algorithm, where the controller is configured to: update, through the sleep session, using the sensor data, a current sleeping determination for the sleeper, the sleeping determination having possible values of awake and asleep; and track the sleep session through a sleep state-time based schedule based on a length of time that has elapsed since the current sleep determination was updated to asleep. The sleep state-time based schedule is defined using successive phases, each phase specifying i) one or more values for the current sleep determination; and ii) one or more values for the target environmental-parameter. Tracking the sleep session through a sleep state-time based schedule based on a length of time that has elapsed since the current sleep determination was updated to asleep may include: maintaining identification of the current sleep determination as a first phase of the successive phases; determining that the current sleep determination matches the one or more values for the current sleep determination specified by a second phase; and updating the identification of the current sleep determination to a second phase that is successive to the first phase in the successive phases. The controller is at least one of a home automation device, a mobile device, and a remote server that is in data communication with the sensor system and the environmental controller. The controller includes the environmental controller. Implementations of the described techniques may include hardware, a method or process, or computer software on a computer-accessible medium.

One general aspect includes a bed having a mattress configured to support a sleeper in a sleep environment; a sensor system configured to: sense at least one physical phenomenon through a sleep session and transmit sensor data to a controller based on the sensed physical phenomenon through the sleep session; the controller, where the controller may include at least one processor and memory, the controller configured to: receive, through the sleep session, the sensor data; update, through the sleep session, using the sensor data, a current sleep state of the sleeper; track the sleep session through a sleep-state schedule based on the update of the current sleep state of the sleeper through the sleep session; update, through the sleep session, using the tracking of the sleep session, a target environmental-parameter; and send, through the sleep session, automation instructions to an environmental controller based on the update of the target environmental-parameter; and the environmental controller configured to: receive the automation instructions; and engage one or more devices according to the automation instructions such that the sleep environment of the sleeper is updated through the sleep session. Other embodiments of this aspect include corresponding computer systems, apparatus, and computer programs recorded on one or more computer storage devices, each configured to perform the actions of the methods.

Implementations may include one or more of the following features. The sleep-state schedule is defined using successive phases, each phase specifying i) one or more values for the current sleep state; and ii) one or more values for the target environmental-parameter. Tracking the sleep session through a sleep-state schedule based on the update of the current sleep state of the sleeper through the sleep session may include: maintaining identification of the current sleep state as a first phase of the successive phases; determining that the current sleep state matches the one or more values for the current sleep state specified by a second phase; and updating the identification of the current sleep state to a second phase that is successive to the first phase in the successive phases. The successive phases may include i) an initial sleep phase, ii) a middle sleep phase, and iii) a near-wakeup phase. The initial sleep phase specifies i) an NREM sleep state for less than a threshold time period; and ii) a user-specified pressure setting; the middle sleep phase specifies i) an NREM sleep state for greater than the threshold time period; and ii) an increased pressure setting that is greater than the user-specified pressure setting; and the near-wakeup sleep phase specifies i) an REM sleep less than a threshold period of time near a scheduled wake-up time; and ii) the user-specified pressure setting. The controller is at least one of a home automation device, a mobile device, and a remote server that is in data communication with the sensor system and the environmental controller. The controller includes the environmental controller. The mattress includes at least one air chamber, where engaging the one or more devices according to the automation instructions include engaging a pump to increase pressure to the at least one air chamber of the mattress such that the firmness of the mattress is increased. Engaging the one or more devices according to the automation instructions includes engaging the pump to decrease pressure to the at least one air chamber of the mattress such that the firmness of the mattress is decreased. The target environment-parameter is a firmness of the mattress. The at least one physical phenomenon includes a heartrate, a respiration rate, a breathing rate, snoring, bodily movement of the sleeper, a determination that the sleeper has fallen asleep, a duration of time that has passed since sleep onset, a pressure change in the mattress, a temperature of the sleeper, and a temperature of a top surface of the mattress Implementations of the described techniques may include hardware, a method or process, or computer software on a computer-accessible medium.

One general aspect includes a bed having a mattress configured to support a sleeper in a sleep environment; a sensor system configured to: sense at least one physical phenomenon through a sleep session; transmit sensor data to a controller based on the sensed physical phenomenon through the sleep session; the controller, where the controller may include at least one processor and memory, the controller configured to: receive, through the sleep session, the sensor data; update, through the sleep session, using the sensor data, a current sleeping determination for the sleeper, the sleeping determination having possible values of awake and asleep; track the sleep session through a sleep-state schedule based on a length of time that has elapsed since the current sleep determination was updated to asleep; update, through the sleep session, using the tracking of the sleep session, a target environmental-parameter; and send, through the sleep session, automation instructions to an environmental controller based on the update of the target environmental-parameter; and the environmental controller configured to: receive the automation instructions; and engage one or more devices according to the automation instructions such that the sleep environment of the sleeper is updated through the sleep session. Other embodiments of this aspect include corresponding computer systems, apparatus, and computer programs recorded on one or more computer storage devices, each configured to perform the actions of the methods.

Implementations may include one or more of the following features. The sleep-state schedule is defined using successive phases, each phase specifying i) one or more values for the current sleep determination; and ii) one or more values for the target environmental-parameter. Tracking the sleep session through a sleep-state schedule based on a length of time that has elapsed since the current sleep determination was updated to asleep may include: maintaining identification of the current sleep determination as a first phase of the successive phases; determining that the current sleep determination matches the one or more values for the current sleep determination specified by a second phase; and updating the identification of the current sleep determination to a second phase that is successive to the first phase in the successive phases. The successive phases may include i) an initial sleep phase, ii) a middle sleep phase, and iii) a near-wakeup phase. The initial sleep phase specifies i) an NREM sleep state for less than a threshold time period; and ii) a user-specified pressure setting; the middle sleep phase specifies i) an NREM sleep state for greater than the threshold time period; and ii) an increased pressure setting that is greater than the user-specified pressure setting; and the near-wakeup sleep phase specifies i) an REM sleep less than a threshold period of time near a scheduled wake-up time; and ii) the user-specified pressure setting. The controller is at least one of a home automation device, a mobile device, and a remote server that is in data communication with the sensor system and the environmental controller. The controller includes the environmental controller. The mattress includes at least one air chamber, where engaging the one or more devices according to the automation instructions include engaging a pump to increase pressure to the at least one air chamber of the mattress such that the firmness of the mattress is increased. Engaging the one or more devices according to the automation instructions includes engaging the pump to decrease pressure to the at least one air chamber of the mattress such that the firmness of the mattress is decreased. The target environment-parameter is a firmness of the mattress. The at least one physical phenomenon includes a heartrate, a respiration rate, a breathing rate, snoring, bodily movement of the sleeper, a determination that the sleeper has fallen asleep, a duration of time that has passed since sleep onset, a pressure change in the mattress, a temperature of the sleeper, and a temperature of a top surface of the mattress. Implementations of the described techniques may include hardware, a method or process, or computer software on a computer-accessible medium.

The disclosed technology can provide one or more advantages. For example, adjusting mattress firmness based on user sleep stages can optimize user comfortability. An optimal degree of firmness can be personal and can depend on body composition and muscle tone. During sleep, however, muscle tone can change depending on the sleep stages of the user. Thus, the disclosed technology provides for detecting or otherwise determining the sleep stages of the user to dynamically adjust firmness and maximize sleep comfort. Sleep comfort can be improved through better spinal alignment, which can benefit regeneration and reduce back pain.

As another example, the disclosed technology can provide for improving overall sleep quality of the user. Imperceptible or perceptible changes small enough not to disturb sleep in mattress firmness throughout the sleep session can provide the user with continuous comfort and continuous sleep (e.g., in other words, the user may not wake up during the night from the changes in mattress firmness or discomfort). As the user experiences more comfort and better spinal alignment, the user can wake up rejuvenated and, overall, feeling better. The better sleep that the user experiences, the better sleep quality.

As yet another example, the user may not notice the mattress firmness adjustments that can be made throughout the sleep session, thereby resulting in continuous and improved sleep quality and comfort. Allowing for varying levels of mattress firmness throughout the sleep session that is tied to sleep phases can provide for targeted periods of optimized spine alignment that the user needs while their awareness of external changes are minimized. In other words, since mattress firmness adjustments can be made during stages of deep sleep (e.g., in REM sleep when the user's muscle tone is reduced), the user may not realize that firmness of the mattress is being automatically changed. Such unperceivable adjustments can be advantageous because the adjustments may not disrupt the user's sleep session or cause the user to wake up. The user can experience a continuous and improved sleep quality and comfort through the sleep session.

As yet another example, the technology here may enable therapeutic interventions in cases of pain management, recovery from injury or surgery, treatment of issues such as gastroesophageal reflux (GERD), etc.

As yet another example, the technology can provide for energy savings over alternatives that do not use this technology, and can provide for a superior sleep experience.

Other features, aspects and potential advantages will be apparent from the accompanying description and figures.

DESCRIPTION OF DRAWINGS

Like reference symbols in the various drawings indicate like elements.

DETAILED DESCRIPTION

The present disclosure generally describes systems, methods, and techniques for adjusting mattress firmness based on a current sleep state of a user (e.g., sleeper). As described herein, a user's muscle tone can be reduced during different sleep stages. When muscle tone is absent, the user may not experience proper spinal alignment or comfortability. Therefore, using the disclosed technology, the mattress firmness can be adjusted during different sleep stages to provide proper spinal alignment and comfortability when the user's muscle tone is absent.

A bed system can include a mattress, one or more sensors, and a controller. The sensors can detect conditions of the user as the user rests on the mattress. The conditions can be used by the controller to determine mattress firmness adjustments. For example, the conditions can be used by the controller to determine a current sleep stage (e.g., sleep state; restful vs. restless; REM, N1, N2, and N3) of the user. Depending on the current sleep stage, the controller can determine appropriate adjustments to the mattress firmness, such as decreasing pressure in the mattress when the user is in a light sleep stage and increasing pressure in the mattress when the user is in a deep sleep stage.

In some implementations, the controller can determine that pressure in air chambers of the mattress can be increased by a certain amount in order to make the mattress firmer during a particular sleep stage of the user (e.g., during REM sleep and/or when the user's muscle tone is otherwise absent or reduced). The certain amount can be a percentage increase of a user-defined and/or user-preferred firmness setting. The controller can also determine that pressure in air chambers of the mattress can be decreased by a certain amount in order to make the mattress less firm during a particular sleep stage of the user (e.g., during light sleep and/or when the user's muscle tone is otherwise present).

As another example, the controller can determine adjustments to the mattress firmness based on projected timing of when the user is awake, asleep, and in one or more different sleep stages. Thus, adjustments to the mattress firmness can be made based on timing of different sleep stages. In some implementations, the timing can be specific to historic sleep timing information about the user. In some implementations, the timing can be generic across a population of users defined with parameters such as age, gender or other demographics and/or locations such as ZIP code or other tagging. Adjusting the mattress firmness based on the current sleep stage of the user and/or timing of different sleep stages can be beneficial to provide improved sleep quality, comfortability, and spinal alignment.

Example Airbed Hardware

Figure 1:
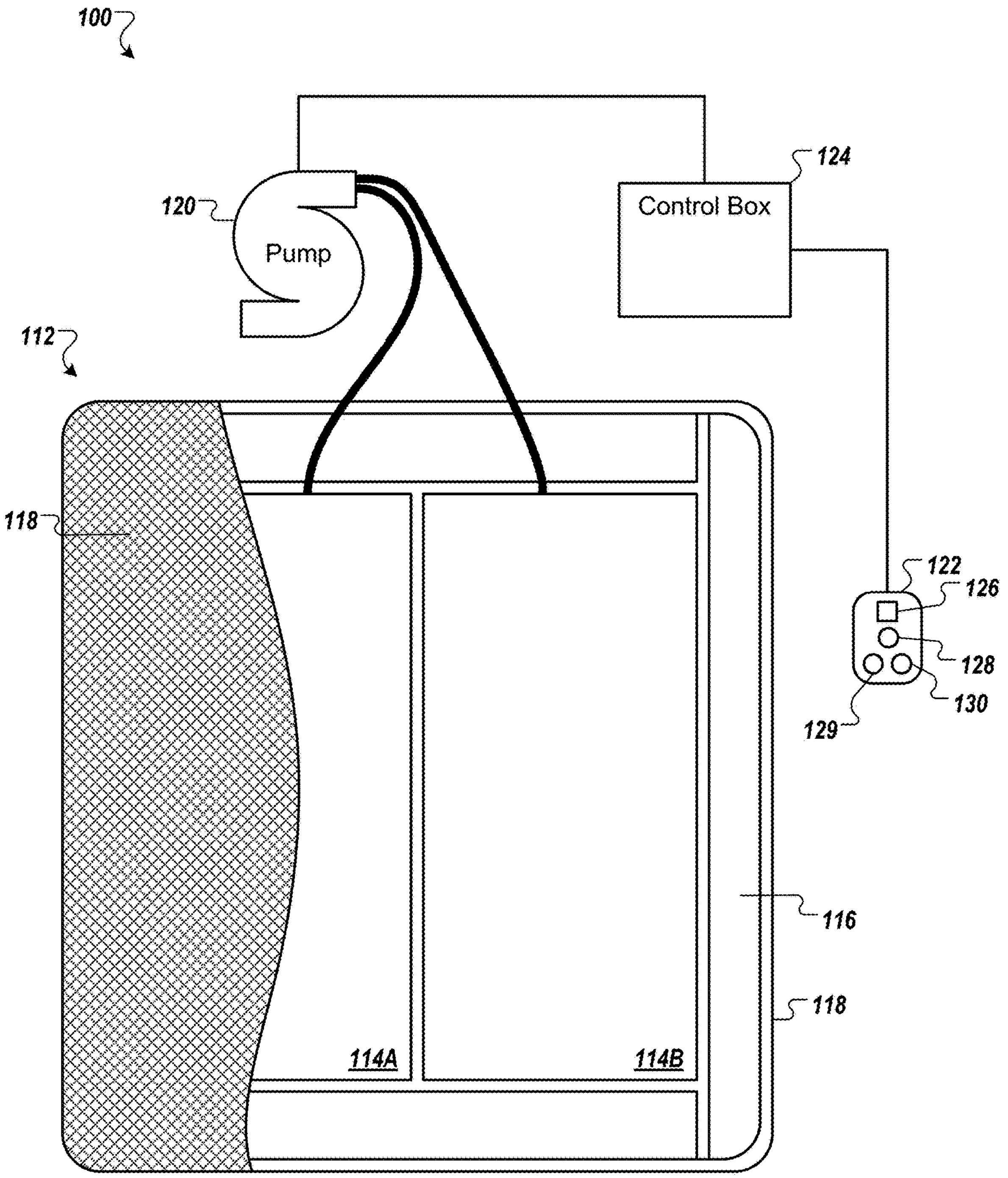
FIG. 1 shows an example air bed system.

FIG. 1 shows an example air bed system 100 that includes a bed 112. The bed 112 includes at least one air chamber 114 surrounded by a resilient border 116 and encapsulated by bed ticking 118. The resilient border 116 can comprise any suitable material, such as foam.

As illustrated in FIG. 1, the bed 112 can be a two chamber design having first and second fluid chambers, such as a first air chamber 114A and a second air chamber 114B. In alternative embodiments, the bed 112 can include chambers for use with fluids other than air that are suitable for the application. In some embodiments, such as single beds or kids' beds, the bed 112 can include a single air chamber 114A or 114B or multiple air chambers 114A and 114B. First and second air chambers 114A and 114B can be in fluid communication with a pump 120. The pump 120 can be in electrical communication with a remote control 122 via control box 124. The control box 124 can include a wired or wireless communications interface for communicating with one or more devices, including the remote control 122. The control box 124 can be configured to operate the pump 120 to cause increases and decreases in the fluid pressure of the first and second air chambers 114A and 114B based upon commands input by a user using the remote control 122. In some implementations, the control box 124 is integrated into a housing of the pump 120.

The remote control 122 can include a display 126, an output selecting mechanism 128, a pressure increase button 129, and a pressure decrease button 130. The output selecting mechanism 128 can allow the user to switch air flow generated by the pump 120 between the first and second air chambers 114A and 114B, thus enabling control of multiple air chambers with a single remote control 122 and a single pump 120. For example, the output selecting mechanism 128 can by a physical control (e.g., switch or button) or an input control displayed on display 126. Alternatively, separate remote control units can be provided for each air chamber and can each include the ability to control multiple air chambers. Pressure increase and decrease buttons 129 and 130 can allow a user to increase or decrease the pressure, respectively, in the air chamber selected with the output selecting mechanism 128. Adjusting the pressure within the selected air chamber can cause a corresponding adjustment to the firmness of the respective air chamber. In some embodiments, the remote control 122 can be omitted or modified as appropriate for an application. For example, in some embodiments the bed 112 can be controlled by a computer, tablet, smart phone, or other device in wired or wireless communication with the bed 112.

Figure 2:
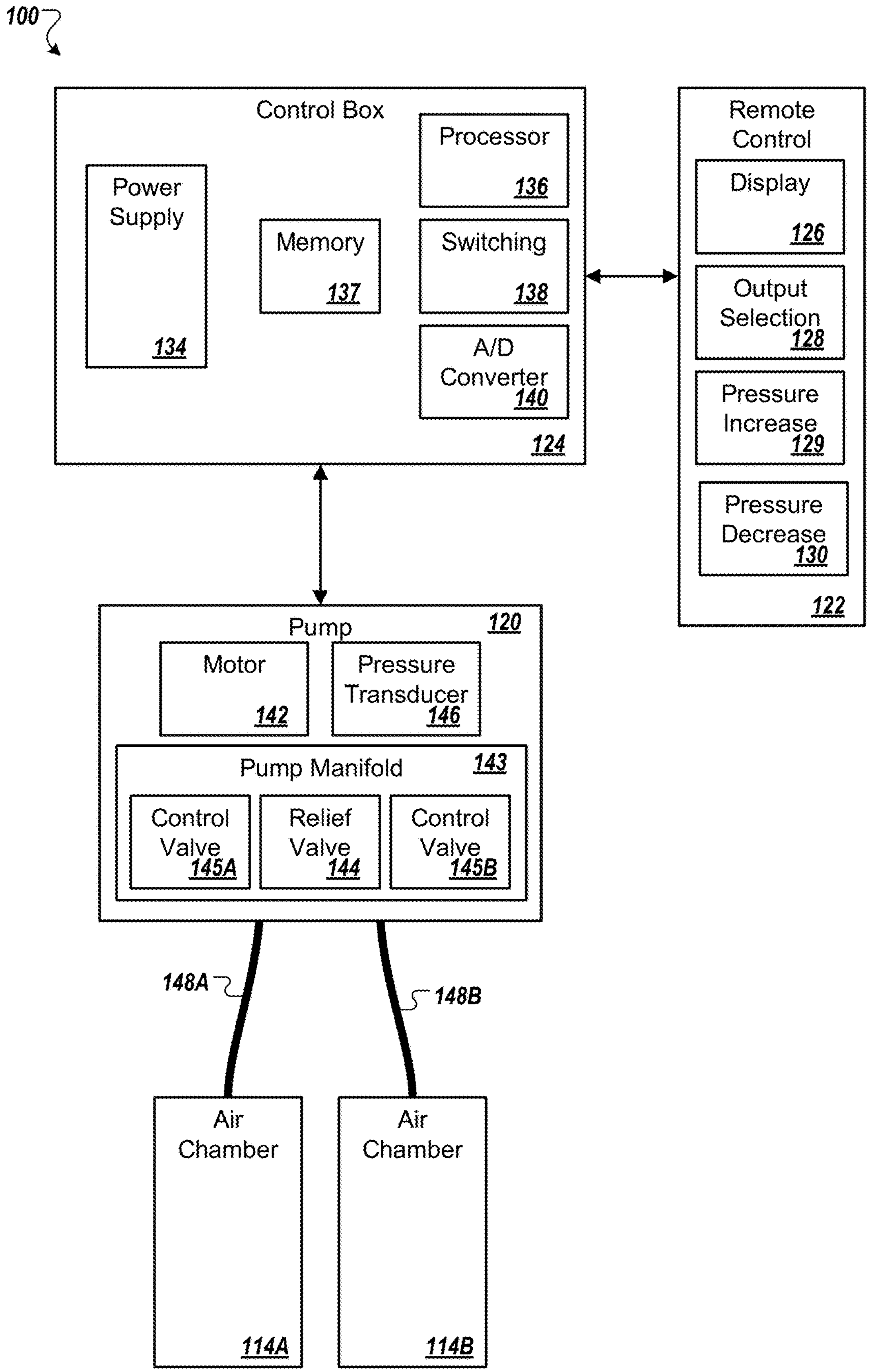
FIG. 2 is a block diagram of an example of various components of an air bed system.

FIG. 2 is a block diagram of an example of various components of an air bed system. For example, these components can be used in the example air bed system 100. As shown in FIG. 2, the control box 124 can include a power supply 134, a processor 136, a memory 137, a switching mechanism 138, and an analog to digital (A/D) converter 140. The switching mechanism 138 can be, for example, a relay or a solid state switch. In some implementations, the switching mechanism 138 can be located in the pump 120 rather than the control box 124.

The pump 120 and the remote control 122 are in two-way communication with the control box 124. The pump 120 includes a motor 142, a pump manifold 143, a relief valve 144, a first control valve 145A, a second control valve 145B, and a pressure transducer 146. The pump 120 is fluidly connected with the first air chamber 114A and the second air chamber 114B via a first tube 148A and a second tube 148B, respectively. The first and second control valves 145A and 145B can be controlled by switching mechanism 138, and are operable to regulate the flow of fluid between the pump 120 and first and second air chambers 114A and 114B, respectively.

In some implementations, the pump 120 and the control box 124 can be provided and packaged as a single unit. In some alternative implementations, the pump 120 and the control box 124 can be provided as physically separate units. In some implementations, the control box 124, the pump 120, or both are integrated within or otherwise contained within a bed frame or bed support structure that supports the bed 112. In some implementations, the control box 124, the pump 120, or both are located outside of a bed frame or bed support structure (as shown in the example in FIG. 1).

The example air bed system 100 depicted in FIG. 2 includes the two air chambers 114A and 114B and the single pump 120. However, other implementations can include an air bed system having two or more air chambers and one or more pumps incorporated into the air bed system to control the air chambers. For example, a separate pump can be associated with each air chamber of the air bed system or a pump can be associated with multiple chambers of the air bed system. Separate pumps can allow each air chamber to be inflated or deflated independently and simultaneously. Furthermore, additional pressure transducers can also be incorporated into the air bed system such that, for example, a separate pressure transducer can be associated with each air chamber.

In use, the processor 136 can, for example, send a decrease pressure command to one of air chambers 114A or 114B, and the switching mechanism 138 can be used to convert the low voltage command signals sent by the processor 136 to higher operating voltages sufficient to operate the relief valve 144 of the pump 120 and open the control valve 145A or 145B. Opening the relief valve 144 can allow air to escape from the air chamber 114A or 114B through the respective air tube 148A or 148B. During deflation, the pressure transducer 146 can send pressure readings to the processor 136 via the A/D converter 140. The A/D converter 140 can receive analog information from pressure transducer 146 and can convert the analog information to digital information useable by the processor 136. The processor 136 can send the digital signal to the remote control 122 to update the display 126 in order to convey the pressure information to the user.

As another example, the processor 136 can send an increase pressure command. The pump motor 142 can be energized in response to the increase pressure command and send air to the designated one of the air chambers 114A or 114B through the air tube 148A or 148B via electronically operating the corresponding valve 145A or 145B. While air is being delivered to the designated air chamber 114A or 114B in order to increase the firmness of the chamber, the pressure transducer 146 can sense pressure within the pump manifold 143. Again, the pressure transducer 146 can send pressure readings to the processor 136 via the A/D converter 140. The processor 136 can use the information received from the A/D converter 140 to determine the difference between the actual pressure in air chamber 114A or 114B and the desired pressure. The processor 136 can send the digital signal to the remote control 122 to update display 126 in order to convey the pressure information to the user.

Generally speaking, during an inflation or deflation process, the pressure sensed within the pump manifold 143 can provide an approximation of the pressure within the respective air chamber that is in fluid communication with the pump manifold 143. An example method of obtaining a pump manifold pressure reading that is substantially equivalent to the actual pressure within an air chamber includes turning off pump 120, allowing the pressure within the air chamber 114A or 114B and the pump manifold 143 to equalize, and then sensing the pressure within the pump manifold 143 with the pressure transducer 146. Thus, providing a sufficient amount of time to allow the pressures within the pump manifold 143 and chamber 114A or 114B to equalize can result in pressure readings that are accurate approximations of the actual pressure within air chamber 114A or 114B. In some implementations, the pressure of the air chambers 114A and/or 114B can be continuously monitored using multiple pressure sensors (not shown).

In some implementations, information collected by the pressure transducer 146 can be analyzed to determine various states of a person lying on the bed 112. For example, the processor 136 can use information collected by the pressure transducer 146 to determine a heart rate or a respiration rate for a person lying in the bed 112. For example, a user can be lying on a side of the bed 112 that includes the chamber 114A. The pressure transducer 146 can monitor fluctuations in pressure of the chamber 114A and this information can be used to determine the user's heart rate and/or respiration rate. As another example, additional processing can be performed using the collected data to determine a sleep state of the person (e.g., awake, light sleep, deep sleep). For example, the processor 136 can determine when a person falls asleep and, while asleep, the various sleep states of the person.

Additional information associated with a user of the air bed system 100 that can be determined using information collected by the pressure transducer 146 includes motion of the user, presence of the user on a surface of the bed 112, weight of the user, heart arrhythmia of the user, and apnea. Taking user presence detection for example, the pressure transducer 146 can be used to detect the user's presence on the bed 112, e.g., via a gross pressure change determination and/or via one or more of a respiration rate signal, heart rate signal, and/or other biometric signals. For example, a simple pressure detection process can identify an increase in pressure as an indication that the user is present on the bed 112. As another example, the processor 136 can determine that the user is present on the bed 112 if the detected pressure increases above a specified threshold (so as to indicate that a person or other object above a certain weight is positioned on the bed 112). As yet another example, the processor 136 can identify an increase in pressure in combination with detected slight, rhythmic fluctuations in pressure as corresponding to the user being present on the bed 112. The presence of rhythmic fluctuations can be identified as being caused by respiration or heart rhythm (or both) of the user. The detection of respiration or a heartbeat can distinguish between the user being present on the bed and another object (e.g., a suit case) being placed upon the bed.

In some implementations, fluctuations in pressure can be measured at the pump 120. For example, one or more pressure sensors can be located within one or more internal cavities of the pump 120 to detect fluctuations in pressure within the pump 120. The fluctuations in pressure detected at the pump 120 can indicate fluctuations in pressure in one or both of the chambers 114A and 114B. One or more sensors located at the pump 120 can be in fluid communication with the one or both of the chambers 114A and 114B, and the sensors can be operative to determine pressure within the chambers 114A and 114B. The control box 124 can be configured to determine at least one vital sign (e.g., heart rate, respiratory rate) based on the pressure within the chamber 114A or the chamber 114B.

In some implementations, the control box 124 can analyze a pressure signal detected by one or more pressure sensors to determine a heart rate, respiration rate, and/or other vital signs of a user lying or sitting on the chamber 114A or the chamber 114B. More specifically, when a user lies on the bed 112 positioned over the chamber 114A, each of the user's heart beats, breaths, and other movements can create a force on the bed 112 that is transmitted to the chamber 114A. As a result of the force input to the chamber 114A from the user's movement, a wave can propagate through the chamber 114A and into the pump 120. A pressure sensor located at the pump 120 can detect the wave, and thus the pressure signal output by the sensor can indicate a heart rate, respiratory rate, or other information regarding the user.

With regard to sleep state, air bed system 100 can determine a user's sleep state by using various biometric signals such as heart rate, respiration, and/or movement of the user. While the user is sleeping, the processor 136 can receive one or more of the user's biometric signals (e.g., heart rate, respiration, and motion) and determine the user's present sleep state based on the received biometric signals. In some implementations, signals indicating fluctuations in pressure in one or both of the chambers 114A and 114B can be amplified and/or filtered to allow for more precise detection of heart rate and respiratory rate.

The control box 124 can perform a pattern recognition algorithm or other calculation based on the amplified and filtered pressure signal to determine the user's heart rate and respiratory rate. For example, the algorithm or calculation can be based on assumptions that a heart rate portion of the signal has a frequency in the range of 0.5-4.0 Hz and that a respiration rate portion of the signal a has a frequency in the range of less than 1 Hz. The control box 124 can also be configured to determine other characteristics of a user based on the received pressure signal, such as blood pressure, tossing and turning movements, rolling movements, limb movements, weight, the presence or lack of presence of a user, and/or the identity of the user. Techniques for monitoring a user's sleep using heart rate information, respiration rate information, and other user information are disclosed in U.S. Patent Application Publication No. 20100170043 to Steven J. Young et al., titled "APPARATUS FOR MONITORING VITAL SIGNS," the entire contents of which is incorporated herein by reference.

For example, the pressure transducer 146 can be used to monitor the air pressure in the chambers 114A and 114B of the bed 112. If the user on the bed 112 is not moving, the air pressure changes in the air chamber 114A or 114B can be relatively minimal, and can be attributable to respiration and/or heartbeat. When the user on the bed 112 is moving, however, the air pressure in the mattress can fluctuate by a much larger amount. Thus, the pressure signals generated by the pressure transducer 146 and received by the processor 136 can be filtered and indicated as corresponding to motion, heartbeat, or respiration.

In some implementations, rather than performing the data analysis in the control box 124 with the processor 136, a digital signal processor (DSP) can be provided to analyze the data collected by the pressure transducer 146. Alternatively, the data collected by the pressure transducer 146 could be sent to a cloud-based computing system for remote analysis.

In some implementations, the example air bed system 100 further includes a temperature controller configured to increase, decrease, or maintain the temperature of a bed, for example for the comfort of the user. For example, a pad can be placed on top of or be part of the bed 112, or can be placed on top of or be part of one or both of the chambers 114A and 114B. Air can be pushed through the pad and vented to cool off a user of the bed. Conversely, the pad can include a heating element that can be used to keep the user warm. In some implementations, the temperature controller can receive temperature readings from the pad. In some implementations, separate pads are used for the different sides of the bed 112 (e.g., corresponding to the locations of the chambers 114A and 114B) to provide for differing temperature control for the different sides of the bed.

In some implementations, the user of the air bed system 100 can use an input device, such as the remote control 122, to input a desired temperature for the surface of the bed 112 (or for a portion of the surface of the bed 112). The desired temperature can be encapsulated in a command data structure that includes the desired temperature as well as identifies the temperature controller as the desired component to be controlled. The command data structure can then be transmitted via Bluetooth or another suitable communication protocol to the processor 136. In various examples, the command data structure is encrypted before being transmitted. The temperature controller can then configure its elements to increase or decrease the temperature of the pad depending on the temperature input into remote control 122 by the user.

In some implementations, data can be transmitted from a component back to the processor 136 or to one or more display devices, such as the display 126. For example, the current temperature as determined by a sensor element of temperature controller, the pressure of the bed, the current position of the foundation or other information can be transmitted to control box 124. The control box 124 can then transmit the received information to remote control 122 where it can be displayed to the user (e.g., on the display 126).

In some implementations, the example air bed system 100 further includes an adjustable foundation and an articulation controller configured to adjust the position of a bed (e.g., the bed 112) by adjusting the adjustable foundation that supports the bed. For example, the articulation controller can adjust the bed 112 from a flat position to a position in which a head portion of a mattress of the bed is inclined upward (e.g., to facilitate a user sitting up in bed and/or watching television). In some implementations, the bed 112 includes multiple separately articulable sections. For example, portions of the bed corresponding to the locations of the chambers 114A and 114B can be articulated independently from each other, to allow one person positioned on the bed 112 surface to rest in a first position (e.g., a flat position) while a second person rests in a second position (e.g., an reclining position with the head raised at an angle from the waist). In some implementations, separate positions can be set for two different beds (e.g., two twin beds placed next to each other). The foundation of the bed 112 can include more than one zone that can be independently adjusted. The articulation controller can also be configured to provide different levels of massage to one or more users on the bed 112.

Example of a Bed in a Bedroom Environment

Figure 3:
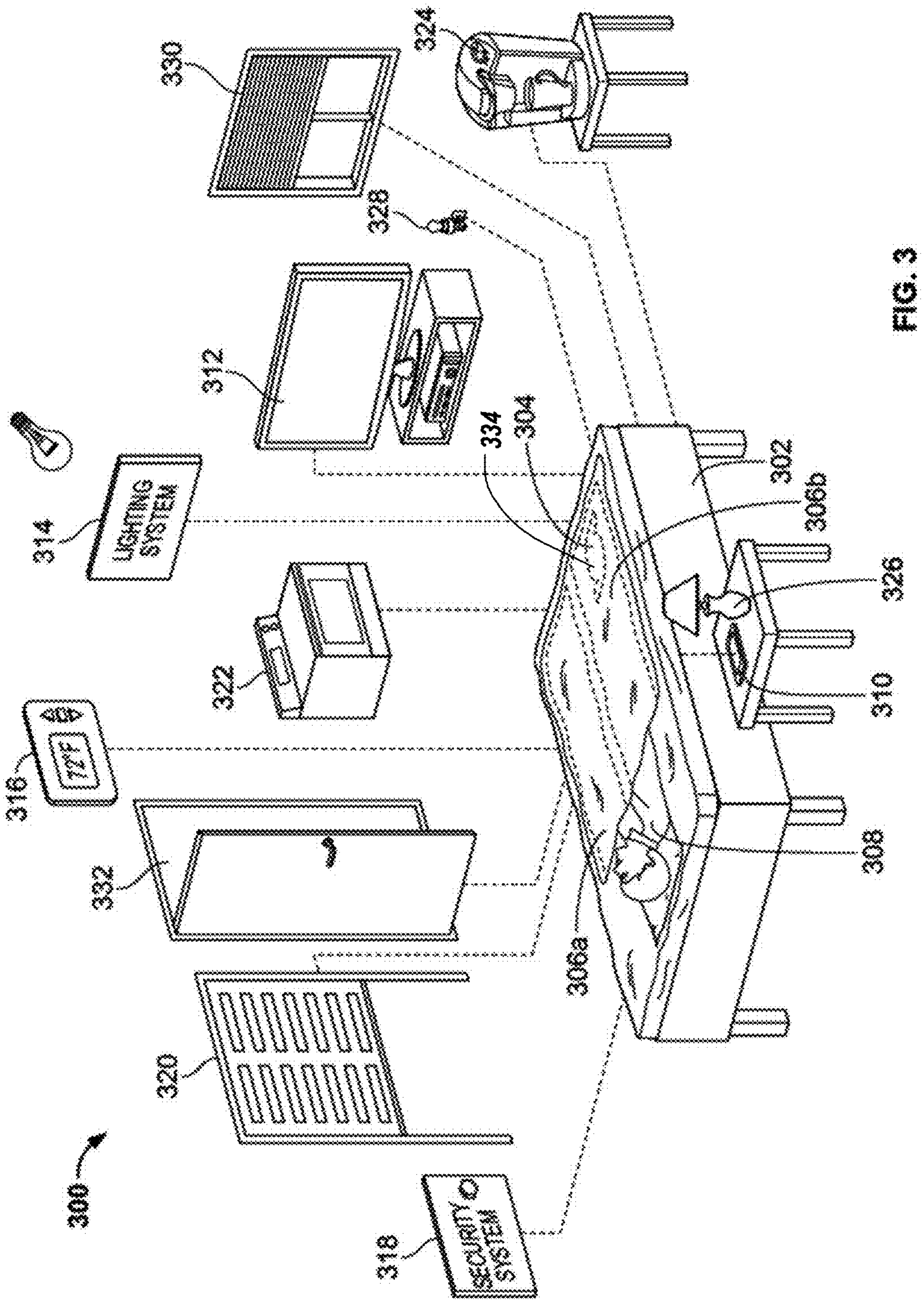
FIG. 3 shows an example environment including a bed in communication with devices located in and around a home.

FIG. 3 shows an example environment 300 including a bed 302 in communication with devices located in and around a home. In the example shown, the bed 302 includes pump 304 for controlling air pressure within two air chambers 306*a* and 306*b* (as described above with respect to the air chambers 114A-114B). The pump 304 additionally includes circuitry for controlling inflation and deflation functionality performed by the pump 304. The circuitry is further programmed to detect fluctuations in air pressure of the air chambers 306*a-b* and used the detected fluctuations in air pressure to identify bed presence of a user 308, sleep state of the user 308, movement of the user 308, and biometric signals of the user 308 such as heart rate and respiration rate. In the example shown, the pump 304 is located within a support structure of the bed 302 and the control circuitry 334 for controlling the pump 304 is integrated with the pump 304. In some implementations, the control circuitry 334 is physically separate from the pump 304 and is in wireless or wired communication with the pump 304. In some implementations, the pump 304 and/or control circuitry 334 are located outside of the bed 302. In some implementations, various control functions can be performed by systems located in different physical locations. For example, circuitry for controlling actions of the pump 304 can be located within a pump casing of the pump 304 while control circuitry 334 for performing other functions associated with the bed 302 can be located in another portion of the bed 302, or external to the bed 302. As another example, control circuitry 334 located within the pump 304 can communicate with control circuitry 334 at a remote location through a LAN or WAN (e.g., the internet). As yet another example, the control circuitry 334 can be included in the control box 124 of FIGS. 1 and 2.

In some implementations, one or more devices other than, or in addition to, the pump 304 and control circuitry 334 can be utilized to identify user bed presence, sleep state, movement, and biometric signals. For example, the bed 302 can include a second pump in addition to the pump 304, with each of the two pumps connected to a respective one of the air chambers 306*a-b*. For example, the pump 304 can be in fluid communication with the air chamber 306*b* to control inflation and deflation of the air chamber 306*b* as well as detect user signals for a user located over the air chamber 306*b* such as bed presence, sleep state, movement, and biometric signals while the second pump is in fluid communication with the air chamber 306*a* to control inflation and deflation of the air chamber 306*a* as well as detect user signals for a user located over the air chamber 306*a*.

As another example, the bed 302 can include one or more pressure sensitive pads or surface portions that are operable to detect movement, including user presence, user motion, respiration, and heart rate. For example, a first pressure sensitive pad can be incorporated into a surface of the bed 302 over a left portion of the bed 302, where a first user would normally be located during sleep, and a second pressure sensitive pad can be incorporated into the surface of the bed 302 over a right portion of the bed 302, where a second user would normally be located during sleep. The movement detected by the one or more pressure sensitive pads or surface portions can be used by control circuitry 334 to identify user sleep state, bed presence, or biometric signals.

In some implementations, information detected by the bed (e.g., motion information) is processed by control circuitry 334 (e.g., control circuitry 334 integrated with the pump 304) and provided to one or more user devices such as a user device 310 for presentation to the user 308 or to other users. In the example depicted in FIG. 3, the user device 310 is a tablet device; however, in some implementations, the user device 310 can be a personal computer, a smart phone, a smart television (e.g., a television 312), or other user device capable of wired or wireless communication with the control circuitry 334. The user device 310 can be in communication with control circuitry 334 of the bed 302 through a network or through direct point-to-point communication. For example, the control circuitry 334 can be connected to a LAN (e.g., through a Wi-Fi router) and communicate with the user device 310 through the LAN. As another example, the control circuitry 334 and the user device 310 can both connect to the Internet and communicate through the Internet. For example, the control circuitry 334 can connect to the Internet through a WiFi router and the user device 310 can connect to the Internet through communication with a cellular communication system. As another example, the control circuitry 334 can communicate directly with the user device 310 through a wireless communication protocol such as Bluetooth. As yet another example, the control circuitry 334 can communicate with the user device 310 through a wireless communication protocol such as ZigBee, Z-Wave, infrared, or another wireless communication protocol suitable for the application. As another example, the control circuitry 334 can communicate with the user device 310 through a wired connection such as, for example, a USB connector, serial/RS232, or another wired connection suitable for the application.

The user device 310 can display a variety of information and statistics related to sleep, or user 308's interaction with the bed 302. For example, a user interface displayed by the user device 310 can present information including amount of sleep for the user 308 over a period of time (e.g., a single evening, a week, a month, etc.) amount of deep sleep, ratio of deep sleep to restless sleep, time lapse between the user 308 getting into bed and the user 308 falling asleep, total amount of time spent in the bed 302 for a given period of time, heart rate for the user 308 over a period of time, respiration rate for the user 308 over a period of time, or other information related to user interaction with the bed 302 by the user 308 or one or more other users of the bed 302. In some implementations, information for multiple users can be presented on the user device 310, for example information for a first user positioned over the air chamber **306*a* can be presented along with information for a second user positioned over the air chamber 306*b*. In some implementations, the information presented on the user device 310 can vary according to the age of the user 308. For example, the information presented on the user device 310 can evolve with the age of the user 308 such that different information is presented on the user device 310 as the user 308** ages as a child or an adult.

The user device 310 can also be used as an interface for the control circuitry 334 of the bed 302 to allow the user 308 to enter information. The information entered by the user 308 can be used by the control circuitry 334 to provide better information to the user or to various control signals for controlling functions of the bed 302 or other devices. For example, the user can enter information such as weight, height, and age and the control circuitry 334 can use this information to provide the user 308 with a comparison of the user's tracked sleep information to sleep information of other people having similar weights, heights, and/or ages as the user 308. As another example, the user 308 can use the user device 310 as an interface for controlling air pressure of the air chambers **306*a* and 306*b*, for controlling various recline or incline positions of the bed 302, for controlling temperature of one or more surface temperature control devices of the bed 302, or for allowing the control circuitry 334** to generate control signals for other devices (as described in greater detail below).

In some implementations, control circuitry 334 of the bed 302 (e.g., control circuitry 334 integrated into the pump 304) can communicate with other first, second, or third party devices or systems in addition to or instead of the user device 310. For example, the control circuitry 334 can communicate with the television 312, a lighting system 314, a thermostat 316, a security system 318, or other house hold devices such as an oven 322, a coffee maker 324, a lamp 326, and a nightlight 328. Other examples of devices and/or systems that the control circuitry 334 can communicate with include a system for controlling window blinds 330, one or more devices for detecting or controlling the states of one or more doors 332 (such as detecting if a door is open, detecting if a door is locked, or automatically locking a door), and a system for controlling a garage door 320 (e.g., control circuitry 334 integrated with a garage door opener for identifying an open or closed state of the garage door 320 and for causing the garage door opener to open or close the garage door 320). Communications between the control circuitry 334 of the bed 302 and other devices can occur through a network (e.g., a LAN or the Internet) or as point-to-point communication (e.g., using Bluetooth, radio communication, or a wired connection). In some implementations, control circuitry 334 of different beds 302 can communicate with different sets of devices. For example, a kid bed may not communicate with and/or control the same devices as an adult bed. In some embodiments, the bed 302 can evolve with the age of the user such that the control circuitry 334 of the bed 302 communicates with different devices as a function of age of the user.

The control circuitry 334 can receive information and inputs from other devices/systems and use the received information and inputs to control actions of the bed 302 or other devices. For example, the control circuitry 334 can receive information from the thermostat 316 indicating a current environmental temperature for a house or room in which the bed 302 is located. The control circuitry 334 can use the received information (along with other information) to determine if a temperature of all or a portion of the surface of the bed 302 should be raised or lowered. The control circuitry 334 can then cause a heating or cooling mechanism of the bed 302 to raise or lower the temperature of the surface of the bed 302. For example, the user 308 can indicate a desired sleeping temperature of 74 degrees while a second user of the bed 302 indicates a desired sleeping temperature of 72 degrees. The thermostat 316 can indicate to the control circuitry 334 that the current temperature of the bedroom is 72 degrees. The control circuitry 334 can identify that the user 308 has indicated a desired sleeping temperature of 74 degrees, and send control signals to a heating pad located on the user 308's side of the bed to raise the temperature of the portion of the surface of the bed 302 where the user 308 is located to raise the temperature of the user 308's sleeping surface to the desired temperature.

The control circuitry 334 can also generate control signals controlling other devices and propagate the control signals to the other devices. In some implementations, the control signals are generated based on information collected by the control circuitry 334, including information related to user interaction with the bed 302 by the user 308 and/or one or more other users. In some implementations, information collected from one or more other devices other than the bed 302 are used when generating the control signals. For example, information relating to environmental occurrences (e.g., environmental temperature, environmental noise level, and environmental light level), time of day, time of year, day of the week, or other information can be used when generating control signals for various devices in communication with the control circuitry 334 of the bed 302. For example, information on the time of day can be combined with information relating to movement and bed presence of the user 308 to generate control signals for the lighting system 314. In some implementations, rather than or in addition to providing control signals for one or more other devices, the control circuitry 334 can provide collected information (e.g., information related to user movement, bed presence, sleep state, or biometric signals for the user 308) to one or more other devices to allow the one or more other devices to utilize the collected information when generating control signals. For example, control circuitry 334 of the bed 302 can provide information relating to user interactions with the bed 302 by the user 308 to a central controller (not shown) that can use the provided information to generate control signals for various devices, including the bed 302.

Still referring to FIG. 3, the control circuitry 334 of the bed 302 can generate control signals for controlling actions of other devices, and transmit the control signals to the other devices in response to information collected by the control circuitry 334, including bed presence of the user 308, sleep state of the user 308, and other factors. For example, control circuitry 334 integrated with the pump 304 can detect a feature of a mattress of the bed 302, such as an increase in pressure in the air chamber 306*b*, and use this detected increase in air pressure to determine that the user 308 is present on the bed 302. In some implementations, the control circuitry 334 can identify a heart rate or respiratory rate for the user 308 to identify that the increase in pressure is due to a person sitting, laying, or otherwise resting on the bed 302 rather than an inanimate object (such as a suitcase) having been placed on the bed 302. In some implementations, the information indicating user bed presence is combined with other information to identify a current or future likely state for the user 308. For example, a detected user bed presence at 11:00 am can indicate that the user is sitting on the bed (e.g., to tie her shoes, or to read a book) and does not intend to go to sleep, while a detected user bed presence at 10:00 pm can indicate that the user 308 is in bed for the evening and is intending to fall asleep soon. As another example, if the control circuitry 334 detects that the user 308 has left the bed 302 at 6:30 am (e.g., indicating that the user 308 has woken up for the day), and then later detects user bed presence of the user 308 at 7:30 am, the control circuitry 334 can use this information that the newly detected user bed presence is likely temporary (e.g., while the user 308 ties her shoes before heading to work) rather than an indication that the user 308 is intending to stay on the bed 302 for an extended period.

In some implementations, the control circuitry 334 is able to use collected information (including information related to user interaction with the bed 302 by the user 308, as well as environmental information, time information, and input received from the user) to identify use patterns for the user 308. For example, the control circuitry 334 can use information indicating bed presence and sleep states for the user 308 collected over a period of time to identify a sleep pattern for the user. For example, the control circuitry 334 can identify that the user 308 generally goes to bed between 9:30 pm and 10:00 pm, generally falls asleep between 10:00 pm and 11:00 pm, and generally wakes up between 6:30 am and 6:45 am based on information indicating user presence and biometrics for the user 308 collected over a week. The control circuitry 334 can use identified patterns for a user to better process and identify user interactions with the bed 302 by the user 308.

For example, given the above example user bed presence, sleep, and wake patterns for the user 308, if the user 308 is detected as being on the bed at 3:00 pm, the control circuitry 334 can determine that the user's presence on the bed is only temporary, and use this determination to generate different control signals than would be generated if the control circuitry 334 determined that the user 308 was in bed for the evening. As another example, if the control circuitry 334 detects that the user 308 has gotten out of bed at 3:00 am, the control circuitry 334 can use identified patterns for the user 308 to determine that the user has only gotten up temporarily (for example, to use the rest room, or get a glass of water) and is not up for the day. By contrast, if the control circuitry 334 identifies that the user 308 has gotten out of the bed 302 at 6:40 am, the control circuitry 334 can determine that the user is up for the day and generate a different set of control signals than those that would be generated if it were determined that the user 308 were only getting out of bed temporarily (as would be the case when the user 308 gets out of the bed 302 at 3:00 am). For other users 308, getting out of the bed 302 at 3:00 am can be the normal wake-up time, which the control circuitry 334 can learn and respond to accordingly.

As described above, the control circuitry 334 for the bed 302 can generate control signals for control functions of various other devices. The control signals can be generated, at least in part, based on detected interactions by the user 308 with the bed 302, as well as other information including time, date, temperature, etc. For example, the control circuitry 334 can communicate with the television 312, receive information from the television 312, and generate control signals for controlling functions of the television 312. For example, the control circuitry 334 can receive an indication from the television 312 that the television 312 is currently on. If the television 312 is located in a different room from the bed 302, the control circuitry 334 can generate a control signal to turn the television 312 off upon making a determination that the user 308 has gone to bed for the evening. For example, if bed presence of the user 308 on the bed 302 is detected during a particular time range (e.g., between 8:00 pm and 7:00 am) and persists for longer than a threshold period of time (e.g., 10 minutes) the control circuitry 334 can use this information to determine that the user 308 is in bed for the evening. If the television 312 is on (as indicated by communications received by the control circuitry 334 of the bed 302 from the television 312) the control circuitry 334 can generate a control signal to turn the television 312 off. The control signals can then be transmitted to the television (e.g., through a directed communication link between the television 312 and the control circuitry 334 or through a network). As another example, rather than turning off the television 312 in response to detection of user bed presence, the control circuitry 334 can generate a control signal that causes the volume of the television 312 to be lowered by a pre-specified amount.

As another example, upon detecting that the user 308 has left the bed 302 during a specified time range (e.g., between 6:00 am and 8:00 am) the control circuitry 334 can generate control signals to cause the television 312 to turn on and tune to a pre-specified channel (e.g., the user 308 has indicated a preference for watching the morning news upon getting out of bed in the morning). The control circuitry 334 can generate the control signal and transmit the signal to the television 312 to cause the television 312 to turn on and tune to the desired station (which could be stored at the control circuitry 334, the television 312, or another location). As another example, upon detecting that the user 308 has gotten up for the day, the control circuitry 334 can generate and transmit control signals to cause the television 312 to turn on and begin playing a previously recorded program from a digital video recorder (DVR) in communication with the television 312.

As another example, if the television 312 is in the same room as the bed 302, the control circuitry 334 does not cause the television 312 to turn off in response to detection of user bed presence. Rather, the control circuitry 334 can generate and transmit control signals to cause the television 312 to turn off in response to determining that the user 308 is asleep. For example, the control circuitry 334 can monitor biometric signals of the user 308 (e.g., motion, heart rate, respiration rate) to determine that the user 308 has fallen asleep. Upon detecting that the user 308 is sleeping, the control circuitry 334 generates and transmits a control signal to turn the television 312 off. As another example, the control circuitry 334 can generate the control signal to turn off the television 312 after a threshold period of time after the user 308 has fallen asleep (e.g., 10 minutes after the user has fallen asleep). As another example, the control circuitry 334 generates control signals to lower the volume of the television 312 after determining that the user 308 is asleep. As yet another example, the control circuitry 334 generates and transmits a control signal to cause the television to gradually lower in volume over a period of time and then turn off in response to determining that the user 308 is asleep.

In some implementations, the control circuitry 334 can similarly interact with other media devices, such as computers, tablets, smart phones, stereo systems, etc. For example, upon detecting that the user 308 is asleep, the control circuitry 334 can generate and transmit a control signal to the user device 310 to cause the user device 310 to turn off, or turn down the volume on a video or audio file being played by the user device 310.

The control circuitry 334 can additionally communicate with the lighting system 314, receive information from the lighting system 314, and generate control signals for controlling functions of the lighting system 314. For example, upon detecting user bed presence on the bed 302 during a certain time frame (e.g., between 8:00 pm and 7:00 am) that lasts for longer than a threshold period of time (e.g., 10 minutes) the control circuitry 334 of the bed 302 can determine that the user 308 is in bed for the evening. In response to this determination, the control circuitry 334 can generate control signals to cause lights in one or more rooms other than the room in which the bed 302 is located to switch off. The control signals can then be transmitted to the lighting system 314 and executed by the lighting system 314 to cause the lights in the indicated rooms to shut off. For example, the control circuitry 334 can generate and transmit control signals to turn off lights in all common rooms, but not in other bedrooms. As another example, the control signals generated by the control circuitry 334 can indicate that lights in all rooms other than the room in which the bed 302 is located are to be turned off, while one or more lights located outside of the house containing the bed 302 are to be turned on, in response to determining that the user 308 is in bed for the evening. Additionally, the control circuitry 334 can generate and transmit control signals to cause the nightlight 328 to turn on in response to determining user 308 bed presence or whether the user 308 is asleep. As another example, the control circuitry 334 can generate first control signals for turning off a first set of lights (e.g., lights in common rooms) in response to detecting user bed presence, and second control signals for turning off a second set of lights (e.g., lights in the room in which the bed 302 is located) in response to detecting that the user 308 is asleep.

In some implementations, in response to determining that the user 308 is in bed for the evening, the control circuitry 334 of the bed 302 can generate control signals to cause the lighting system 314 to implement a sunset lighting scheme in the room in which the bed 302 is located. A sunset lighting scheme can include, for example, dimming the lights (either gradually over time, or all at once) in combination with changing the color of the light in the bedroom environment, such as adding an amber hue to the lighting in the bedroom. The sunset lighting scheme can help to put the user 308 to sleep when the control circuitry 334 has determined that the user 308 is in bed for the evening.

The control circuitry 334 can also be configured to implement a sunrise lighting scheme when the user 308 wakes up in the morning. The control circuitry 334 can determine that the user 308 is awake for the day, for example, by detecting that the user 308 has gotten off of the bed 302 (i.e., is no longer present on the bed 302) during a specified time frame (e.g., between 6:00 am and 8:00 am). As another example, the control circuitry 334 can monitor movement, heart rate, respiratory rate, or other biometric signals of the user 308 to determine that the user 308 is awake even though the user 308 has not gotten out of bed. If the control circuitry 334 detects that the user is awake during a specified time frame, the control circuitry 334 can determine that the user 308 is awake for the day. The specified time frame can be, for example, based on previously recorded user bed presence information collected over a period of time (e.g., two weeks) that indicates that the user 308 usually wakes up for the day between 6:30 am and 7:30 am. In response to the control circuitry 334 determining that the user 308 is awake, the control circuitry 334 can generate control signals to cause the lighting system 314 to implement the sunrise lighting scheme in the bedroom in which the bed 302 is located. The sunrise lighting scheme can include, for example, turning on lights (e.g., the lamp 326, or other lights in the bedroom). The sunrise lighting scheme can further include gradually increasing the level of light in the room where the bed 302 is located (or in one or more other rooms). The sunrise lighting scheme can also include only turning on lights of specified colors. For example, the sunrise lighting scheme can include lighting the bedroom with blue light to gently assist the user 308 in waking up and becoming active.

In some implementations, the control circuitry 334 can generate different control signals for controlling actions of one or more components, such as the lighting system 314, depending on a time of day that user interactions with the bed 302 are detected. For example, the control circuitry 334 can use historical user interaction information for interactions between the user 308 and the bed 302 to determine that the user 308 usually falls asleep between 10:00 pm and 11:00 pm and usually wakes up between 6:30 am and 7:30 am on weekdays. The control circuitry 334 can use this information to generate a first set of control signals for controlling the lighting system 314 if the user 308 is detected as getting out of bed at 3:00 am and to generate a second set of control signals for controlling the lighting system 314 if the user 308 is detected as getting out of bed after 6:30 am. For example, if the user 308 gets out of bed prior to 6:30 am, the control circuitry 334 can turn on lights that guide the user 308's route to a restroom. As another example, if the user 308 gets out of bed prior to 6:30 am, the control circuitry 334 can turn on lights that guide the user 308's route to the kitchen (which can include, for example, turning on the nightlight 328, turning on under bed lighting, or turning on the lamp 326).

As another example, if the user 308 gets out of bed after 6:30 am, the control circuitry 334 can generate control signals to cause the lighting system 314 to initiate a sunrise lighting scheme, or to turn on one or more lights in the bedroom and/or other rooms. In some implementations, if the user 308 is detected as getting out of bed prior to a specified morning rise time for the user 308, the control circuitry 334 causes the lighting system 314 to turn on lights that are dimmer than lights that are turned on by the lighting system 314 if the user 308 is detected as getting out of bed after the specified morning rise time. Causing the lighting system 314 to only turn on dim lights when the user 308 gets out of bed during the night (i.e., prior to normal rise time for the user 308) can prevent other occupants of the house from being woken by the lights while still allowing the user 308 to see in order to reach the restroom, kitchen, or another destination within the house.

The historical user interaction information for interactions between the user 308 and the bed 302 can be used to identify user sleep and awake time frames. For example, user bed presence times and sleep times can be determined for a set period of time (e.g., two weeks, a month, etc.). The control circuitry 334 can then identify a typical time range or time frame in which the user 308 goes to bed, a typical time frame for when the user 308 falls asleep, and a typical time frame for when the user 308 wakes up (and in some cases, different time frames for when the user 308 wakes up and when the user 308 actually gets out of bed). In some implementations, buffer time can be added to these time frames. For example, if the user is identified as typically going to bed between 10:00 pm and 10:30 pm, a buffer of a half hour in each direction can be added to the time frame such that any detection of the user getting onto the bed between 9:30 pm and 11:00 pm is interpreted as the user 308 going to bed for the evening. As another example, detection of bed presence of the user 308 starting from a half hour before the earliest typical time that the user 308 goes to bed extending until the typical wake up time (e.g., 6:30 am) for the user can be interpreted as the user going to bed for the evening. For example, if the user typically goes to bed between 10:00 pm and 10:30 pm, if the user's bed presence is sensed at 12:30 am one night, that can be interpreted as the user getting into bed for the evening even though this is outside of the user's typical time frame for going to bed because it has occurred prior to the user's normal wake up time. In some implementations, different time frames are identified for different times of the year (e.g., earlier bed time during winter vs. summer) or at different times of the week (e.g., user wakes up earlier on weekdays than on weekends).

The control circuitry 334 can distinguish between the user 308 going to bed for an extended period (such as for the night) as opposed to being present on the bed 302 for a shorter period (such as for a nap) by sensing duration of presence of the user 308. In some examples, the control circuitry 334 can distinguish between the user 308 going to bed for an extended period (such as for the night) as opposed to going to bed for a shorter period (such as for a nap) by sensing duration of sleep of the user 308. For example, the control circuitry 334 can set a time threshold whereby if the user 308 is sensed on the bed 302 for longer than the threshold, the user 308 is considered to have gone to bed for the night. In some examples, the threshold can be about 2 hours, whereby if the user 308 is sensed on the bed 302 for greater than 2 hours, the control circuitry 334 registers that as an extended sleep event. In other examples, the threshold can be greater than or less than two hours.

The control circuitry 334 can detect repeated extended sleep events to determine a typical bed time range of the user 308 automatically, without requiring the user 308 to enter a bed time range. This can allow the control circuitry 334 to accurately estimate when the user 308 is likely to go to bed for an extended sleep event, regardless of whether the user 308 typically goes to bed using a traditional sleep schedule or a non-traditional sleep schedule. The control circuitry 334 can then use knowledge of the bed time range of the user 308 to control one or more components (including components of the bed 302 and/or non-bed peripherals) differently based on sensing bed presence during the bed time range or outside of the bed time range.

In some examples, the control circuitry 334 can automatically determine the bed time range of the user 308 without requiring user inputs. In some examples, the control circuitry 334 can determine the bed time range of the user 308 automatically and in combination with user inputs. In some examples, the control circuitry 334 can set the bed time range directly according to user inputs. In some examples, the control circuitry 334 can associate different bed times with different days of the week. In each of these examples, the control circuitry 334 can control one or more components (such as the lighting system 314, the thermostat 316, the security system 318, the oven 322, the coffee maker 324, the lamp 326, and the nightlight 328), as a function of sensed bed presence and the bed time range.

The control circuitry 334 can additionally communicate with the thermostat 316, receive information from the thermostat 316, and generate control signals for controlling functions of the thermostat 316. For example, the user 308 can indicate user preferences for different temperatures at different times, depending on the sleep state or bed presence of the user 308. For example, the user 308 may prefer an environmental temperature of 72 degrees when out of bed, 70 degrees when in bed but awake, and 68 degrees when sleeping. The control circuitry 334 of the bed 302 can detect bed presence of the user 308 in the evening and determine that the user 308 is in bed for the night. In response to this determination, the control circuitry 334 can generate control signals to cause the thermostat to change the temperature to 70 degrees. The control circuitry 334 can then transmit the control signals to the thermostat 316. Upon detecting that the user 308 is in bed during the bed time range or asleep, the control circuitry 334 can generate and transmit control signals to cause the thermostat 316 to change the temperature to 68. The next morning, upon determining that the user is awake for the day (e.g., the user 308 gets out of bed after 6:30 am) the control circuitry 334 can generate and transmit control circuitry 334 to cause the thermostat to change the temperature to 72 degrees.

In some implementations, the control circuitry 334 can similarly generate control signals to cause one or more heating or cooling elements on the surface of the bed 302 to change temperature at various times, either in response to user interaction with the bed 302 or at various pre-programmed times. For example, the control circuitry 334 can activate a heating element to raise the temperature of one side of the surface of the bed 302 to 73 degrees when it is detected that the user 308 has fallen asleep. As another example, upon determining that the user 308 is up for the day, the control circuitry 334 can turn off a heating or cooling element. As yet another example, the user 308 can pre-program various times at which the temperature at the surface of the bed should be raised or lowered. For example, the user can program the bed 302 to raise the surface temperature to 76 degrees at 10:00 pm, and lower the surface temperature to 68 degrees at 11:30 pm.

In some implementations, in response to detecting user bed presence of the user 308 and/or that the user 308 is asleep, the control circuitry 334 can cause the thermostat 316 to change the temperature in different rooms to different values. For example, in response to determining that the user 308 is in bed for the evening, the control circuitry 334 can generate and transmit control signals to cause the thermostat 316 to set the temperature in one or more bedrooms of the house to 72 degrees and set the temperature in other rooms to 67 degrees.

The control circuitry 334 can also receive temperature information from the thermostat 316 and use this temperature information to control functions of the bed 302 or other devices. For example, as discussed above, the control circuitry 334 can adjust temperatures of heating elements included in the bed 302 in response to temperature information received from the thermostat 316.

In some implementations, the control circuitry 334 can generate and transmit control signals for controlling other temperature control systems. For example, in response to determining that the user 308 is awake for the day, the control circuitry 334 can generate and transmit control signals for causing floor heating elements to activate. For example, the control circuitry 334 can cause a floor heating system for a master bedroom to turn on in response to determining that the user 308 is awake for the day.

The control circuitry 334 can additionally communicate with the security system 318, receive information from the security system 318, and generate control signals for controlling functions of the security system 318. For example, in response to detecting that the user 308 in is bed for the evening, the control circuitry 334 can generate control signals to cause the security system to engage or disengage security functions. The control circuitry 334 can then transmit the control signals to the security system 318 to cause the security system 318 to engage. As another example, the control circuitry 334 can generate and transmit control signals to cause the security system 318 to disable in response to determining that the user 308 is awake for the day (e.g., user 308 is no longer present on the bed 302 after 6:00 am). In some implementations, the control circuitry 334 can generate and transmit a first set of control signals to cause the security system 318 to engage a first set of security features in response to detecting user bed presence of the user 308, and can generate and transmit a second set of control signals to cause the security system 318 to engage a second set of security features in response to detecting that the user 308 has fallen asleep.

In some implementations, the control circuitry 334 can receive alerts from the security system 318 (and/or a cloud service associated with the security system 318) and indicate the alert to the user 308. For example, the control circuitry 334 can detect that the user 308 is in bed for the evening and in response, generate and transmit control signals to cause the security system 318 to engage or disengage. The security system can then detect a security breach (e.g., someone has opened the door 332 without entering the security code, or someone has opened a window when the security system 318 is engaged). The security system 318 can communicate the security breach to the control circuitry 334 of the bed 302. In response to receiving the communication from the security system 318, the control circuitry 334 can generate control signals to alert the user 308 to the security breach. For example, the control circuitry 334 can cause the bed 302 to vibrate. As another example, the control circuitry 334 can cause portions of the bed 302 to articulate (e.g., cause the head section to raise or lower) in order to wake the user 308 and alert the user to the security breach. As another example, the control circuitry 334 can generate and transmit control signals to cause the lamp 326 to flash on and off at regular intervals to alert the user 308 to the security breach. As another example, the control circuitry 334 can alert the user 308 of one bed 302 regarding a security breach in a bedroom of another bed, such as an open window in a kid's bedroom. As another example, the control circuitry 334 can send an alert to a garage door controller (e.g., to close and lock the door). As another example, the control circuitry 334 can send an alert for the security to be disengaged.

The control circuitry 334 can additionally generate and transmit control signals for controlling the garage door 320 and receive information indicating a state of the garage door 320 (i.e., open or closed). For example, in response to determining that the user 308 is in bed for the evening, the control circuitry 334 can generate and transmit a request to a garage door opener or another device capable of sensing if the garage door 320 is open. The control circuitry 334 can request information on the current state of the garage door 320. If the control circuitry 334 receives a response (e.g., from the garage door opener) indicating that the garage door 320 is open, the control circuitry 334 can either notify the user 308 that the garage door is open, or generate a control signal to cause the garage door opener to close the garage door 320. For example, the control circuitry 334 can send a message to the user device 310 indicating that the garage door is open. As another example, the control circuitry 334 can cause the bed 302 to vibrate. As yet another example, the control circuitry 334 can generate and transmit a control signal to cause the lighting system 314 to cause one or more lights in the bedroom to flash to alert the user 308 to check the user device 310 for an alert (in this example, an alert regarding the garage door 320 being open). Alternatively, or additionally, the control circuitry 334 can generate and transmit control signals to cause the garage door opener to close the garage door 320 in response to identifying that the user 308 is in bed for the evening and that the garage door 320 is open. In some implementations, control signals can vary depend on the age of the user 308.

The control circuitry 334 can similarly send and receive communications for controlling or receiving state information associated with the door 332 or the oven 322. For example, upon detecting that the user 308 is in bed for the evening, the control circuitry 334 can generate and transmit a request to a device or system for detecting a state of the door 332. Information returned in response to the request can indicate various states for the door 332 such as open, closed but unlocked, or closed and locked. If the door 332 is open or closed but unlocked, the control circuitry 334 can alert the user 308 to the state of the door, such as in a manner described above with reference to the garage door 320. Alternatively, or in addition to alerting the user 308, the control circuitry 334 can generate and transmit control signals to cause the door 332 to lock, or to close and lock. If the door 332 is closed and locked, the control circuitry 334 can determine that no further action is needed.

Similarly, upon detecting that the user 308 is in bed for the evening, the control circuitry 334 can generate and transmit a request to the oven 322 to request a state of the oven 322 (e.g., on or off). If the oven 322 is on, the control circuitry 334 can alert the user 308 and/or generate and transmit control signals to cause the oven 322 to turn off. If the oven is already off, the control circuitry 334 can determine that no further action is necessary. In some implementations, different alerts can be generated for different events. For example, the control circuitry 334 can cause the lamp 326 (or one or more other lights, via the lighting system 314) to flash in a first pattern if the security system 318 has detected a breach, flash in a second pattern if garage door 320 is on, flash in a third pattern if the door 332 is open, flash in a fourth pattern if the oven 322 is on, and flash in a fifth pattern if another bed has detected that a user of that bed has gotten up (e.g., that a child of the user 308 has gotten out of bed in the middle of the night as sensed by a sensor in the bed 302 of the child). Other examples of alerts that can be processed by the control circuitry 334 of the bed 302 and communicated to the user include a smoke detector detecting smoke (and communicating this detection of smoke to the control circuitry 334), a carbon monoxide tester detecting carbon monoxide, a heater malfunctioning, or an alert from any other device capable of communicating with the control circuitry 334 and detecting an occurrence that should be brought to the user 308's attention.

The control circuitry 334 can also communicate with a system or device for controlling a state of the window blinds 330. For example, in response to determining that the user 308 is in bed for the evening, the control circuitry 334 can generate and transmit control signals to cause the window blinds 330 to close. As another example, in response to determining that the user 308 is up for the day (e.g., user has gotten out of bed after 6:30 am) the control circuitry 334 can generate and transmit control signals to cause the window blinds 330 to open. By contrast, if the user 308 gets out of bed prior to a normal rise time for the user 308, the control circuitry 334 can determine that the user 308 is not awake for the day and does not generate control signals for causing the window blinds 330 to open. As yet another example, the control circuitry 334 can generate and transmit control signals that cause a first set of blinds to close in response to detecting user bed presence of the user 308 and a second set of blinds to close in response to detecting that the user 308 is asleep.

The control circuitry 334 can generate and transmit control signals for controlling functions of other household devices in response to detecting user interactions with the bed 302. For example, in response to determining that the user 308 is awake for the day, the control circuitry 334 can generate and transmit control signals to the coffee maker 324 to cause the coffee maker 324 to begin brewing coffee. As another example, the control circuitry 334 can generate and transmit control signals to the oven 322 to cause the oven to begin preheating (for users that like fresh baked bread in the morning). As another example, the control circuitry 334 can use information indicating that the user 308 is awake for the day along with information indicating that the time of year is currently winter and/or that the outside temperature is below a threshold value to generate and transmit control signals to cause a car engine block heater to turn on.

As another example, the control circuitry 334 can generate and transmit control signals to cause one or more devices to enter a sleep mode in response to detecting user bed presence of the user 308, or in response to detecting that the user 308 is asleep. For example, the control circuitry 334 can generate control signals to cause a mobile phone of the user 308 to switch into sleep mode. The control circuitry 334 can then transmit the control signals to the mobile phone. Later, upon determining that the user 308 is up for the day, the control circuitry 334 can generate and transmit control signals to cause the mobile phone to switch out of sleep mode.

In some implementations, the control circuitry 334 can communicate with one or more noise control devices. For example, upon determining that the user 308 is in bed for the evening, or that the user 308 is asleep, the control circuitry 334 can generate and transmit control signals to cause one or more noise cancelation devices to activate. The noise cancelation devices can, for example, be included as part of the bed 302 or located in the bedroom with the bed 302. As another example, upon determining that the user 308 is in bed for the evening or that the user 308 is asleep, the control circuitry 334 can generate and transmit control signals to turn the volume on, off, up, or down, for one or more sound generating devices, such as a stereo system radio, computer, tablet, etc.

Additionally, functions of the bed 302 are controlled by the control circuitry 334 in response to user interactions with the bed 302. For example, the bed 302 can include an adjustable foundation and an articulation controller configured to adjust the position of one or more portions of the bed 302 by adjusting the adjustable foundation that supports the bed. For example, the articulation controller can adjust the bed 302 from a flat position to a position in which a head portion of a mattress of the bed 302 is inclined upward (e.g., to facilitate a user sitting up in bed and/or watching television). In some implementations, the bed 302 includes multiple separately articulable sections. For example, portions of the bed corresponding to the locations of the air chambers 306*a* and 306*b* can be articulated independently from each other, to allow one person positioned on the bed 302 surface to rest in a first position (e.g., a flat position) while a second person rests in a second position (e.g., a reclining position with the head raised at an angle from the waist). In some implementations, separate positions can be set for two different beds (e.g., two twin beds placed next to each other). The foundation of the bed 302 can include more than one zone that can be independently adjusted. The articulation controller can also be configured to provide different levels of massage to one or more users on the bed 302 or to cause the bed to vibrate to communicate alerts to the user 308 as described above.

The control circuitry 334 can adjust positions (e.g., incline and decline positions for the user 308 and/or an additional user of the bed 302) in response to user interactions with the bed 302. For example, the control circuitry 334 can cause the articulation controller to adjust the bed 302 to a first recline position for the user 308 in response to sensing user bed presence for the user 308. The control circuitry 334 can cause the articulation controller to adjust the bed 302 to a second recline position (e.g., a less reclined, or flat position) in response to determining that the user 308 is asleep. As another example, the control circuitry 334 can receive a communication from the television 312 indicating that the user 308 has turned off the television 312, and in response the control circuitry 334 can cause the articulation controller to adjust the position of the bed 302 to a preferred user sleeping position (e.g., due to the user turning off the television 312 while the user 308 is in bed indicating that the user 308 wishes to go to sleep).

In some implementations, the control circuitry 334 can control the articulation controller so as to wake up one user of the bed 302 without waking another user of the bed 302. For example, the user 308 and a second user of the bed 302 can each set distinct wakeup times (e.g., 6:30 am and 7:15 am respectively). When the wakeup time for the user 308 is reached, the control circuitry 334 can cause the articulation controller to vibrate or change the position of only a side of the bed on which the user 308 is located to wake the user 308 without disturbing the second user. When the wakeup time for the second user is reached, the control circuitry 334 can cause the articulation controller to vibrate or change the position of only the side of the bed on which the second user is located. Alternatively, when the second wakeup time occurs, the control circuitry 334 can utilize other methods (such as audio alarms, or turning on the lights) to wake the second user since the user 308 is already awake and therefore will not be disturbed when the control circuitry 334 attempts to wake the second user.

Still referring to FIG. 3, the control circuitry 334 for the bed 302 can utilize information for interactions with the bed 302 by multiple users to generate control signals for controlling functions of various other devices. For example, the control circuitry 334 can wait to generate control signals for, for example, engaging the security system 318, or instructing the lighting system 314 to turn off lights in various rooms until both the user 308 and a second user are detected as being present on the bed 302. As another example, the control circuitry 334 can generate a first set of control signals to cause the lighting system 314 to turn off a first set of lights upon detecting bed presence of the user 308 and generate a second set of control signals for turning off a second set of lights in response to detecting bed presence of a second user. As another example, the control circuitry 334 can wait until it has been determined that both the user 308 and a second user are awake for the day before generating control signals to open the window blinds 330. As yet another example, in response to determining that the user 308 has left the bed and is awake for the day, but that a second user is still sleeping, the control circuitry 334 can generate and transmit a first set of control signals to cause the coffee maker 324 to begin brewing coffee, to cause the security system 318 to deactivate, to turn on the lamp 326, to turn off the nightlight 328, to cause the thermostat 316 to raise the temperature in one or more rooms to 72 degrees, and to open blinds (e.g., the window blinds 330) in rooms other than the bedroom in which the bed 302 is located. Later, in response to detecting that the second user is no longer present on the bed (or that the second user is awake) the control circuitry 334 can generate and transmit a second set of control signals to, for example, cause the lighting system 314 to turn on one or more lights in the bedroom, to cause window blinds in the bedroom to open, and to turn on the television 312 to a pre-specified channel.

Examples of Data Processing Systems Associated with a Bed

Described here are examples of systems and components that can be used for data processing tasks that are, for example, associated with a bed. In some cases, multiple examples of a particular component or group of components are presented. Some of these examples are redundant and/or mutually exclusive alternatives. Connections between components are shown as examples to illustrate possible network configurations for allowing communication between components. Different formats of connections can be used as technically needed or desired. The connections generally indicate a logical connection that can be created with any technologically feasible format. For example, a network on a motherboard can be created with a printed circuit board, wireless data connections, and/or other types of network connections. Some logical connections are not shown for clarity. For example, connections with power supplies and/or computer readable memory may not be shown for clarities sake, as many or all elements of a particular component may need to be connected to the power supplies and/or computer readable memory.

Figure 4A:
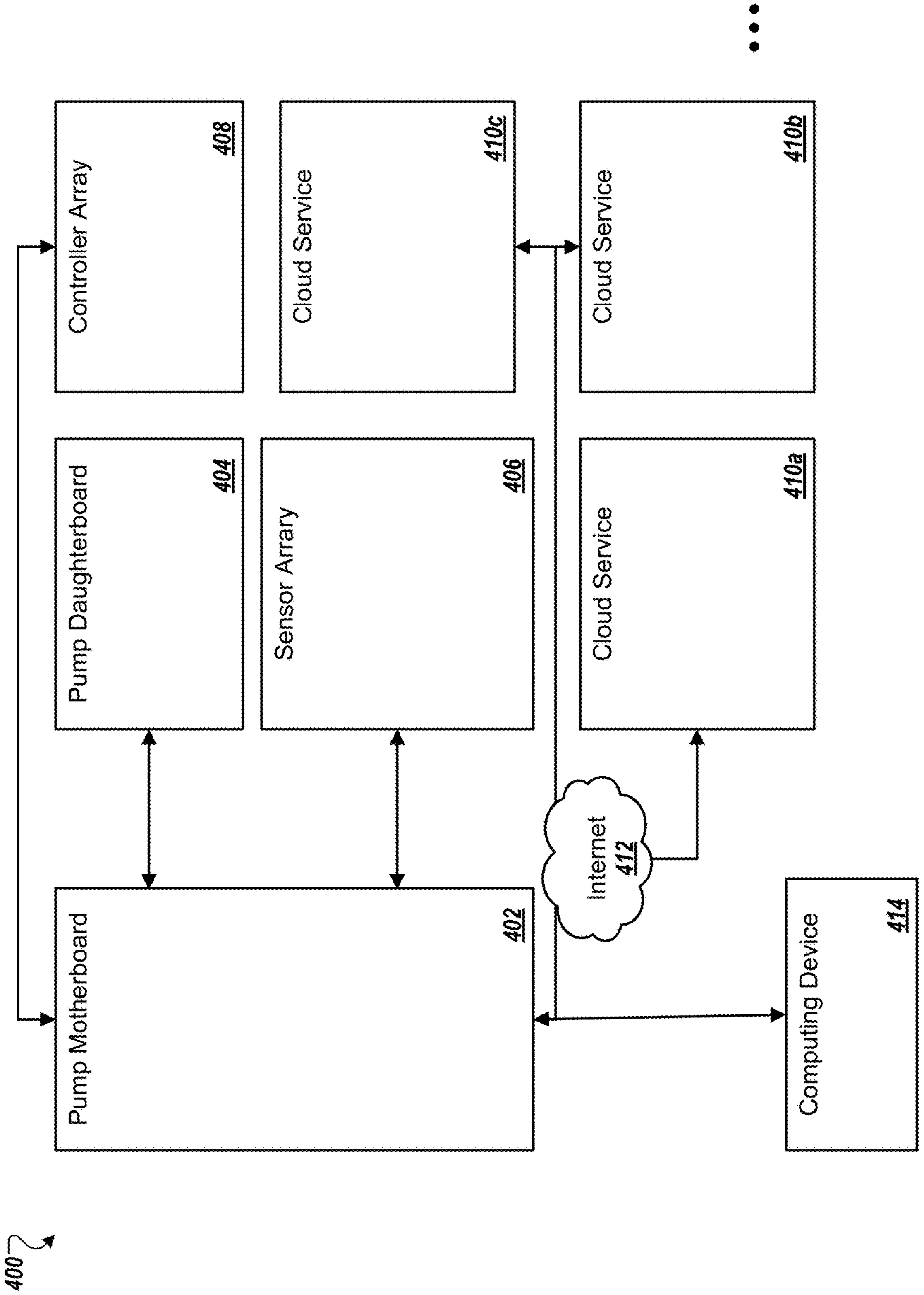
FIGS. 4A and 4B are block diagrams of example data processing systems that can be associated with a bed.

FIG. 4A is a block diagram of an example of a data processing system 400 that can be associated with a bed system, including those described above with respect to FIGS. 1-3. This system 400 includes a pump motherboard 402 and a pump daughterboard 404. The system 400 includes a sensor array 406 that can include one or more sensors configured to sense physical phenomenon of the environment and/or bed, and to report such sensing back to the pump motherboard 402 for, for example, analysis. The system 400 also includes a controller array 408 that can include one or more controllers configured to control logic-controlled devices of the bed and/or environment. The pump motherboard 400 can be in communication with one or more computing devices 414 and one or more cloud services 410 over local networks, the Internet 412, or otherwise as is technically appropriate. Each of these components will be described in more detail, some with multiple example configurations, below.

In this example, a pump motherboard 402 and a pump daughterboard 404 are communicably coupled. They can be conceptually described as a center or hub of the system 400, with the other components conceptually described as spokes of the system 400. In some configurations, this can mean that each of the spoke components communicates primarily or exclusively with the pump motherboard 402. For example, a sensor of the sensor array may not be configured to, or may not be able to, communicate directly with a corresponding controller. Instead, each spoke component can communicate with the motherboard 402. The sensor of the sensor array 406 can report a sensor reading to the motherboard 402, and the motherboard 402 can determine that, in response, a controller of the controller array 408 should adjust some parameters of a logic controlled device or otherwise modify a state of one or more peripheral devices. In one case, if the temperature of the bed is determined to be too hot, the pump motherboard 402 can determine that a temperature controller should cool the bed.

One advantage of a hub-and-spoke network configuration, sometimes also referred to as a star-shaped network, is a reduction in network traffic compared to, for example, a mesh network with dynamic routing. If a particular sensor generates a large, continuous stream of traffic, that traffic may only be transmitted over one spoke of the network to the motherboard 402. The motherboard 402 can, for example, marshal that data and condense it to a smaller data format for retransmission for storage in a cloud service 410. Additionally or alternatively, the motherboard 402 can generate a single, small, command message to be sent down a different spoke of the network in response to the large stream. For example, if the large stream of data is a pressure reading that is transmitted from the sensor array 406 a few times a second, the motherboard 402 can respond with a single command message to the controller array to increase the pressure in an air chamber. In this case, the single command message can be orders of magnitude smaller than the stream of pressure readings.

As another advantage, a hub-and-spoke network configuration can allow for an extensible network that can accommodate components being added, removed, failing, etc. This can allow, for example, more, fewer, or different sensors in the sensor array 406, controllers in the controller array 408, computing devices 414, and/or cloud services 410. For example, if a particular sensor fails or is deprecated by a newer version of the sensor, the system 400 can be configured such that only the motherboard 402 needs to be updated about the replacement sensor. This can allow, for example, product differentiation where the same motherboard 402 can support an entry level product with fewer sensors and controllers, a higher value product with more sensors and controllers, and customer personalization where a customer can add their own selected components to the system 400.

Additionally, a line of air bed products can use the system 400 with different components. In an application in which every air bed in the product line includes both a central logic unit and a pump, the motherboard 402 (and optionally the daughterboard 404) can be designed to fit within a single, universal housing. Then, for each upgrade of the product in the product line, additional sensors, controllers, cloud services, etc., can be added. Design, manufacturing, and testing time can be reduced by designing all products in a product line from this base, compared to a product line in which each product has a bespoke logic control system.

Each of the components discussed above can be realized in a wide variety of technologies and configurations. Below, some examples of each component will be further discussed.

In some alternatives, two or more of the components of the system 400 can be realized in a single alternative component; some components can be realized in multiple, separate components; and/or some functionality can be provided by different components.

Figure 4B:
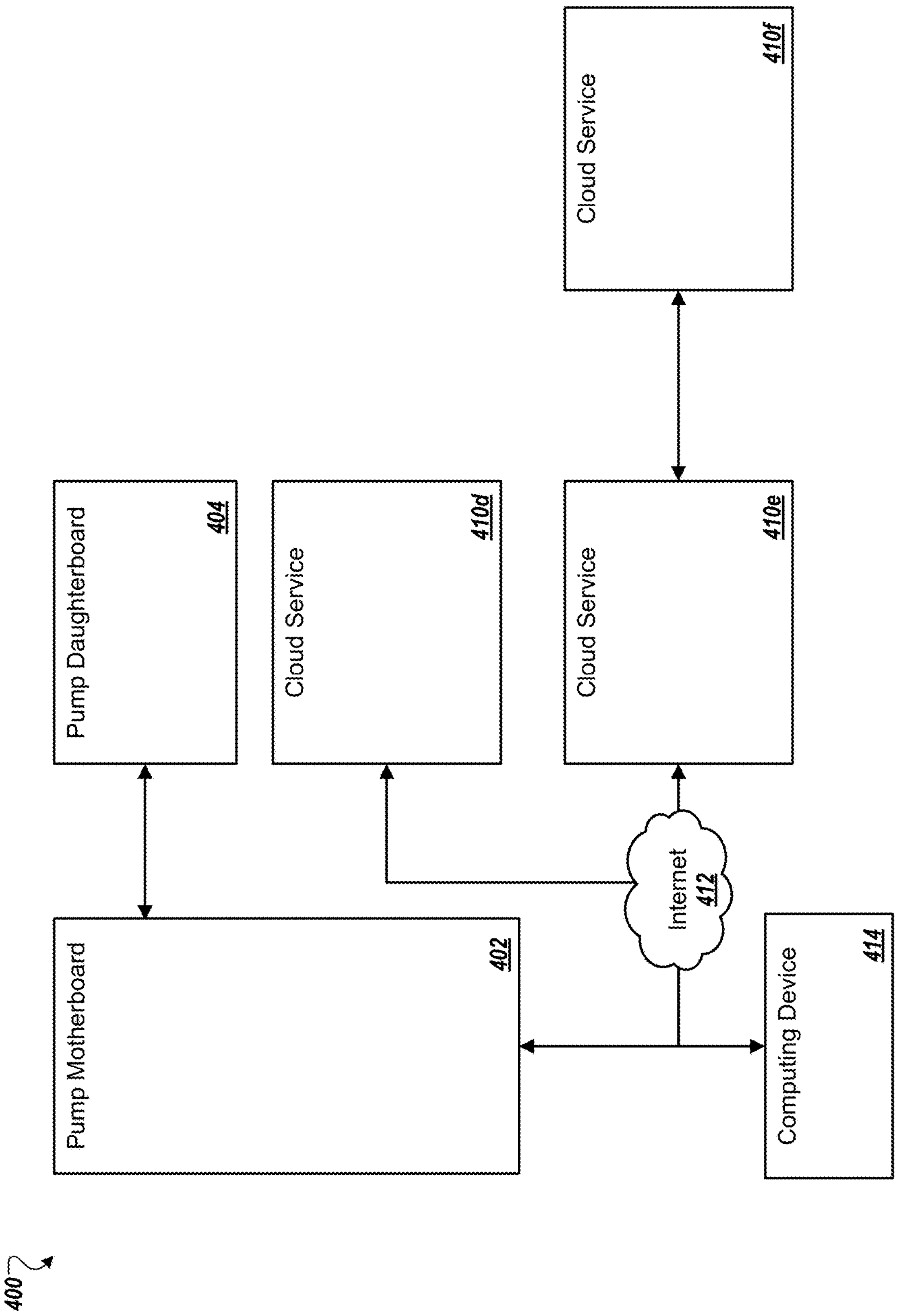

FIG. 4B is a block diagram showing some communication paths of the data processing system 400. As previously described, the motherboard 402 and the pump daughterboard 404 may act as a hub for peripheral devices and cloud services of the system 400. In cases in which the pump daughterboard 404 communicates with cloud services or other components, communications from the pump daughterboard 404 may be routed through the pump motherboard 402. This may allow, for example, the bed to have only a single connection with the internet 412. The computing device 414 may also have a connection to the internet 412, possibly through the same gateway used by the bed and/or possibly through a different gateway (e.g., a cell service provider).

Previously, a number of cloud services 410 were described. As shown in FIG. 4B, some cloud services, such as cloud services 410*d* and 410*e*, may be configured such that the pump motherboard 402 can communicate with the cloud service directly—that is the motherboard 402 may communicate with a cloud service 410 without having to use another cloud service 410 as an intermediary. Additionally or alternatively, some cloud services 410, for example cloud service 410*f*, may only be reachable by the pump motherboard 402 through an intermediary cloud service, for example cloud service 410*e*. While not shown here, some cloud services 410 may be reachable either directly or indirectly by the pump motherboard 402.

Additionally, some or all of the cloud services 410 may be configured to communicate with other cloud services. This communication may include the transfer of data and/or remote function calls according to any technologically appropriate format. For example, one cloud service 410 may request a copy for another cloud service's 410 data, for example, for purposes of backup, coordination, migration, or for performance of calculations or data mining. In another example, many cloud services 410 may contain data that is indexed according to specific users tracked by the user account cloud 410*c* and/or the bed data cloud 410*a*. These cloud services 410 may communicate with the user account cloud 410*c* and/or the bed data cloud 410*a* when accessing data specific to a particular user or bed.

Figure 5:
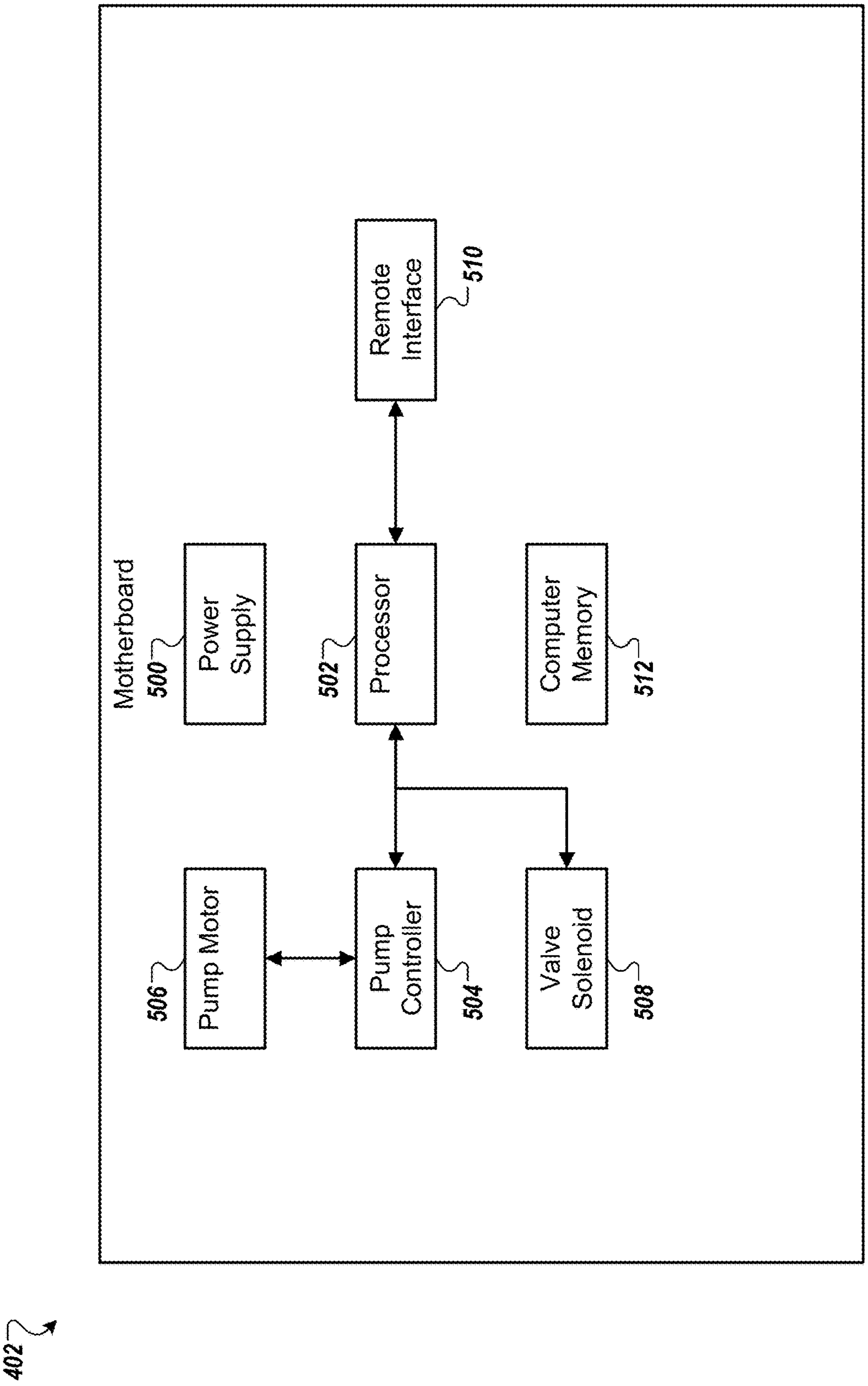
FIGS. 5 and 6 are block diagrams of examples of motherboards that can be used in a data processing system that can be associated with a bed.

FIG. 5 is a block diagram of an example of a motherboard 402 that can be used in a data processing system that can be associated with a bed system, including those described above with respect to FIGS. 1-3. In this example, compared to other examples described below, this motherboard 402 consists of relatively fewer parts and can be limited to provide a relatively limited feature set.

The motherboard includes a power supply 500, a processor 502, and computer memory 512. In general, the power supply includes hardware used to receive electrical power from an outside source and supply it to components of the motherboard 402. The power supply can include, for example, a battery pack and/or wall outlet adapter, an AC to DC converter, a DC to AC converter, a power conditioner, a capacitor bank, and/or one or more interfaces for providing power in the current type, voltage, etc., needed by other components of the motherboard 402.

The processor 502 is generally a device for receiving input, performing logical determinations, and providing output. The processor 502 can be a central processing unit, a microprocessor, general purpose logic circuitry, application-specific integrated circuitry, a combination of these, and/or other hardware for performing the functionality needed.

The memory 512 is generally one or more devices for storing data. The memory 512 can include long term stable data storage (e.g., on a hard disk), short term unstable (e.g., on Random Access Memory) or any other technologically appropriate configuration.

The motherboard 402 includes a pump controller 504 and a pump motor 506. The pump controller 504 can receive commands from the processor 502 and, in response, control the function of the pump motor 506. For example, the pump controller 504 can receive, from the processor 502, a command to increase the pressure of an air chamber by 0.3 pounds per square inch (PSI). The pump controller 504, in response, engages a valve so that the pump motor 506 is configured to pump air into the selected air chamber, and can engage the pump motor 506 for a length of time that corresponds to 0.3 PSI or until a sensor indicates that pressure has been increased by 0.3 PSI. In an alternative configuration, the message can specify that the chamber should be inflated to a target PSI, and the pump controller 504 can engage the pump motor 506 until the target PSI is reached.

A valve solenoid 508 can control which air chamber a pump is connected to. In some cases, the solenoid 508 can be controlled by the processor 502 directly. In some cases, the solenoid 508 can be controlled by the pump controller 504.

A remote interface 510 of the motherboard 402 can allow the motherboard 402 to communicate with other components of a data processing system. For example, the motherboard 402 can be able to communicate with one or more daughterboards, with peripheral sensors, and/or with peripheral controllers through the remote interface 510. The remote interface 510 can provide any technologically appropriate communication interface, including but not limited to multiple communication interfaces such as WiFi, Bluetooth, and copper wired networks.

Figure 6:
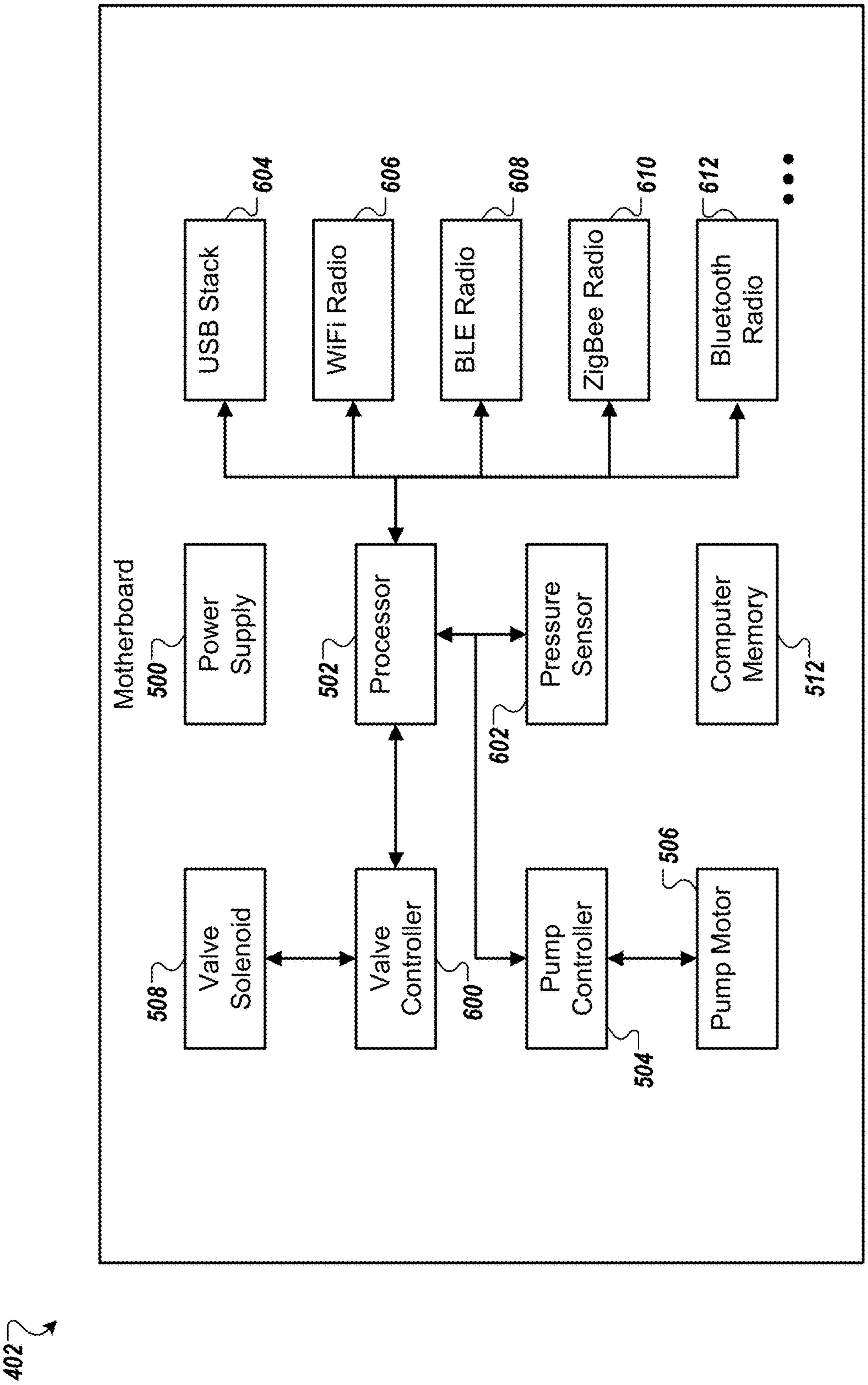

FIG. 6 is a block diagram of an example of a motherboard 402 that can be used in a data processing system that can be associated with a bed system, including those described above with respect to FIGS. 1-3. Compared to the motherboard 402 described with reference to FIG. 5, the motherboard in FIG. 6 can contain more components and provide more functionality in some applications.

In addition to the power supply 500, processor 502, pump controller 504, pump motor 506, and valve solenoid 508, this motherboard 402 is shown with a valve controller 600, a pressure sensor 602, a universal serial bus (USB) stack 604, a WiFi radio 606, a Bluetooth Low Energy (BLE) radio 608, a ZigBee radio 610, a Bluetooth radio 612 and a computer memory 512.

Similar to the way that the pump controller 504 converts commands from the processor 502 into control signals for the pump motor 506, the valve controller 600 can convert commands from the processor 502 into control signals for the valve solenoid 508. In one example, the processor 502 can issue a command to the valve controller 600 to connect the pump to a particular air chamber out of the group of air chambers in an air bed. The valve controller 600 can control the position of the valve solenoid 508 so that the pump is connected to the indicated air chamber.

The pressure sensor 602 can read pressure readings from one or more air chambers of the air bed. The pressure sensor 602 can also preform digital sensor conditioning.

The motherboard 402 can include a suite of network interfaces, including but not limited to those shown here. These network interfaces can allow the motherboard to communicate over a wired or wireless network with any number of devices, including but not limited to peripheral sensors, peripheral controllers, computing devices, and devices and services connected to the Internet 412.

Figure 7:
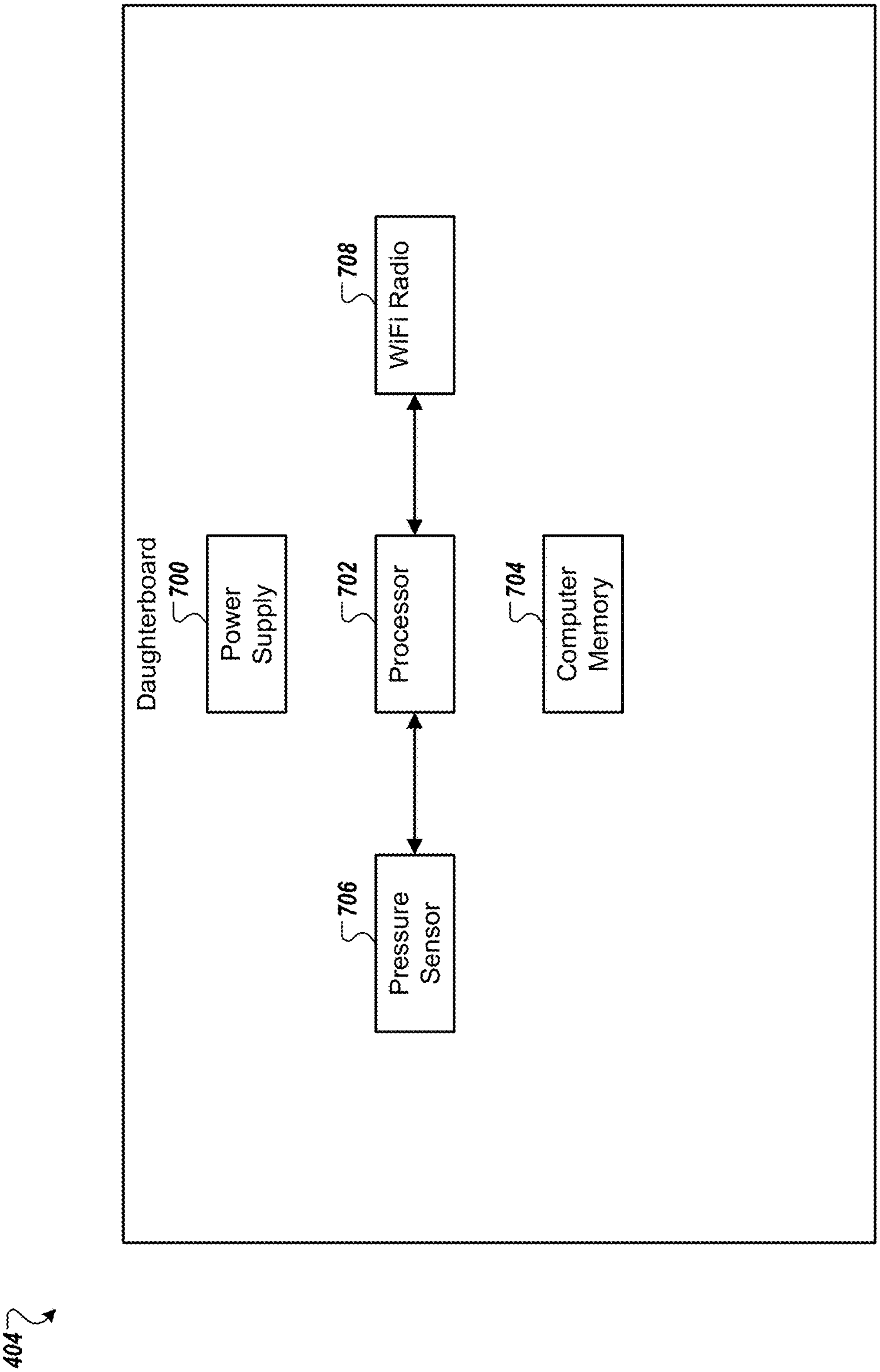
FIG. 7 is a block diagram of an example of a daughterboard that can be used in a data processing system that can be associated with a bed.

FIG. 7 is a block diagram of an example of a daughterboard 404 that can be used in a data processing system that can be associated with a bed system, including those described above with respect to FIGS. 1-3. In some configurations, one or more daughterboards 404 can be connected to the motherboard 402. Some daughterboards 404 can be designed to offload particular and/or compartmentalized tasks from the motherboard 402. This can be advantageous, for example, if the particular tasks are computationally intensive, proprietary, or subject to future revisions. For example, the daughterboard 404 can be used to calculate a particular sleep data metric. This metric can be computationally intensive, and calculating the sleep metric on the daughterboard 404 can free up the resources of the motherboard 402 while the metric is being calculated. Additionally and/or alternatively, the sleep metric can be subject to future revisions. To update the system 400 with the new sleep metric, it is possible that only the daughterboard 404 that calculates that metric need be replaced. In this case, the same motherboard 402 and other components can be used, saving the need to perform unit testing of additional components instead of just the daughterboard 404.

The daughterboard 404 is shown with a power supply 700, a processor 702, computer readable memory 704, a pressure sensor 706, and a WiFi radio 708. The processor can use the pressure sensor 706 to gather information about the pressure of the air chamber or chambers of an air bed. From this data, the processor 702 can perform an algorithm to calculate a sleep metric. In some examples, the sleep metric can be calculated from only the pressure of air chambers. In other examples, the sleep metric can be calculated from one or more other sensors. In an example in which different data is needed, the processor 702 can receive that data from an appropriate sensor or sensors. These sensors can be internal to the daughterboard 404, accessible via the WiFi radio 708, or otherwise in communication with the processor 702. Once the sleep metric is calculated, the processor 702 can report that sleep metric to, for example, the motherboard 402.

Figure 8:
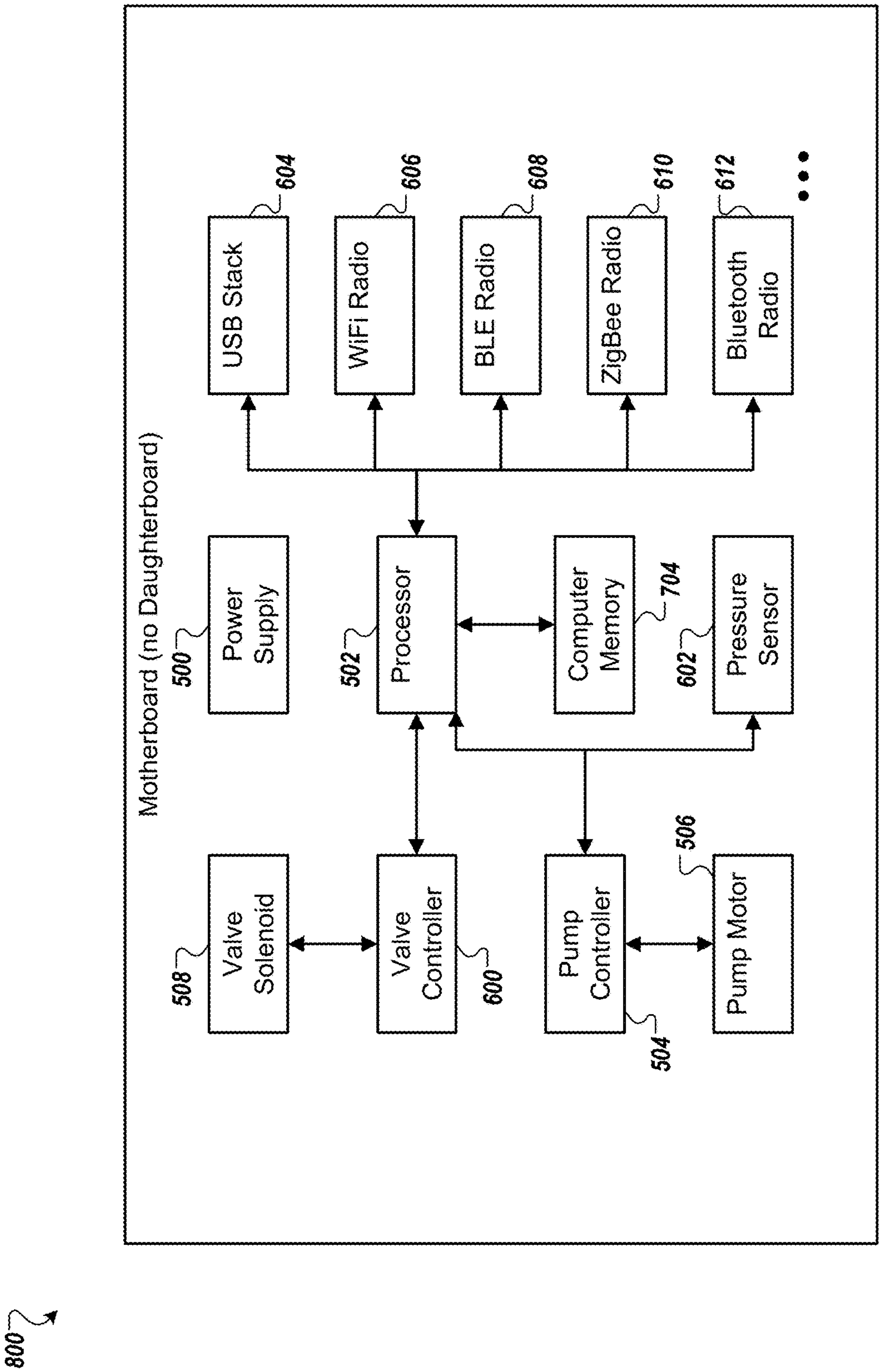
FIG. 8 is a block diagram of an example of a motherboard with no daughterboard that can be used in a data processing system that can be associated with a bed.

FIG. 8 is a block diagram of an example of a motherboard 800 with no daughterboard that can be used in a data processing system that can be associated with a bed system, including those described above with respect to FIGS. 1-3. In this example, the motherboard 800 can perform most, all, or more of the features described with reference to the motherboard 402 in FIG. 6 and the daughterboard 404 in FIG. 7.

Figure 9:
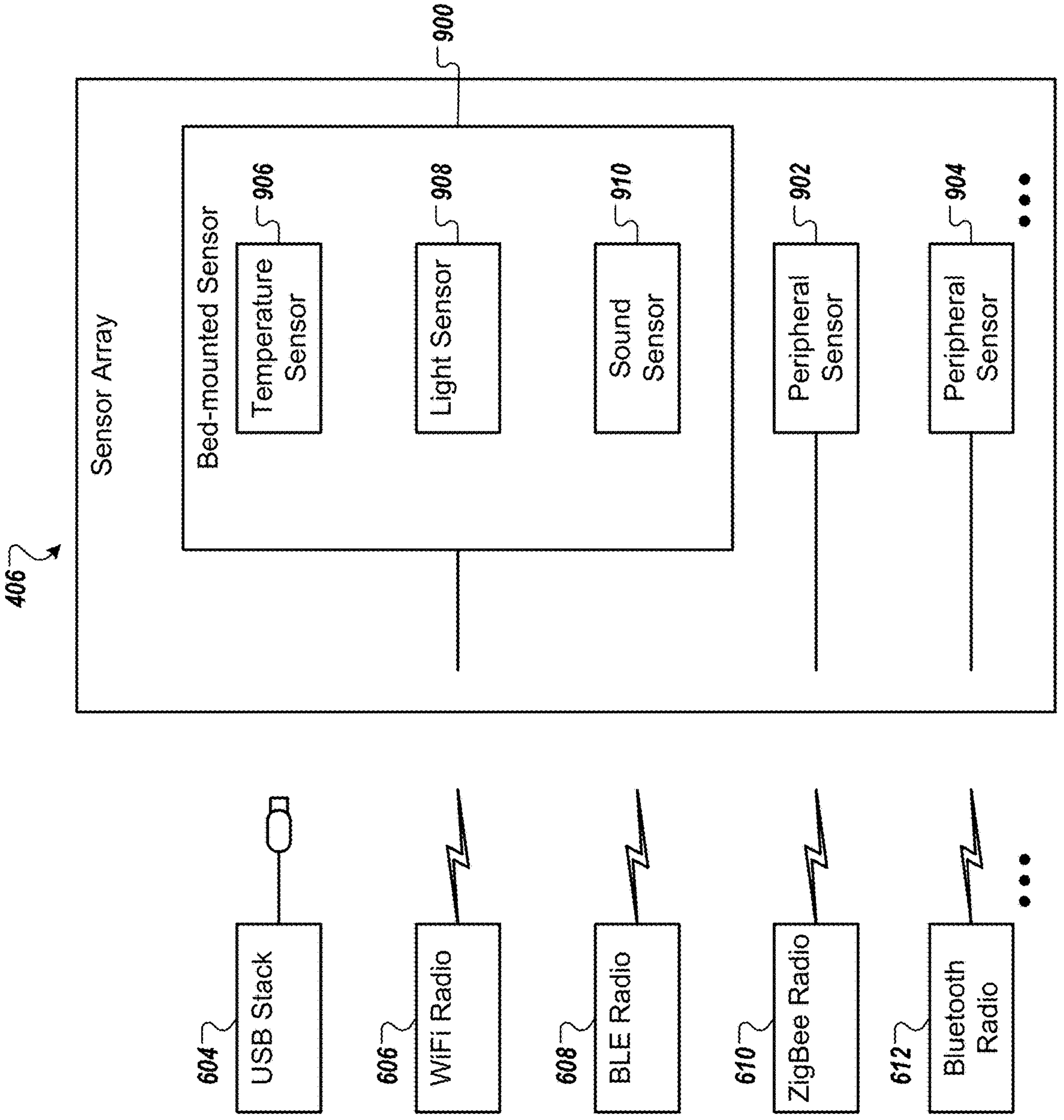
FIG. 9 is a block diagram of an example of a sensory array that can be used in a data processing system that can be associated with a bed.

FIG. 9 is a block diagram of an example of a sensory array 406 that can be used in a data processing system that can be associated with a bed system, including those described above with respect to FIGS. 1-3. In general, the sensor array 406 is a conceptual grouping of some or all the peripheral sensors that communicate with the motherboard 402 but are not native to the motherboard 402.

The peripheral sensors of the sensor array 406 can communicate with the motherboard 402 through one or more of the network interfaces of the motherboard, including but not limited to the USB stack 1112, a WiFi radio 606, a Bluetooth Low Energy (BLE) radio 608, a ZigBee radio 610, and a Bluetooth radio 612, as is appropriate for the configuration of the particular sensor. For example, a sensor that outputs a reading over a USB cable can communicate through the USB stack 1112.

Some of the peripheral sensors 900 of the sensor array 406 can be bed mounted 900. These sensors can be, for example, embedded into the structure of a bed and sold with the bed, or later affixed to the structure of the bed. Other peripheral sensors 902 and 904 can be in communication with the motherboard 402, but optionally not mounted to the bed. In some cases, some or all of the bed mounted sensors 900 and/or peripheral sensors 902 and 904 can share networking hardware, including a conduit that contains wires from each sensor, a multi-wire cable or plug that, when affixed to the motherboard 402, connect all of the associated sensors with the motherboard 402. In some embodiments, one, some, or all of sensors 902, 904, 906, 908, and 910 can sense one or more features of a mattress, such as pressure, temperature, light, sound, and/or one or more other features of the mattress. In some embodiments, one, some, or all of sensors 902, 904, 906, 908, and 910 can sense one or more features external to the mattress. In some embodiments, pressure sensor 902 can sense pressure of the mattress while some or all of sensors 902, 904, 906, 908, and 910 can sense one or more features of the mattress and/or external to the mattress.

Figure 10:
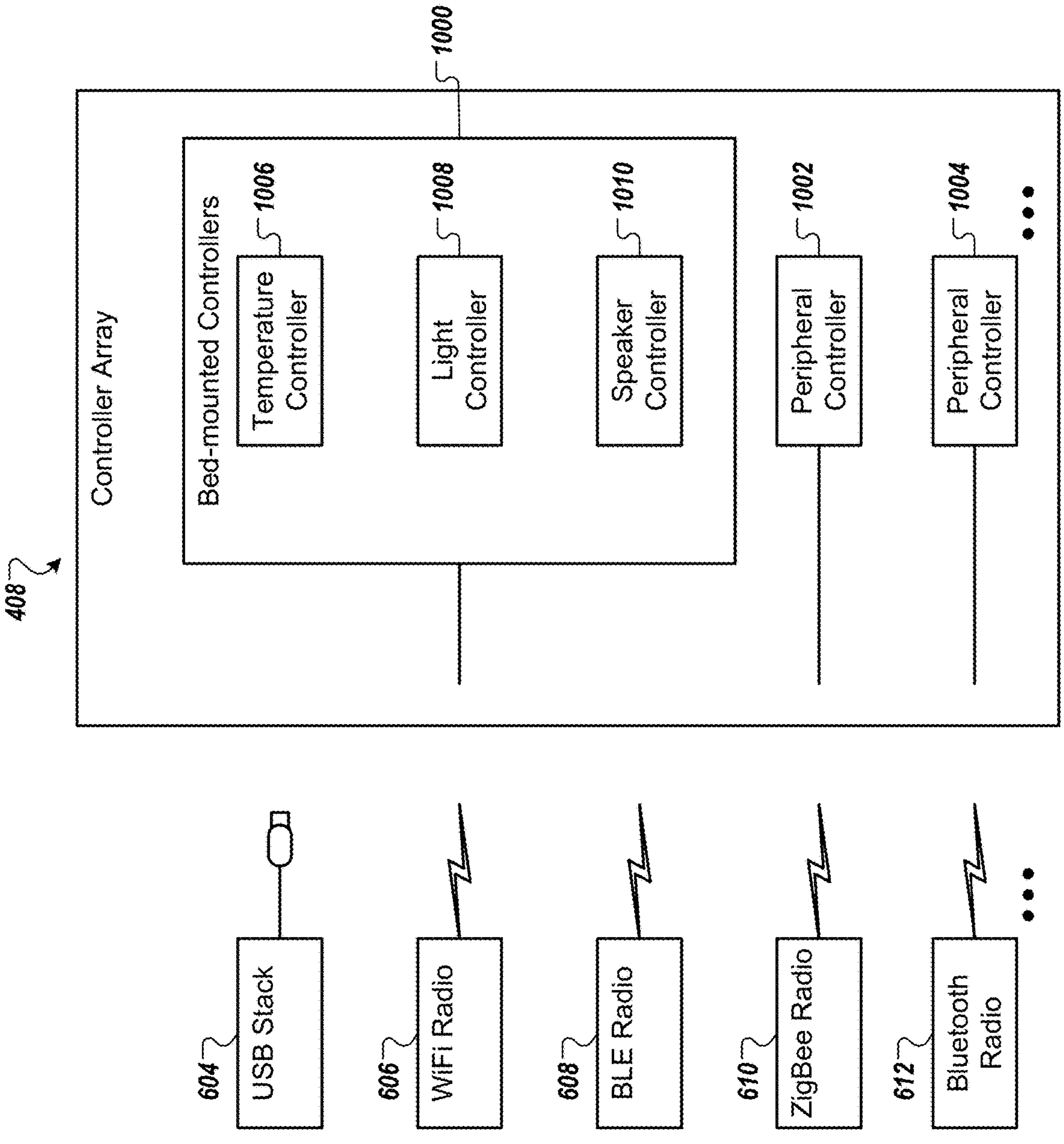
FIG. 10 is a block diagram of an example of a control array that can be used in a data processing system that can be associated with a bed.

FIG. 10 is a block diagram of an example of a controller array 408 that can be used in a data processing system that can be associated with a bed system, including those described above with respect to FIGS. 1-3. In general, the controller array 408 is a conceptual grouping of some or all peripheral controllers that communicate with the motherboard 402 but are not native to the motherboard 402.

The peripheral controllers of the controller array 408 can communicate with the motherboard 402 through one or more of the network interfaces of the motherboard, including but not limited to the USB stack 1112, a WiFi radio 1114, a Bluetooth Low Energy (BLE) radio 1116, a ZigBee radio 610, and a Bluetooth radio 612, as is appropriate for the configuration of the particular sensor. For example, a controller that receives a command over a USB cable can communicate through the USB stack 1112.

Some of the controllers of the controller array 408 can be bed mounted 1000, including but not limited to a temperature controller 1006, a light controller 1008, and/or a speaker controller 1010. These controllers can be, for example, embedded into the structure of a bed and sold with the bed, or later affixed to the structure of the bed. Other peripheral controllers 1002 and 1004 can be in communication with the motherboard 402, but optionally not mounted to the bed. In some cases, some or all of the bed mounted controllers 1000 and/or peripheral controllers 1002 and 1004 can share networking hardware, including a conduit that contains wires for each controller, a multi-wire cable or plug that, when affixed to the motherboard 402, connects all of the associated controllers with the motherboard 402.

Figure 11:
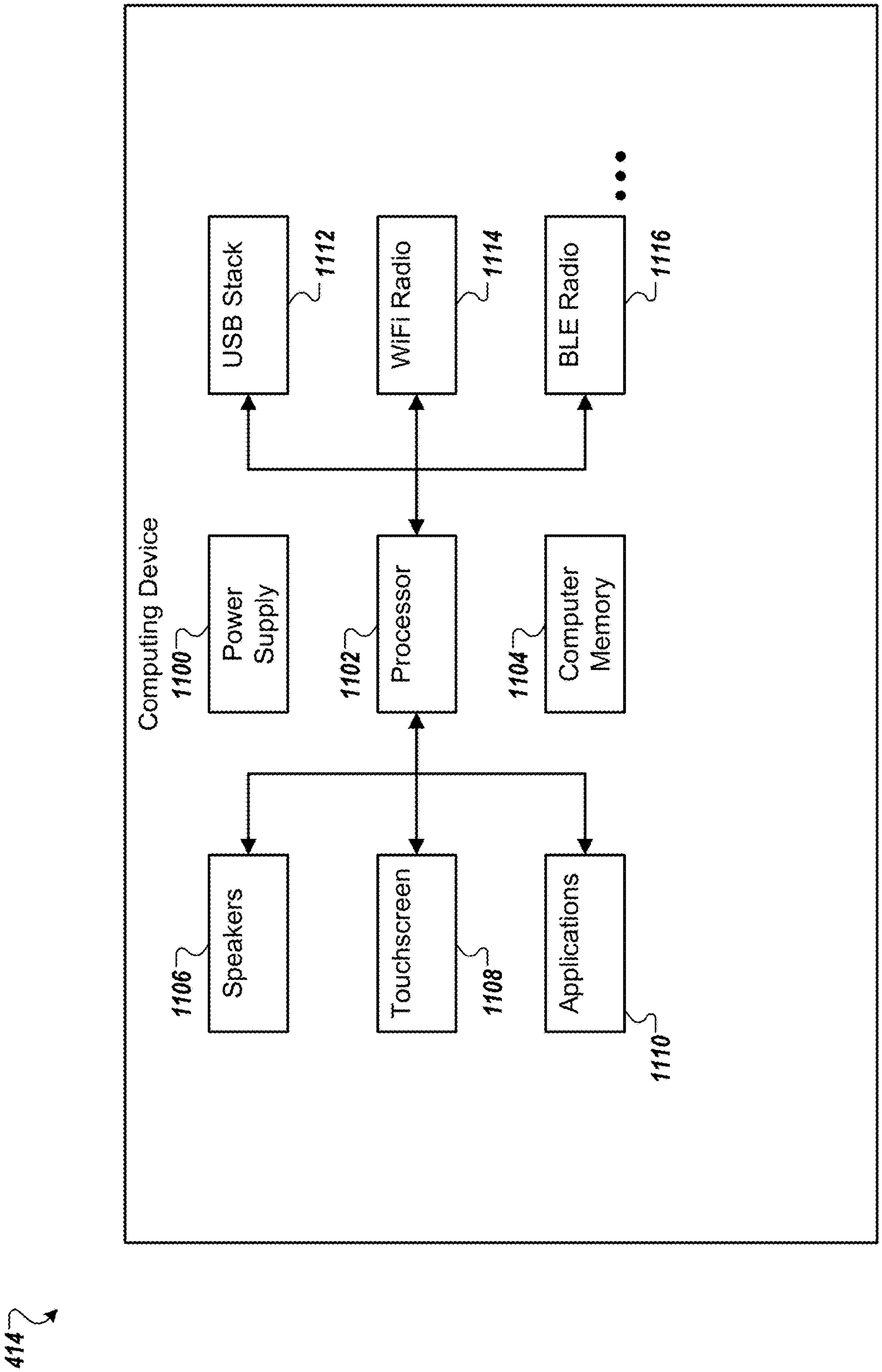
FIG. 11 is a block diagram of an example of a computing device that can be used in a data processing system that can be associated with a bed.

FIG. 11 is a block diagram of an example of a computing device 414 that can be used in a data processing system that can be associated with a bed system, including those described above with respect to FIGS. 1-3. The computing device 414 can include, for example, computing devices used by a user of a bed. Example computing devices 414 include, but are not limited to, mobile computing devices (e.g., mobile phones, tablet computers, laptops) and desktop computers.

The computing device 414 includes a power supply 1100, a processor 1102, and computer readable memory 1104. User input and output can be transmitted by, for example, speakers 1106, a touchscreen 1108, or other not shown components such as a pointing device or keyboard. The computing device 414 can run one or more applications 1110. These applications can include, for example, application to allow the user to interact with the system 400. These applications can allow a user to view information about the bed (e.g., sensor readings, sleep metrics), or configure the behavior of the system 400 (e.g., set a desired firmness to the bed, set desired behavior for peripheral devices). In some cases, the computing device 414 can be used in addition to, or to replace, the remote control 122 described previously.

Figure 12:
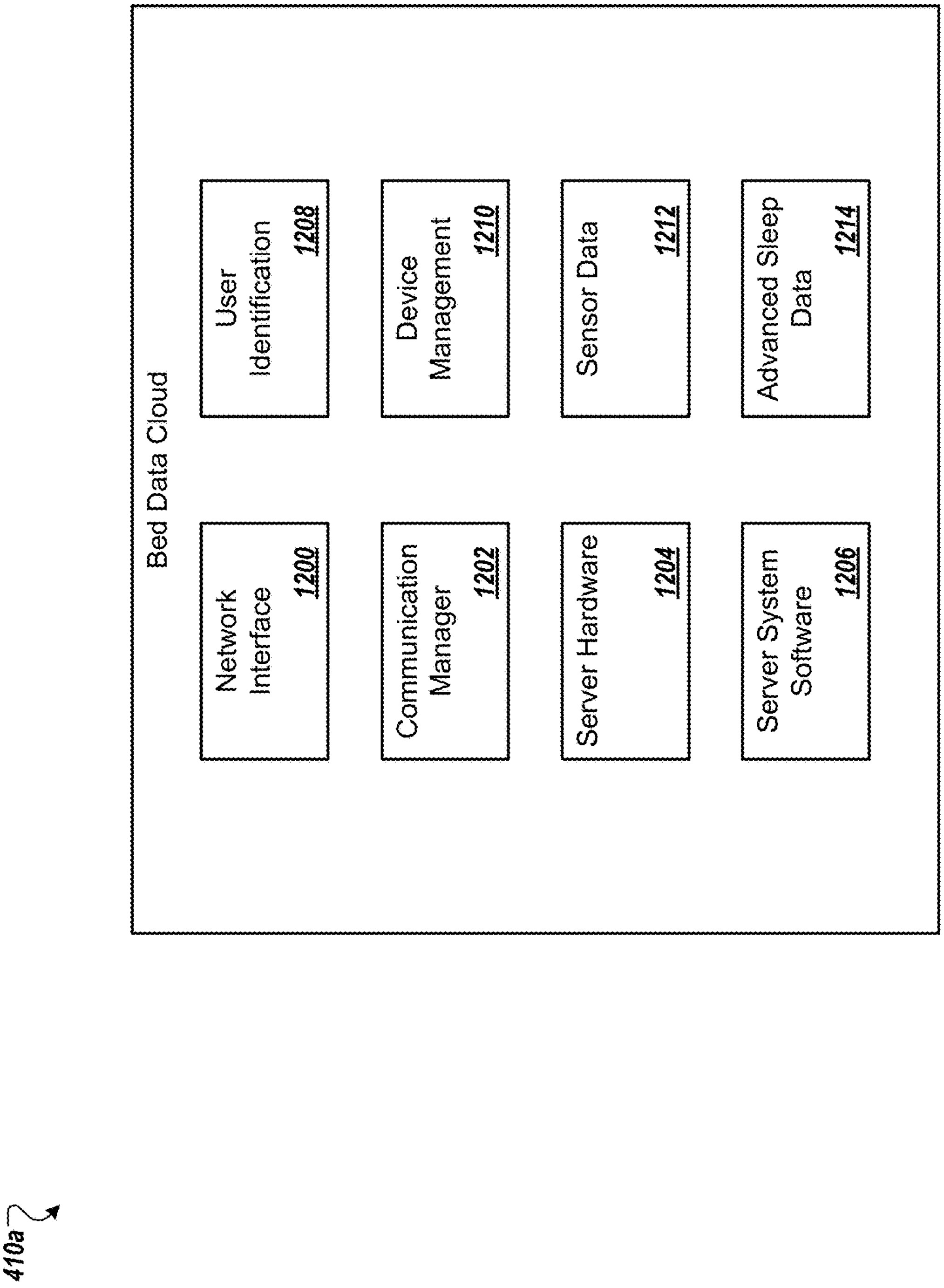
FIGS. 12-16 are block diagrams of example cloud services that can be used in a data processing system that can be associated with a bed.

FIG. 12 is a block diagram of an example bed data cloud service 410*a* that can be used in a data processing system that can be associated with a bed system, including those described above with respect to FIGS. 1-3. In this example, the bed data cloud service 410*a* is configured to collect sensor data and sleep data from a particular bed, and to match the sensor and sleep data with one or more users that use the bed when the sensor and sleep data was generated.

The bed data cloud service 410*a* is shown with a network interface 1200, a communication manager 1202, server hardware 1204, and server system software 1206. In addition, the bed data cloud service 410*a* is shown with a user identification module 1208, a device management 1210 module, a sensor data module 1212, and an advanced sleep data module 1214.

The network interface 1200 generally includes hardware and low level software used to allow one or more hardware devices to communicate over networks. For example the network interface 1200 can include network cards, routers, modems, and other hardware needed to allow the components of the bed data cloud service 410*a* to communicate with each other and other destinations over, for example, the Internet 412. The communication manger 1202 generally comprises hardware and software that operate above the network interface 1200. This includes software to initiate, maintain, and tear down network communications used by the bed data cloud service 410*a*. This includes, for example, TCP/IP, SSL or TLS, Torrent, and other communication sessions over local or wide area networks. The communication manger 1202 can also provide load balancing and other services to other elements of the bed data cloud service 410*a*.

The server hardware 1204 generally includes the physical processing devices used to instantiate and maintain bed data cloud service 410*a*. This hardware includes, but is not limited to processors (e.g., central processing units, ASICs, graphical processers), and computer readable memory (e.g., random access memory, stable hard disks, tape backup). One or more servers can be configured into clusters, multi-computer, or datacenters that can be geographically separate or connected.

The server system software 1206 generally includes software that runs on the server hardware 1204 to provide operating environments to applications and services. The server system software 1206 can include operating systems running on real servers, virtual machines instantiated on real servers to create many virtual servers, server level operations such as data migration, redundancy, and backup.

The user identification 1208 can include, or reference, data related to users of beds with associated data processing systems. For example, the users can include customers, owners, or other users registered with the bed data cloud service 410*a* or another service. Each user can have, for example, a unique identifier, user credentials, contact information, billing information, demographic information, or any other technologically appropriate information.

The device manager 1210 can include, or reference, data related to beds or other products associated with data processing systems. For example, the beds can include products sold or registered with a system associated with the bed data cloud service 410*a*. Each bed can have, for example, a unique identifier, model and/or serial number, sales information, geographic information, delivery information, a listing of associated sensors and control peripherals, etc. Additionally, an index or indexes stored by the bed data cloud service 410*a* can identify users that are associated with beds. For example, this index can record sales of a bed to a user, users that sleep in a bed, etc.

The sensor data 1212 can record raw or condensed sensor data recorded by beds with associated data processing systems. For example, a bed's data processing system can have a temperature sensor, pressure sensor, and light sensor. Readings from these sensors, either in raw form or in a format generated from the raw data (e.g. sleep metrics) of the sensors, can be communicated by the bed's data processing system to the bed data cloud service 410*a* for storage in the sensor data 1212. Additionally, an index or indexes stored by the bed data cloud service 410*a* can identify users and/or beds that are associated with the sensor data 1212.

The bed data cloud service 410*a* can use any of its available data to generate advanced sleep data 1214. In general, the advanced sleep data 1214 includes sleep metrics and other data generated from sensor readings. Some of these calculations can be performed in the bed data cloud service 410*a* instead of locally on the bed's data processing system, for example, because the calculations are computationally complex or require a large amount of memory space or processor power that is not available on the bed's data processing system. This can help allow a bed system to operate with a relatively simple controller and still be part of a system that performs relatively complex tasks and computations.

Figure 13:
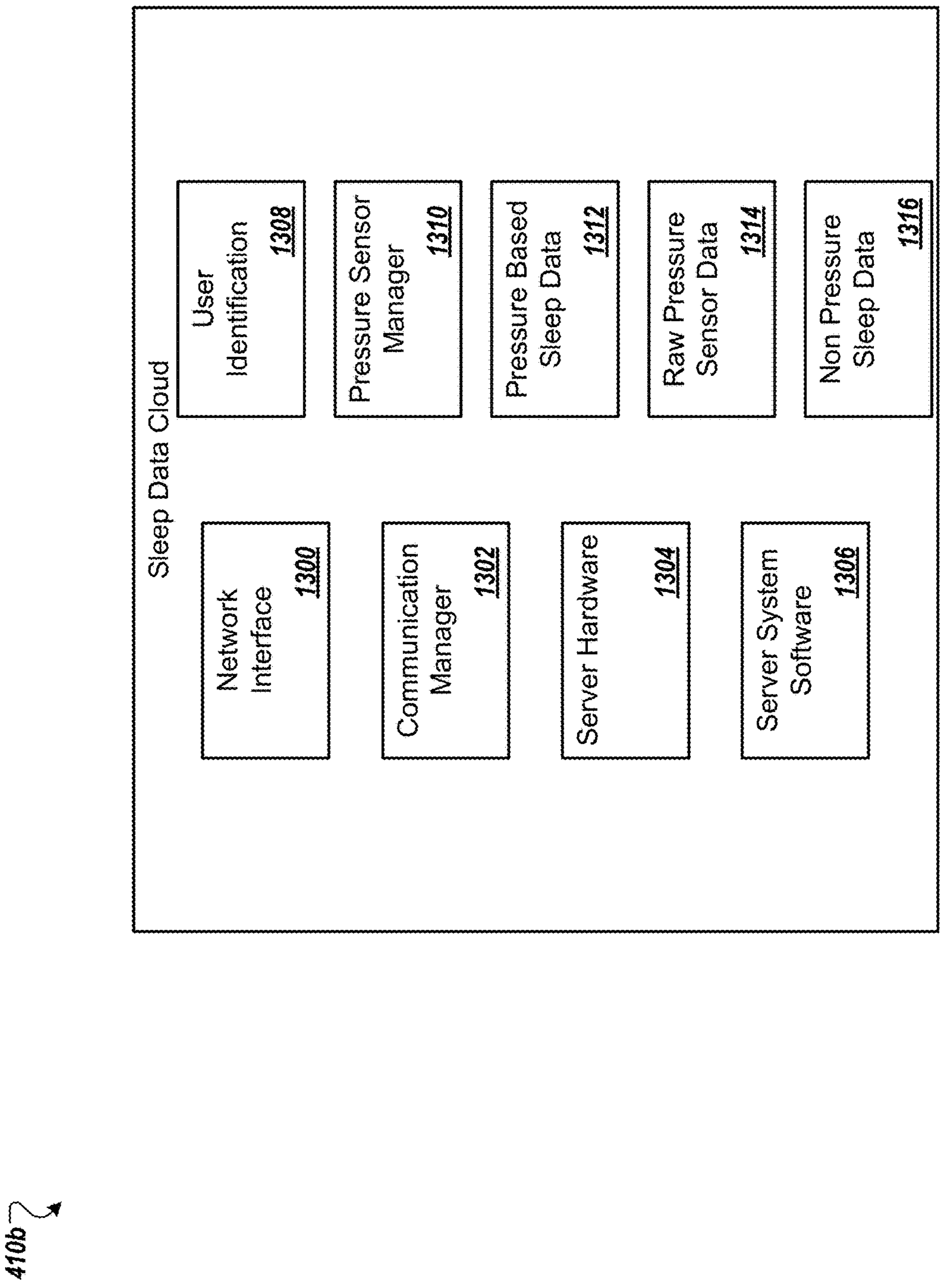

FIG. 13 is a block diagram of an example sleep data cloud service 410*b* that can be used in a data processing system that can be associated with a bed system, including those described above with respect to FIGS. 1-3. In this example, the sleep data cloud service 410*b* is configured to record data related to users' sleep experience.

The sleep data cloud service 410*b* is shown with a network interface 1300, a communication manager 1302, server hardware 1304, and server system software 1306. In addition, the sleep data cloud service 410*b* is shown with a user identification module 1308, a pressure sensor manager 1310, a pressure based sleep data module 1312, a raw pressure sensor data module 1314, and a non-pressure sleep data module 1316.

The pressure sensor manager 1310 can include, or reference, data related to the configuration and operation of pressure sensors in beds. For example, this data can include an identifier of the types of sensors in a particular bed, their settings and calibration data, etc.

The pressure based sleep data 1312 can use raw pressure sensor data 1314 to calculate sleep metrics specifically tied to pressure sensor data. For example, user presence, movements, weight change, heart rate, and breathing rate can all be determined from raw pressure sensor data 1314. Additionally, an index or indexes stored by the sleep data cloud service 410*b* can identify users that are associated with pressure sensors, raw pressure sensor data, and/or pressure based sleep data.

The non-pressure sleep data 1316 can use other sources of data to calculate sleep metrics. For example, user entered preferences, light sensor readings, and sound sensor readings can all be used to track sleep data. Additionally, an index or indexes stored by the sleep data cloud service 410*b* can identify users that are associated with other sensors and/or non-pressure sleep data 1316.

Figure 14:
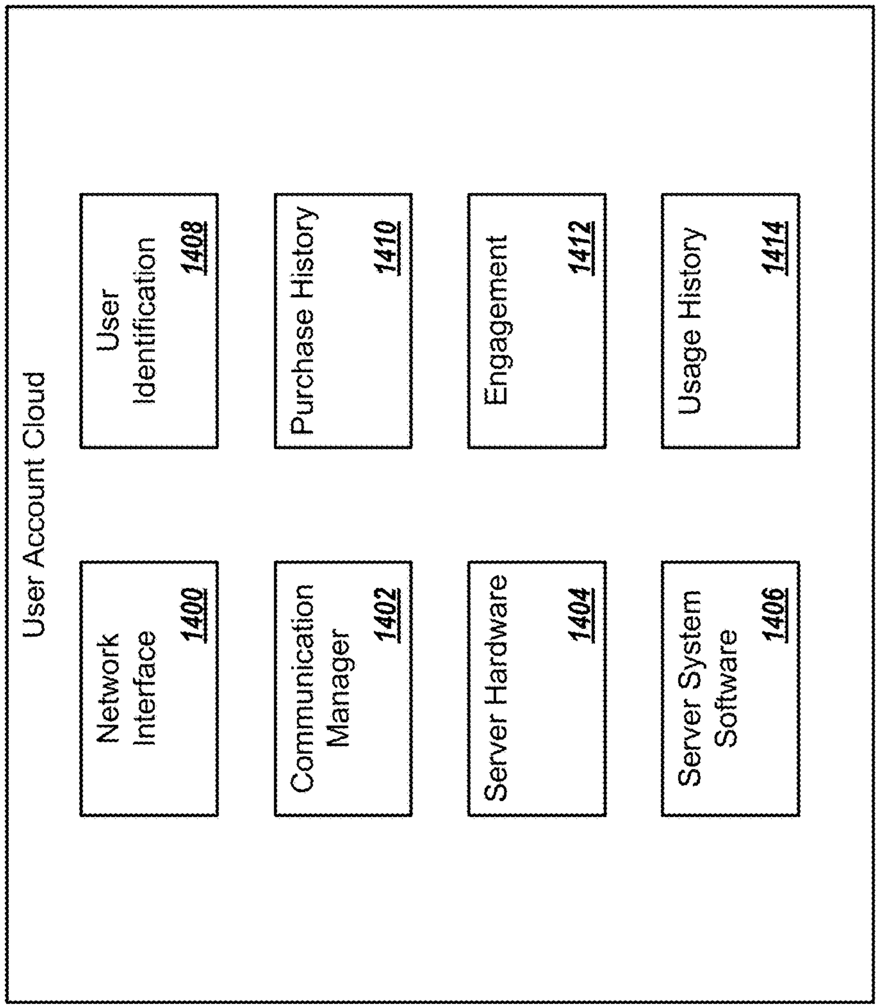

FIG. 14 is a block diagram of an example user account cloud service 410*c* that can be used in a data processing system that can be associated with a bed system, including those described above with respect to FIGS. 1-3. In this example, the user account cloud service 410*c* is configured to record a list of users and to identify other data related to those users.

The user account cloud service 410*c* is shown with a network interface 1400, a communication manager 1402, server hardware 1404, and server system software 1406. In addition, the user account cloud service 410*c* is shown with a user identification module 1408, a purchase history module 1410, an engagement module 1412, and an application usage history module 1414.

The user identification module 1408 can include, or reference, data related to users of beds with associated data processing systems. For example, the users can include customers, owners, or other users registered with the user account cloud service 410*a* or another service. Each user can have, for example, a unique identifier, and user credentials, demographic information, or any other technologically appropriate information.

The purchase history module 1410 can include, or reference, data related to purchases by users. For example, the purchase data can include a sale's contact information, billing information, and salesperson information. Additionally, an index or indexes stored by the user account cloud service 410*c* can identify users that are associated with a purchase.

The engagement 1412 can track user interactions with the manufacturer, vendor, and/or manager of the bed and or cloud services. This engagement data can include communications (e.g., emails, service calls), data from sales (e.g., sales receipts, configuration logs), and social network interactions.

The usage history module 1414 can contain data about user interactions with one or more applications and/or remote controls of a bed. For example, a monitoring and configuration application can be distributed to run on, for example, computing devices 412. This application can log and report user interactions for storage in the application usage history module 1414. Additionally, an index or indexes stored by the user account cloud service 410*c* can identify users that are associated with each log entry.

Figure 15:
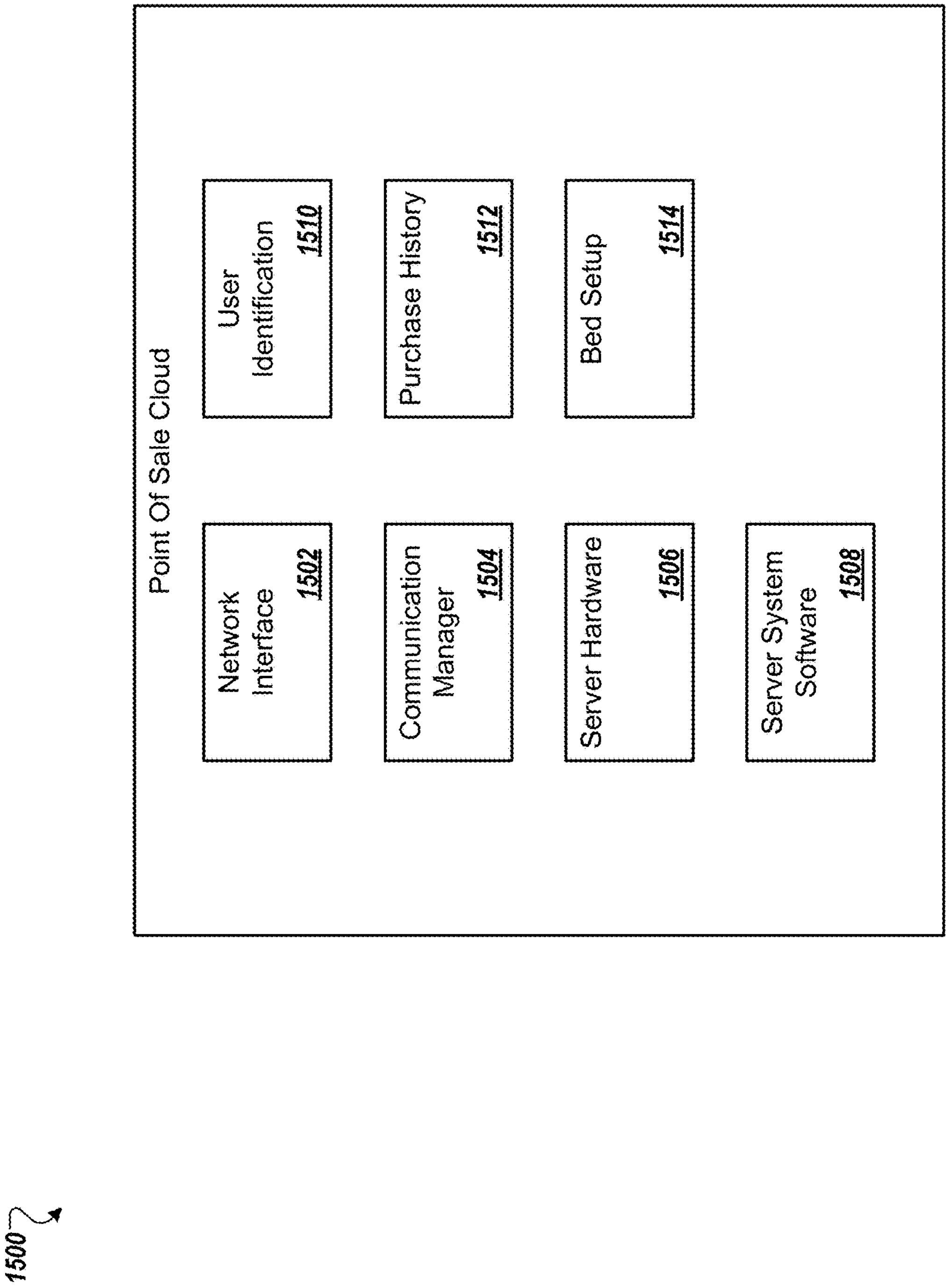

FIG. 15 is a block diagram of an example point of sale cloud service 1500 that can be used in a data processing system that can be associated with a bed system, including those described above with respect to FIGS. 1-3. In this example, the point of sale cloud service 1500 is configured to record data related to users' purchases.

The point of sale cloud service 1500 is shown with a network interface 1502, a communication manager 1504, server hardware 1506, and server system software 1508. In addition, the point of sale cloud service 1500 is shown with a user identification module 1510, a purchase history module 1512, and a setup module 1514.

The purchase history module 1512 can include, or reference, data related to purchases made by users identified in the user identification module 1510. The purchase information can include, for example, data of a sale, price, and location of sale, delivery address, and configuration options selected by the users at the time of sale. These configuration options can include selections made by the user about how they wish their newly purchased beds to be setup and can include, for example, expected sleep schedule, a listing of peripheral sensors and controllers that they have or will install, etc.

The bed setup module 1514 can include, or reference, data related to installations of beds that users' purchase. The bed setup data can include, for example, the date and address to which a bed is delivered, the person that accepts delivery, the configuration that is applied to the bed upon delivery, the name or names of the person or people who will sleep on the bed, which side of the bed each person will use, etc.

Data recorded in the point of sale cloud service 1500 can be referenced by a user's bed system at later dates to control functionality of the bed system and/or to send control signals to peripheral components according to data recorded in the point of sale cloud service 1500. This can allow a salesperson to collect information from the user at the point of sale that later facilitates automation of the bed system. In some examples, some or all aspects of the bed system can be automated with little or no user-entered data required after the point of sale. In other examples, data recorded in the point of sale cloud service 1500 can be used in connection with a variety of additional data gathered from user-entered data.

Figure 16:
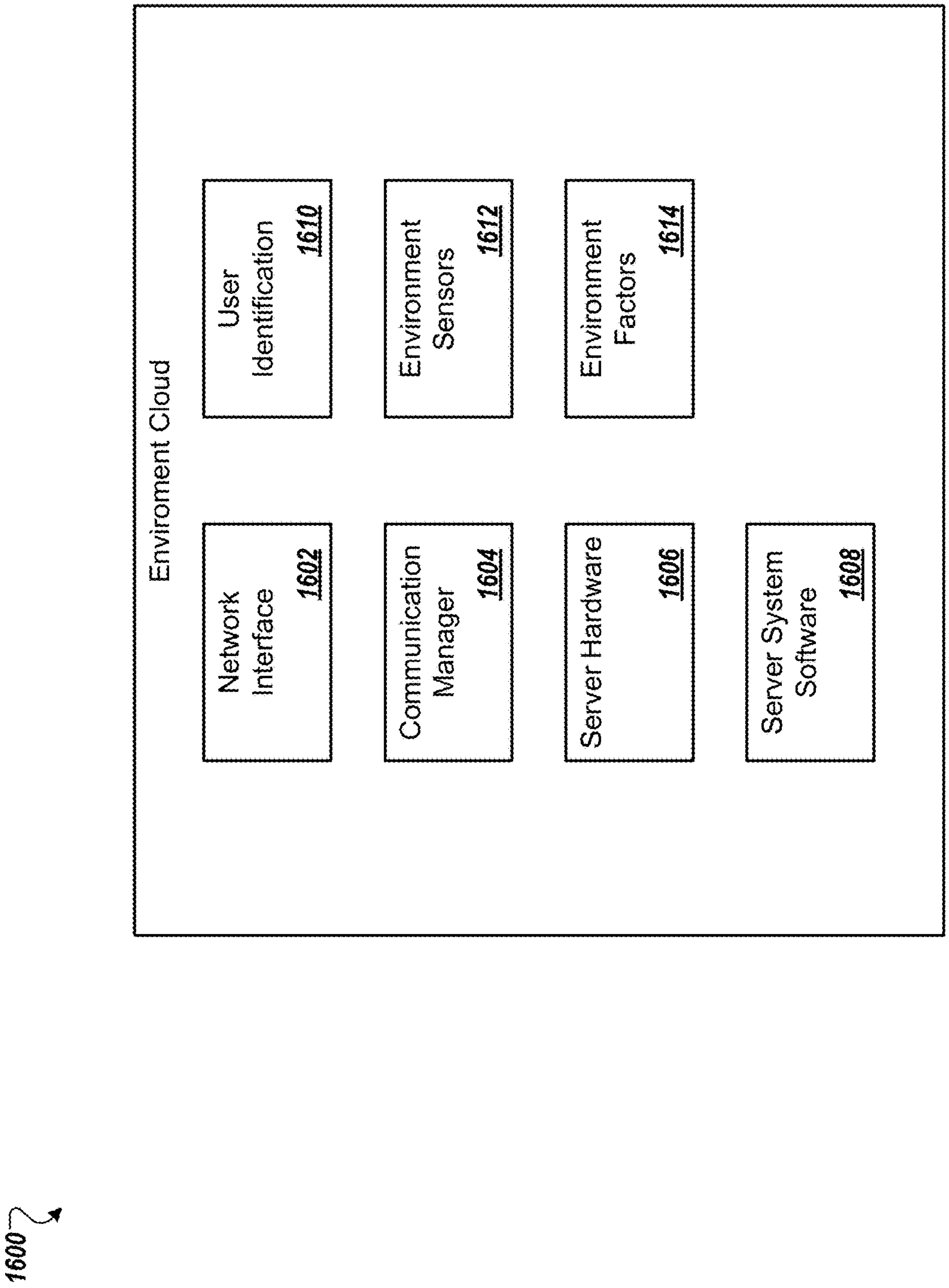

FIG. 16 is a block diagram of an example environment cloud service 1600 that can be used in a data processing system that can be associated with a bed system, including those described above with respect to FIGS. 1-3. In this example, the environment cloud service 1600 is configured to record data related to users' home environment.

The environment cloud service 1600 is shown with a network interface 1602, a communication manager 1604, server hardware 1606, and server system software 1608. In addition, the environment cloud service 1600 is shown with a user identification module 1610, an environmental sensor module 1612, and an environmental factors module 1614.

The environmental sensors module 1612 can include a listing of sensors that users' in the user identification module 1610 have installed in their bed. These sensors include any sensors that can detect environmental variables—light sensors, noise sensors, vibration sensors, thermostats, etc. Additionally, the environmental sensors module 1612 can store historical readings or reports from those sensors.

The environmental factors module 1614 can include reports generated based on data in the environmental sensors module 1612. For example, for a user with a light sensor with data in the environment sensors module 1612, the environmental factors module 1614 can hold a report indicating the frequency and duration of instances of increased lighting when the user is asleep.

In the examples discussed here, each cloud service 410 is shown with some of the same components. In various configurations, these same components can be partially or wholly shared between services, or they can be separate. In some configurations, each service can have separate copies of some or all of the components that are the same or different in some ways. Additionally, these components are only supplied as illustrative examples. In other examples each cloud service can have different number, types, and styles of components that are technically possible.

Figure 17:
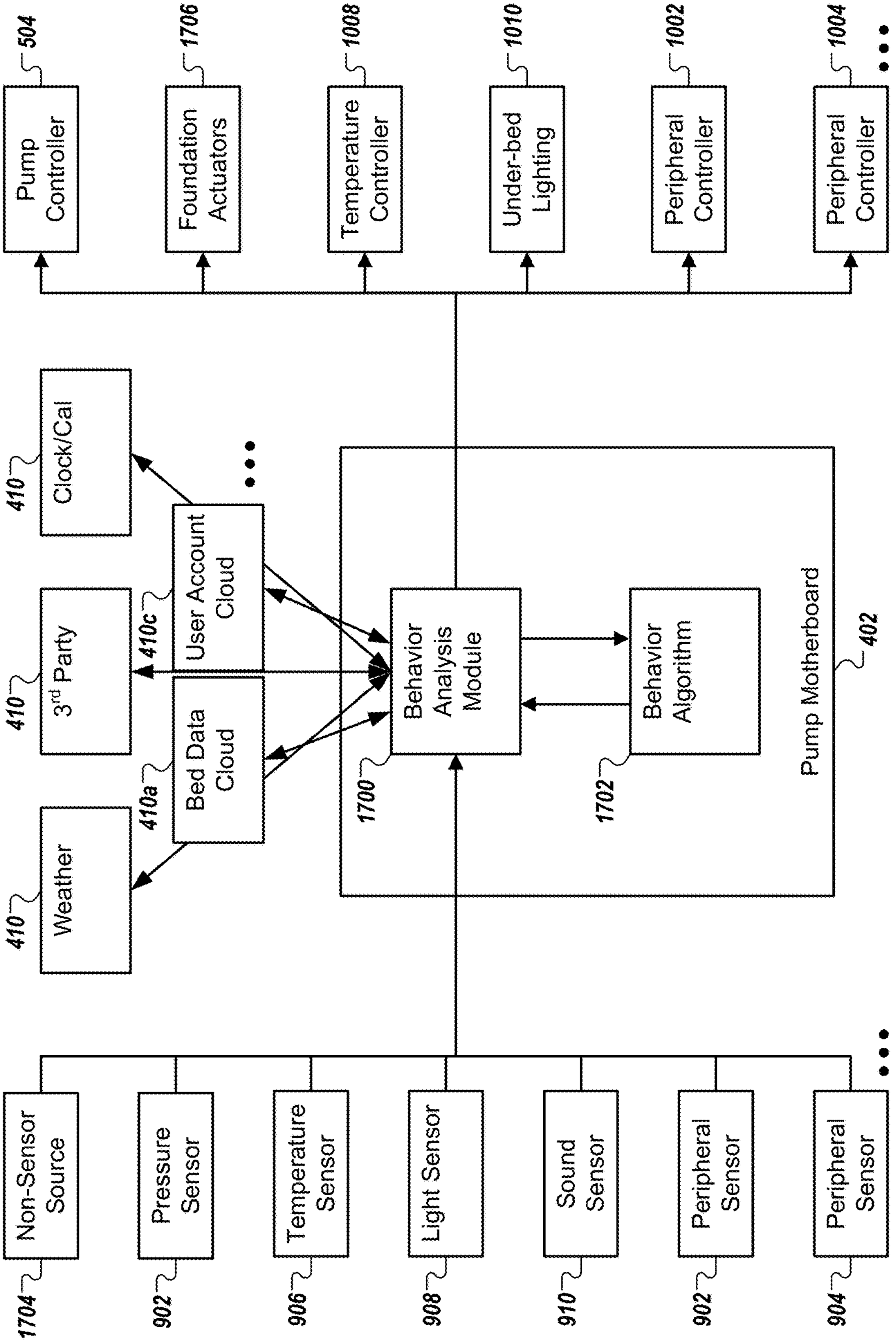
FIG. 17 is a block diagram of an example of using a data processing system that can be associated with a bed to automate peripherals around the bed.

FIG. 17 is a block diagram of an example of using a data processing system that can be associated with a bed (such as a bed of the bed systems described herein) to automate peripherals around the bed. Shown here is a behavior analysis module 1700 that runs on the pump motherboard 402. For example, the behavior analysis module 1700 can be one or more software components stored on the computer memory 512 and executed by the processor 502. In general, the behavior analysis module 1700 can collect data from a wide variety of sources (e.g., sensors, non-sensor local sources, cloud data services) and use a behavioral algorithm 1702 to generate one or more actions to be taken (e.g., commands to send to peripheral controllers, data to send to cloud services). This can be useful, for example, in tracking user behavior and automating devices in communication with the user's bed.

The behavior analysis module 1700 can collect data from any technologically appropriate source, for example, to gather data about features of a bed, the bed's environment, and/or the bed's users. Some such sources include any of the sensors of the sensor array 406. For example, this data can provide the behavior analysis module 1700 with information about the current state of the environment around the bed. For example, the behavior analysis module 1700 can access readings from the pressure sensor 902 to determine the pressure of an air chamber in the bed. From this reading, and potentially other data, user presence in the bed can be determined. In another example, the behavior analysis module can access a light sensor 908 to detect the amount of light in the bed's environment.

Similarly, the behavior analysis module 1700 can access data from cloud services. For example, the behavior analysis module 1700 can access the bed cloud service 410*a* to access historical sensor data 1212 and/or advanced sleep data 1214. Other cloud services 410, including those not previously described can be accessed by the behavior analysis module 1700. For example, the behavior analysis module 1700 can access a weather reporting service, a 3$^{rd}$ party data provider (e.g., traffic and news data, emergency broadcast data, user travel data), and/or a clock and calendar service.

Similarly, the behavior analysis module 1700 can access data from non-sensor sources 1704. For example, the behavior analysis module 1700 can access a local clock and calendar service (e.g., a component of the motherboard 402 or of the processor 502).

The behavior analysis module 1700 can aggregate and prepare this data for use by one or more behavioral algorithms 1702. The behavioral algorithms 1702 can be used to learn a user's behavior and/or to perform some action based on the state of the accessed data and/or the predicted user behavior. For example, the behavior algorithm 1702 can use available data (e.g., pressure sensor, non-sensor data, clock and calendar data) to create a model of when a user goes to bed every night. Later, the same or a different behavioral algorithm 1702 can be used to determine if an increase in air chamber pressure is likely to indicate a user going to bed and, if so, send some data to a third-party cloud service 410 and/or engage a device such as a pump controller 504, foundation actuators 1706, temperature controller 1008, under-bed lighting 1010, a peripheral controller 1002, or a peripheral controller 1004, to name a few.

In the example shown, the behavioral analysis module 1700 and the behavioral algorithm 1702 are shown as components of the motherboard 402. However, other configurations are possible. For example, the same or a similar behavioral analysis module and/or behavior algorithm can be run in one or more cloud services, and the resulting output can be sent to the motherboard 402, a controller in the controller array 408, or to any other technologically appropriate recipient.

Figure 18:
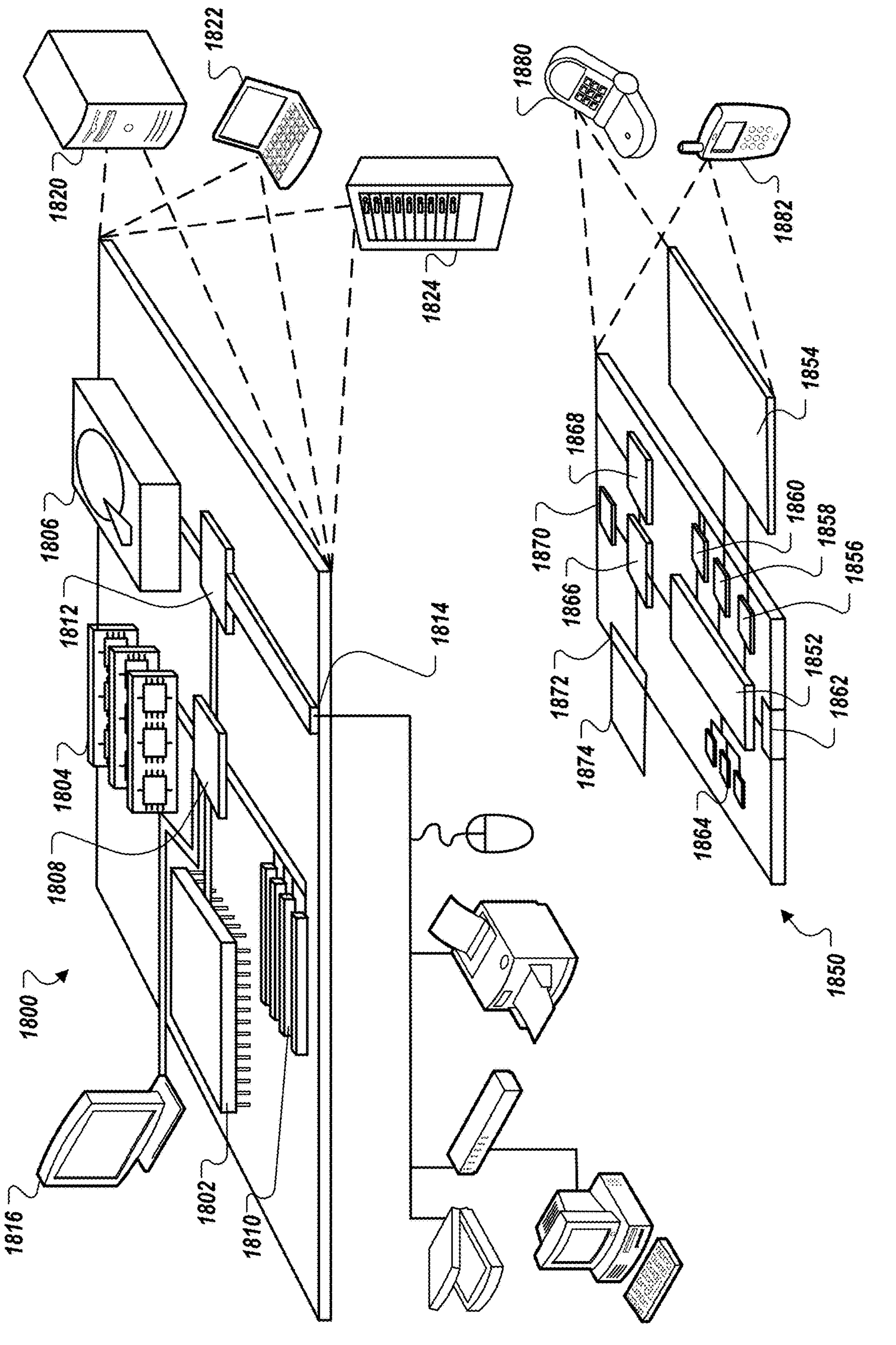
FIG. 18 is a schematic diagram that shows an example of a computing device and a mobile computing device.

FIG. 18 shows an example of a computing device 1800 and an example of a mobile computing device that can be used to implement the techniques described here. The computing device 1800 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1800 includes a processor 1802, a memory 1804, a storage device 1806, a high-speed interface 1808 connecting to the memory 1804 and multiple high-speed expansion ports 1810, and a low-speed interface 1812 connecting to a low-speed expansion port 1814 and the storage device 1806. Each of the processor 1802, the memory 1804, the storage device 1806, the high-speed interface 1808, the high-speed expansion ports 1810, and the low-speed interface 1812, are interconnected using various busses, and can be mounted on a common motherboard or in other manners as appropriate. The processor 1802 can process instructions for execution within the computing device 1800, including instructions stored in the memory 1804 or on the storage device 1806 to display graphical information for a GUI on an external input/output device, such as a display 1816 coupled to the high-speed interface 1808. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 1804 stores information within the computing device 1800. In some implementations, the memory 1804 is a volatile memory unit or units. In some implementations, the memory 1804 is a non-volatile memory unit or units. The memory 1804 can also be another form of computer-readable medium, such as a magnetic or optical disk.

The storage device 1806 is capable of providing mass storage for the computing device 1800. In some implementations, the storage device 1806 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 1804, the storage device 1806, or memory on the processor 1802.

The high-speed interface 1808 manages bandwidth-intensive operations for the computing device 1800, while the low-speed interface 1812 manages lower bandwidth-intensive operations. Such allocation of functions is exemplary only. In some implementations, the high-speed interface 1808 is coupled to the memory 1804, the display 1816 (e.g., through a graphics processor or accelerator), and to the high-speed expansion ports 1810, which can accept various expansion cards (not shown). In the implementation, the low-speed interface 1812 is coupled to the storage device 1806 and the low-speed expansion port 1814. The low-speed expansion port 1814, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 1800 can be implemented in a number of different forms, as shown in the figure. For example, it can be implemented as a standard server 1820, or multiple times in a group of such servers. In addition, it can be implemented in a personal computer such as a laptop computer 1822. It can also be implemented as part of a rack server system 1824. Alternatively, components from the computing device 1800 can be combined with other components in a mobile device (not shown), such as a mobile computing device 1850. Each of such devices can contain one or more of the computing device 1800 and the mobile computing device 1850, and an entire system can be made up of multiple computing devices communicating with each other.

The mobile computing device 1850 includes a processor 1852, a memory 1864, an input/output device such as a display 1854, a communication interface 1866, and a transceiver 1868, among other components. The mobile computing device 1850 can also be provided with a storage device, such as a micro-drive or other device, to provide additional storage. Each of the processor 1852, the memory 1864, the display 1854, the communication interface 1866, and the transceiver 1868, are interconnected using various buses, and several of the components can be mounted on a common motherboard or in other manners as appropriate.

The processor 1852 can execute instructions within the mobile computing device 1850, including instructions stored in the memory 1864. The processor 1852 can be implemented as a chipset of chips that include separate and multiple analog and digital processors. The processor 1852 can provide, for example, for coordination of the other components of the mobile computing device 1850, such as control of user interfaces, applications run by the mobile computing device 1850, and wireless communication by the mobile computing device 1850.

The processor 1852 can communicate with a user through a control interface 1858 and a display interface 1856 coupled to the display 1854. The display 1854 can be, for example, a TFT (Thin-Film-Transistor Liquid Crystal Display) display or an OLED (Organic Light Emitting Diode) display, or other appropriate display technology. The display interface 1856 can comprise appropriate circuitry for driving the display 1854 to present graphical and other information to a user. The control interface 1858 can receive commands from a user and convert them for submission to the processor 1852. In addition, an external interface 1862 can provide communication with the processor 1852, so as to enable near area communication of the mobile computing device 1850 with other devices. The external interface 1862 can provide, for example, for wired communication in some implementations, or for wireless communication in other implementations, and multiple interfaces can also be used.

The memory 1864 stores information within the mobile computing device 1850. The memory 1864 can be implemented as one or more of a computer-readable medium or media, a volatile memory unit or units, or a non-volatile memory unit or units. An expansion memory 1874 can also be provided and connected to the mobile computing device 1850 through an expansion interface 1872, which can include, for example, a SIMM (Single In Line Memory Module) card interface. The expansion memory 1874 can provide extra storage space for the mobile computing device 1850, or can also store applications or other information for the mobile computing device 1850. Specifically, the expansion memory 1874 can include instructions to carry out or supplement the processes described above, and can include secure information also. Thus, for example, the expansion memory 1874 can be provide as a security module for the mobile computing device 1850, and can be programmed with instructions that permit secure use of the mobile computing device 1850. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 1864, the expansion memory 1874, or memory on the processor 1852. In some implementations, the computer program product can be received in a propagated signal, for example, over the transceiver 1868 or the external interface 1862.

The mobile computing device 1850 can communicate wirelessly through the communication interface 1866, which can include digital signal processing circuitry where necessary. The communication interface 1866 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 1868 using a radio-frequency. In addition, short-range communication can occur, such as using a Bluetooth, WiFi, or other such transceiver (not shown). In addition, a GPS (Global Positioning System) receiver module 1870 can provide additional navigation- and location-related wireless data to the mobile computing device 1850, which can be used as appropriate by applications running on the mobile computing device 1850.

The mobile computing device 1850 can also communicate audibly using an audio codec 1860, which can receive spoken information from a user and convert it to usable digital information. The audio codec 1860 can likewise generate audible sound for a user, such as through a speaker, e.g., in a handset of the mobile computing device 1850. Such sound can include sound from voice telephone calls, can include recorded sound (e.g., voice messages, music files, etc.) and can also include sound generated by applications operating on the mobile computing device 1850.

The mobile computing device 1850 can be implemented in a number of different forms, as shown in the figure. For example, it can be implemented as a cellular telephone 1880. It can also be implemented as part of a smart-phone 1882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a backend component (e.g., as a data server), or that includes a middleware component (e.g., an application server), or that includes a frontend component (e.g., a client computer having a graphical user interface or a Web browser through which a user can interact with an implementation of the systems and techniques described here), or any combination of such backend, middleware, or frontend components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Figure 19:
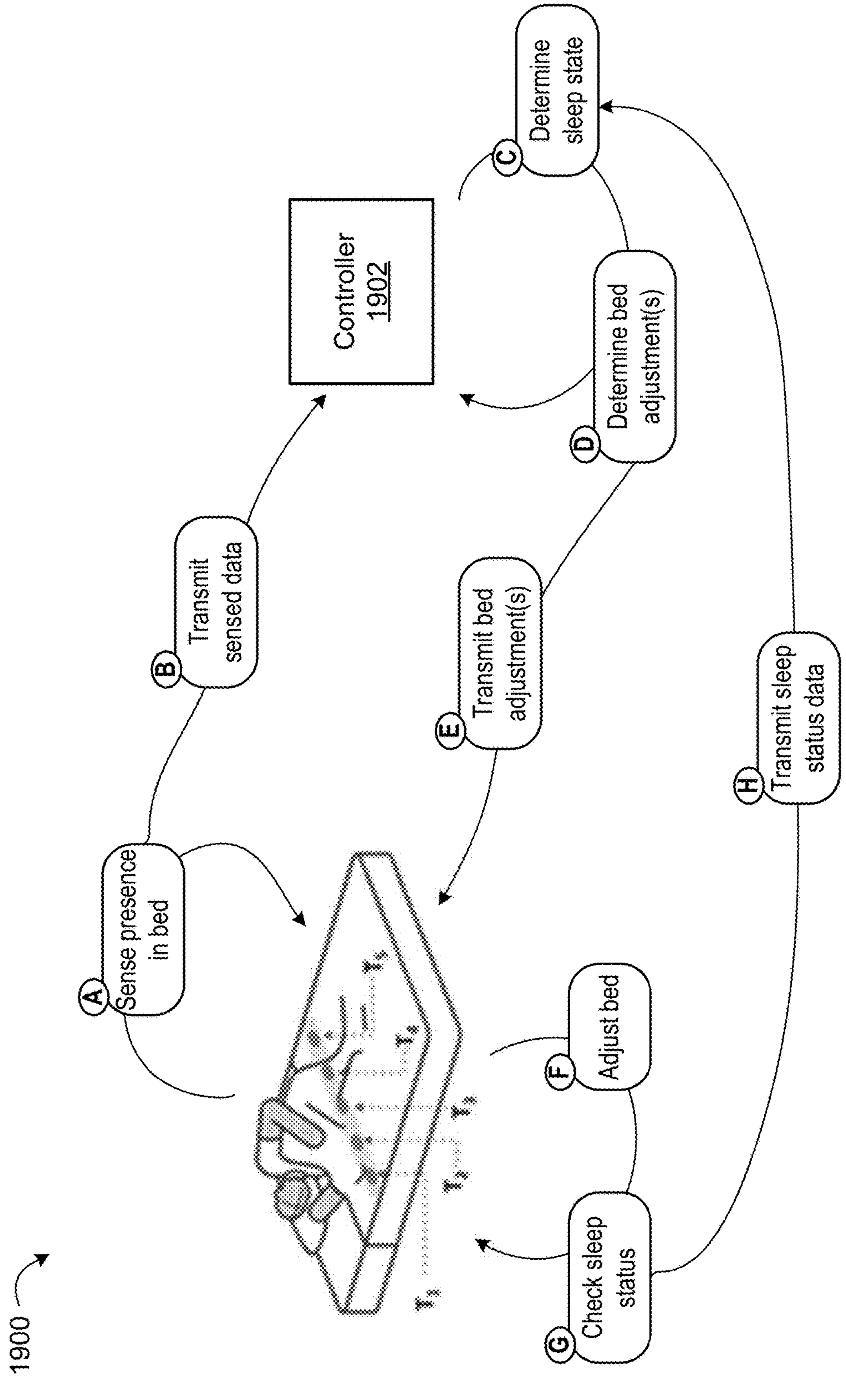
FIG. 19 is a conceptual diagram of an example of adjusting mattress firmness based on a current sleep state of a user.

FIG. 19 is a conceptual diagram of an example of adjusting mattress firmness based on a current sleep state of a user. As depicted, the user can be sleeping in a bed system 1900. The bed system 1900 can be in data communication (e.g., wired, wireless) with a controller 1902. The controller 1902 can be configured to determine a sleep state of the user and make adjustments to the bed system 1900 based on the user's sleep state (e.g., refer to the process 2100 in FIG. 21).

The bed system 1900 can sense presence of the user in the bed (A). As described herein, the bed system 1900 can include a plurality of sensors (e.g., a sensor system) configured to detect pressure, temperature, and other indicators of the user when the user lays on top of a mattress of the bed system 1900. In some implementations, the sensors can be part of wearable devices (e.g., smart watch, heart rate monitor, smart clothes, etc.) and/or "nearables" such as mobile phones or home automation devices that are in data communication with the controller 1902. Any one or more of the sensors described herein can capture presence information about the user.

The presence information can include a variety of different signals. For example, the presence information can include audio waves indicative of breathing and/or snoring of the user. The presence information can include pressure in the mattress indicative of movement of the user on top of the mattress. The presence information can also include pressure changes in one or more air chambers or sections of the mattress indicative of the user being on top of the mattress. The presence information can also include pressure changes or other measurements indicative of the user's heartbeat, breathing rate, and/or respiration rate. Moreover, the presence information can include temperature of the user. The presence information can also indicate changes in temperature at a top surface of the mattress indicative that the user is on top of the mattress. The presence information can include any one or more additional measurements that can be used to determine that the user is presently on top of the mattress/in the bed system 1900.

The sensed data can be transmitted to the controller 1902 (B). The data can be transmitted as it is sensed. In some implementations, the bed system 1900 can be configured to sense presence information at predetermined time intervals. At an end of each of the time intervals, the bed system 1900 can transmit the sensed data to the controller 1902. Moreover, in some implementations, the bed system 1900 can receive a request from the controller 1902 to sense presence information of the user. At that point, the bed system 1900 can sense the presence information and transmit the sensed data to the controller 1902.

Based on the sensed data, the controller 1902 can determine a current sleep state of the user (C). For example, as described throughout this disclosure, the controller 1902 can obtain pressure readings from the bed system 1900 that include gross movements (e.g., body, arm, leg, and/or head movements), cardiac movement, and/or respiratory movement. Such exemplary pressure readings can be inputs to an algorithm, as previously described, that determines the current sleep state of the user.

Using the determined sleep state, the controller 1902 can determine one or more adjustments that can be made to the bed system 1900 (D). For example, firmness of the mattress can be adjusted. When the controller 1902 identifies that the user's current sleep state is in NREM or REM, the controller 1902 can determine that the mattress firmness can be increased. After all, during REM sleep, the user's muscle tone can be substantially reduced. To compensate for the reduced muscle tone and to provide continuous sleep comfort throughout a sleep session, the controller 1902 can determine that the mattress firmness can be increased during REM sleep.

The controller 1902 can determine a certain amount or percent to increase or decrease the mattress firmness by. In some implementations, the controller 1902 can determine that the mattress firmness is increased or decreased by a predetermined amount or percent (e.g., 10% or 50% increase from a user-defined and/or user-preferred firmness setting). Firmness adjustments can therefore be incremental and/or based on predetermined threshold ranges (absolute or relative). The firmness adjustments can also be based on what sleep stage the user is currently in.

As another example of determining firmness adjustments, when the controller 1902 determines that the user's current sleep state a certain amount of time before the user's desired alarm or wakeup time, the controller 1902 can determine that the mattress firmness can be decreased or otherwise returned to a user-preferred or user-defined firmness setting.

The controller 1902 can transmit the bed adjustment(s) to the bed system 1900 (E). The bed system 1900 can then adjust the bed according to the information received from the controller 1902 (F). The transmitted bed adjustment(s) can include instructions that, when executed, cause one or more components of the bed system 1900 to alter a sleeping environment of the bed system 1900. For example, the transmitted bed adjustment(s) can include increasing firmness of the mattress by 10% from a current firmness setting of the mattress. When this adjustment is received by the bed system 1900 and executed, a pump of the bed system 1900 can be instructed to provide a predetermined amount of air (e.g., 10% of the current volume) to air chambers of the mattress. The air chambers can fill up with more air, thereby increasing firmness of the mattress.

As another example, the transmitted bed adjustment can include decreasing firmness by 10% from the current firmness setting of the mattress. When this adjustment is received by the bed system 1900 and executed, the pump of the bed system 1900 can be instructed to release a predetermined amount of air (e.g., 10% of the current firmness) from the air chambers of the mattress. The air chambers can deflate, thereby decreasing firmness of the mattress.

After adjustments are made to the bed system 1900, a sleep status of the user can be checked (G). The sleep status of the user can be checked to determine whether any changes have occurred during the user's sleep session. The user may have woken up, gotten out of bed, and/or transitioned into a different sleep stage. Changes in the user's sleep status can impact changes to the mattress firmness.

In cases where a pressure change causes a sleep disturbance, future pressure changes can be reduced in intensity to avoid future disturbances. For example, during or after a pressure change, if a change in sleep quality (e.g., increase in gross motor movement, awakening event) is detected, a pressure-change variable may be reduced for the sleeper, and future pressure changes can be changed by the new, lower, change variable.

For example, the bed system 1900 can collect presence data or other sensed data about the user. The bed system 1900 can then transmit this sleep status data to the controller 1902 (H). The controller 1902 can determine whether the user is still in the bed and/or the user's current sleep state (C). Items (C)-(H) in FIG. 19 can be repeated until the controller 1902 determines one or more conditions. The one or more conditions can include that (1) the user is no longer in the bed, (2) the user is a predetermined amount of time away from waking up to an alarm, (3) the user is awake, (4) the alarm has gone off, thereby ending the user's sleep session, and/or (5) the user's current sleep state has not changed from the previously identified sleep state.

Figure 20:
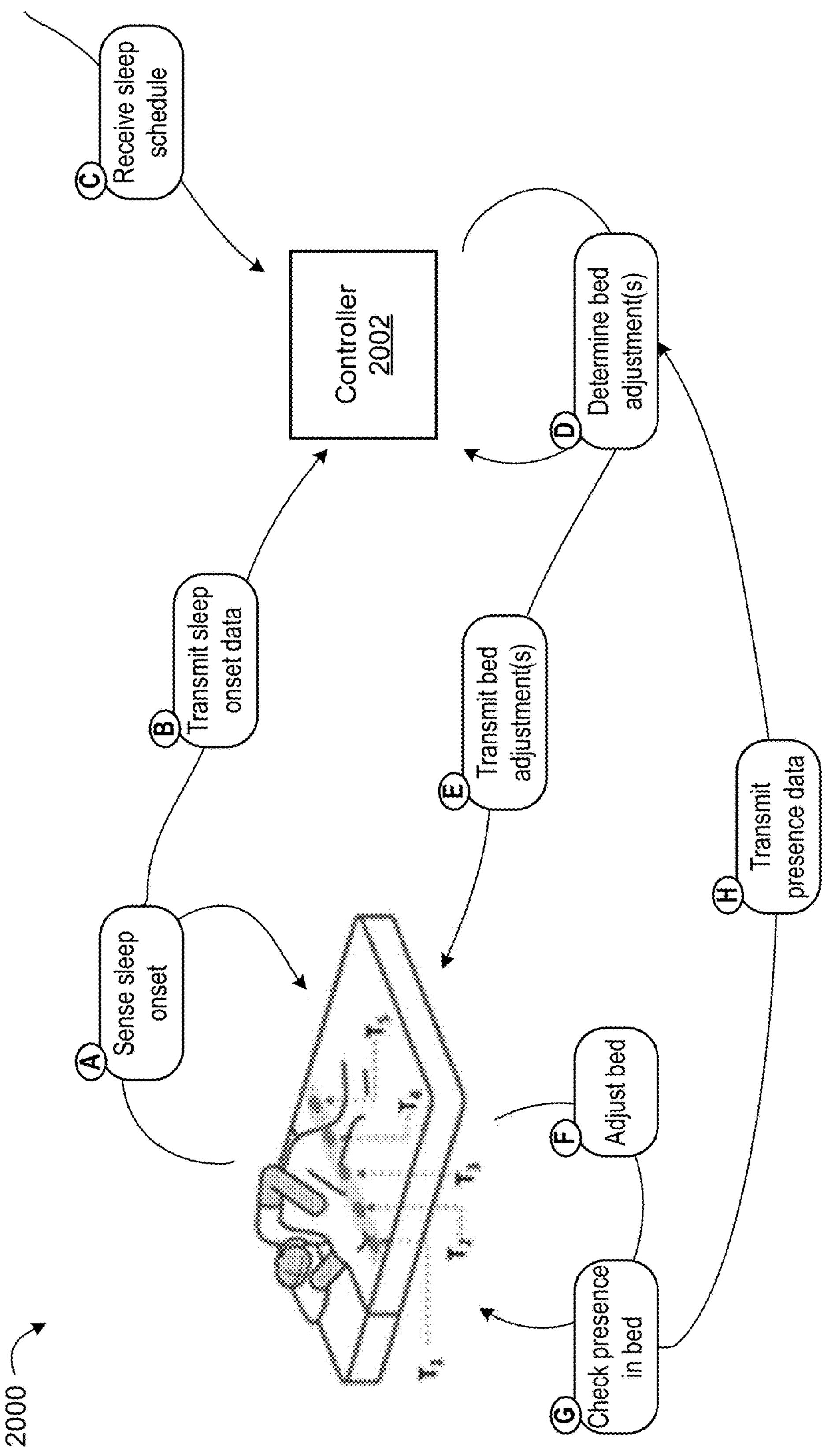
FIG. 20 is a conceptual diagram of an example of adjusting mattress firmness based on a time-based sleep stage determination of a user.

FIG. 20 is a conceptual diagram of an example of adjusting mattress firmness based on a time-based sleep stage determination of a user. As depicted, the user can be sleeping in a bed system 2000 (e.g., refer to the bed system 1900 in FIG. 19). The bed system 2000 can be in data communication (e.g., wired, wireless) with a controller 2002 (e.g., refer to the controller 1902 in FIG. 19). The controller 2002 can be configured to determine adjustments to the bed system 2000 based on a sleep schedule (e.g., refer to the process 2200 in FIG. 22). In other words, rather than determining a current sleep state of the user based on sensed data about the user in the bed system 2000, the controller 2002 can identify how long the user is in the bed system 2000 and correlate such lengths of time with the sleep schedule to determine appropriate adjustments to make to the bed system 2000.

The sleep schedule can indicate projected amounts of time that a user would be in different sleep stages during a sleep session. The projected amounts of time per sleep stage can be determined from a time of sleep onset. The sleep schedule can be determined based on historic sleep information about the particular user in FIG. 20. For example, sleep tracking analysis can be performed to determine amounts of time that the particular user spends in each sleep stage during a typical sleep session. In some implementations, the sleep schedule can be determined based on a general population or specific matching-population of users sleep history.

The bed system 2000 can sense sleep onset of the user (A). The bed system 2000 can therefore keep track of when the user falls asleep. The bed system 2000 can also keep track of when the user exits the bed system 2000 and/or when the user wakes up. As described herein, the bed system 2000 can include a plurality of sensors (e.g., a sensor system) configured to detect pressure, temperature, and other indicators of the user when the user lays on top of a mattress of the bed system 2000. In some implementations, the sensors can be part of wearable devices (e.g., smart watch, heart rate monitor, smart clothes, etc.) and/or mobile phones or home automation devices that are in data communication with the controller 2002. Any one or more of the sensors described herein can capture sleep onset information (e.g., data) about the user. The sleep onset information can include changes in heartrate, respiration rate, motion level, and/or breathing patterns. For example, a decrease in heartrate, respiration rate, and/or breathing patterns can indicate that the user has fallen asleep. The sleep onset information can also include an indication of how much time it took the user to fall asleep and/or a time at which the user fell asleep. The sleep onset information can then be transmitted to the controller 2002 (B).

The controller 2002 can also receive the sleep schedule (C). For example, the controller 2002 can access a database or data store (e.g., cloud service) and retrieve the sleep schedule. The controller 2002 can retrieve a user-specific sleep schedule or a generic sleep schedule, as mentioned above. In some implementations, the controller 2002 can determine whether to use the user-specific or the generic sleep schedule. For example, if a user-specific sleep schedule has not been generated for the particular user (e.g., the user is a new user, the user does not yet have a user profile associated with the bed system 2000, the user is a temporary user of the bed system 2000, etc.), then the controller 2002 can select or receive the generic sleep schedule.

The controller 2002 can determine bed adjustments based on the sleep onset data and the sleep schedule (D). For example, the controller 2002 can determine from the sleep onset data that the user's heartrate lowered to a value indicative of sleep onset. The controller 2002 can assume that for a first 30 minutes from sleep onset, the user is within one phase or sleep stage in which mattress firmness can remain constant (e.g., at a user-defined or user-preferred firmness setting). The controller 2002 can also determine that after the first 30 minutes, if the user is still in the bed, then the user has entered another phase of sleep according to the sleep schedule. Mattress firmness adjustments can be determined based on the user entering this other phase of sleep (e.g., increase pressure in the mattress to compensate for absence of muscle tone from the user's body during a deeper sleep, such as REM). In comparison to the sleep state approach described in FIG. 19, here the controller 2002 can track a time from which the user fell asleep to determine bed adjustments that align with different sleep stages in the sleep schedule. Other aspects of the sleep environment can be changed instead of or in addition to bed firmness. For example, sound can be played prior to the transition to shallow sleep to protect sleep. In another example, a change in ambient temperature to raise the temperature above, e.g., 18C, may be initiated.

The controller 2002 can transmit the bed adjustment(s) to the bed system 2000 (E). The bed system 2000 can then adjust the bed according to the information received from the controller 2002. After adjustments are made to the bed system 2000, a presence of the user can be checked (G). In other words, the bed system 2000 can determine whether the user is still in the bed, whether the user is awake, how much time has passed since the user fell asleep, and/or how much time has passed since the user presence was last checked. The bed system 2000 can collect presence data or other sensed data about the user (e.g., pressure changes in one or more components of the bed system 2000). The bed system 2000 can transmit the presence data to the controller 2002 (H). The controller 2002 can determine whether the user is still in the bed. If the user is still in the bed, then the controller 2002 can determine bed adjustment(s) based on the sleep schedule (D).

Items (D)-(H) in FIG. 20 can be repeated until the controller 2002 determines one or more conditions. The one or more conditions can include that (1) the user is no longer in the bed, (2) the user is a predetermined amount of time away from waking up to an alarm, (3) the user is awake, (4) the user woke up from the alarm, indicating end of a sleep session, and/or (5) an amount of time has passed that does not indicate a change in sleep stage according to the sleep schedule. For example, the controller 2002 can determine that the user is between 30 to 60 minutes from a desired wakeup alarm time. According to the sleep schedule, this timeframe can be a time at which mattress firmness can be returned to the user-defined or user-preferred firmness setting. Once the mattress is returned to this firmness setting, the controller 2002 can determine that no more adjustments can be made to the bed system 2000 until the alarm goes off, thereby ending the sleep session.

Figure 21:
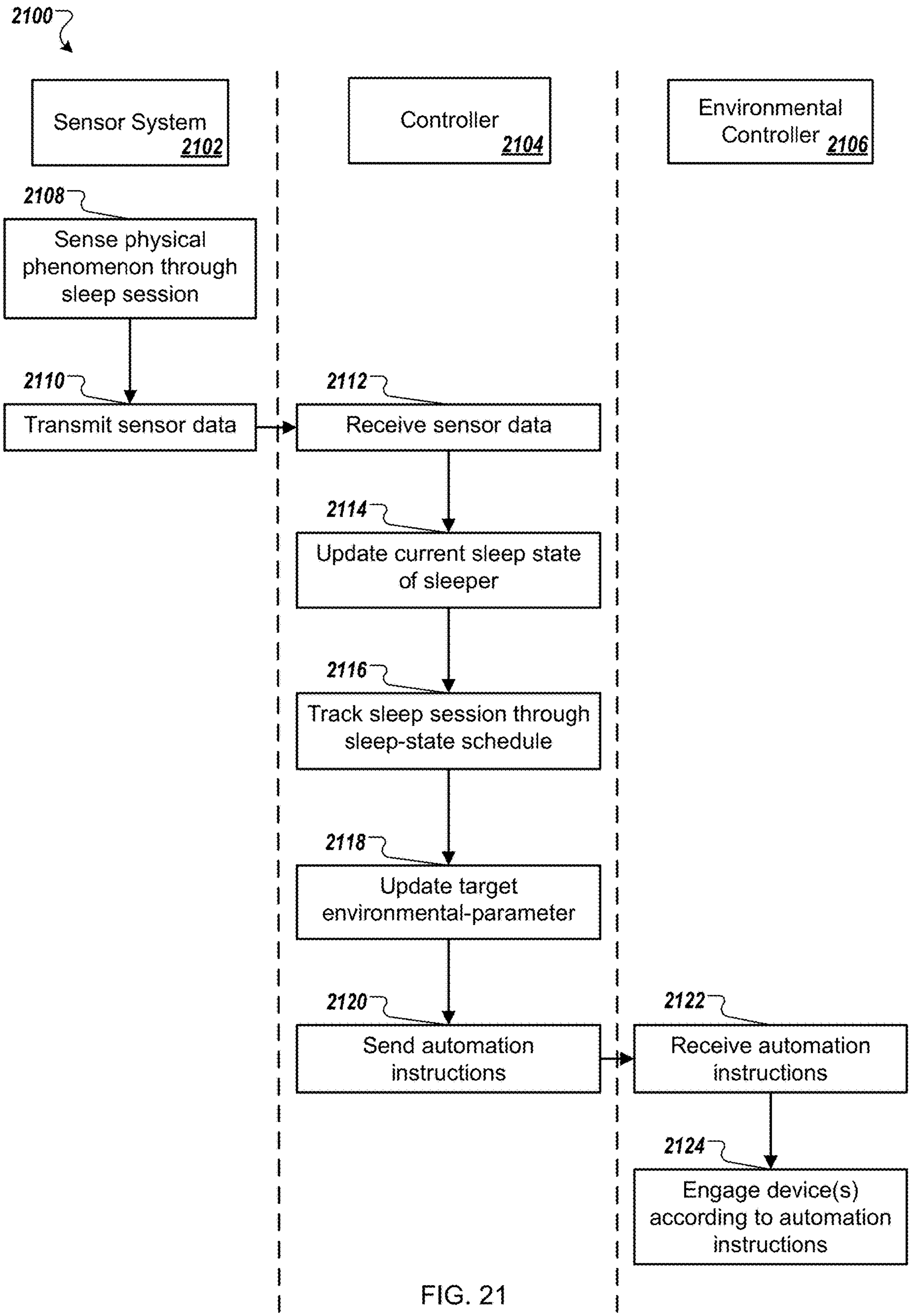
FIG. 21 is a swimlane diagram of an example process for adjusting mattress firmness based on a current sleep state of a user.

FIG. 21 is a swimlane diagram of an example process 2100 for adjusting mattress firmness based on a current sleep state of a user (e.g., refer to FIG. 19). For illustrative purposes, the process 2100 is described with reference to a sensor system 2102, a controller 2104, and an environmental controller 2106. The sensor system 2102 can include one or more sensors (e.g., pressure, temperature, etc.) that are configured or otherwise attached to a bed system. The sensor system 2102 can also include any one or more sensors that are part of a wearable device and/or a mobile device of the user that is in data communication with one or more of the bed system, the controller 2104, and the environmental controller 2106.

The controller 2104 can be configured to control one or more operations of the bed system, such as determining when to make adjustments to different components of the bed system. The controller 2104 can be any one or more of the controllers described throughout this disclosure. In some implementations, the controller 2104 can be integrated, attached, or otherwise in communication with the bed system. In some implementations, the controller 2104 can be a home automation device, a remote server (e.g., cloud service), or a mobile device that performs processing techniques. The controller 2104 can also be any other type of computing system that is in data communication with the sensor system 2102.

Moreover, the environmental controller 2106 can be configured to control one or more components of the bed system, based on instructions received from the controller 2104. The environmental controller 2106 can, for example, execute instructions that cause air chambers of a mattress of the bed system to inflate (e.g., to increase mattress firmness) and/or deflate (e.g., to decrease mattress firmness). The environmental controller 2106 can execute instructions that cause pressure to increase and/or decrease in the mattress.

The environmental controller 2106 can also, for example, adjust an incline or decline of an adjustable foundation, environmental lights, lights under the bed system, and/or peripheral devices in communication with the controller 2106. The environmental controller 2106 can be any one or more of the controllers described throughout this disclosure. In some implementations, the environmental controller 2106 can be the same as the controller 2104. In some implementations, the environmental controller 2106 can be integrated, attached, or otherwise in communication with the bed system. In some implementations, the environmental controller 2106 can also be a home automation device, a remote server, or a mobile device that performs processing techniques. The environmental controller 2106 can also be any other type of computing system that is in data communication with the sensor system 2102 and/or the controller 2104.

Any one or more of the sensor system 2102, the controller 2104, and the environmental controller 2106 can be components of the data processing system 400 and/or the bed systems described throughout this disclosure. Other system or systems can also be used to perform the same or a similar process.

Referring to the process 2100, the process 2100 can begin, for example, when the sensor system 2102 senses physical phenomenon through a sleep session of the user in 2108. The sensor system 2102 can sense at least one physical phenomenon. A sleep session can occur whenever the user lays in bed and tries to fall asleep. The sleep session can be short, such as a nap. The sleep session can also be longer, such as when the user goes to bed at the end of the day. For many users, a sleep session can occur overnight. For some users, a sleep session can occur during the day, especially if the user has work or other responsibilities overnight. The sleep session can end once the user wakes up and/or exits the bed. In some implementations, the user can experience multiple sleep sessions in one night or period of time. In other words, every time the user wakes up, a new sleep session can start once the user falls back asleep. In other implementations, the sleep session can continue even when sleep is temporarily interrupted (e.g., the user wakes up and falls back asleep). In some cases, various sleep sessions through the day (e.g., naps) may be monitored and accounted for in other calculations.

The sleep session can begin when presence of the user is initially identified in the bed. The sleep session can also begin when sleep onset is identified after user presence in the bed is detected. The sleep session can last until sleep is no longer identified for a threshold period of time. For example, the user can wake up multiple times during sleep but then go back to sleep. The sleep session can persist through those momentary wake ups so long as those momentary wake ups are shorter than a threshold period of time. On the other hand, if the user experiences momentary wake ups that exceed the threshold period of time, then the sleep session can end. If the user returns to sleep, a new sleep session can begin.

The sleep session can also last until presence of the user is identified as missing for a threshold period of time. For example, the sleep session can end if the user gets out of bed to drink water and does not come back to bed until after the threshold period of time ends. Moreover, the sleep session can last until an alarm is scheduled and/or goes off. The alarm can come from a mobile device, such as a cellphone, and/or an alarm clock. The mobile device and/or the alarm clock can be in data communication with at least one of the sensor system 2102 and the controller 2104. The scheduled alarm can therefore be communicated to the sensor system 2102 and/or the controller 2104.

Still referring to 2108, the sensor system 2102 can sense physical phenomenon such as changes in heartrate, respiration rate, breathing rate, bodily movements, pressure changes in the bed system, temperature, snores, and/or other acoustic sounds. Different values can be sensed by the sensor system 2102 and combined to determine information about the user, such as the user's current sleep state. The sensor system 2102 can sense the physical phenomenon continuously throughout the sleep session of the user. The physical phenomenon can also be sensed periodically, for example, every minute. Continuous and/or periodic sensing can be beneficial to detect user changes as they occur. These user changes can indicate that the user is changing sleep states. Therefore, dynamic adjustments to the bed system can be made in real-time, as the user changes or enters different sleep states. In some implementations, the physical phenomenon can be sensed when computational resources of the sensor system 2102 and/or the controller 2104 are not otherwise being utilized.

The sensor system 2102 can then transmit sensor data to the controller 2104 based on the sensed physical phenomenon through the sleep session (2110). In some implementations, the sensor system 2102 can combine different physical phenomenon into the sensor data such that the sensor data can be used to determine a current sleep state of the user. The controller 2104 can receive, through the sleep session, the sensor data (2112). The controller 2104 can also receive the plurality of different sensed physical phenomenon and then combine or associate such physical phenomenon with each other.

The controller 2104 can then update, through the sleep session, a current sleep state of the user in 2114. The controller 2104 can update the current sleep state of the user based on the sensor data.

The user can experience several different sleep states throughout the sleep session. Each of the sleep states can require different adjustments to be made to the bed system. The current sleep state, for example, can indicate what type of adjustments can be made to the bed in order to provide the user with optimized sleep quality and comfortability in that current sleep state. As an example, the controller 2104 can determine that the user's current sleep state is being awake. The controller 2104 can receive sensor data (2112) of a heartrate that is lower than a heartrate of the user when the user is awake. The controller 2104 can determine that the heartrate is below a predetermined threshold range, which indicates that the user has fallen asleep. Therefore, the controller 2104 can update the current sleep state of the user from being awake to having just fallen asleep. The controller 2104 can then determine appropriate bed system adjustments that correspond to the current sleep state of having just fallen asleep.

The controller 2104 can track the sleep session through a sleep-state schedule in 2116. This tracking can be based on the update of the current sleep state of the user through the sleep session. In some implementations, the controller 2104 can check or verify the current sleep state against the sleep-state schedule to determine whether the controller's determination of the current sleep state is accurate. The sleep-state schedule can indicate projected times at which the user remains within different sleep states. The sleep-state schedule can also indicate projected conditions (e.g., heartrate, movement, respiration rate, etc.) that the user can be expected to experience in each of the different sleep states. The sleep-state schedule can also list different successive phases that the user experiences during the sleep session.

The sleep-state schedule can be defined using successive phases. Each phase can specify (i) one or more values for the current sleep state and (ii) one or more values for a target environmental-parameter associated with the current sleep state. The target environmental-parameter can be the mattress firmness. Thus, the sleep-state schedule can indicate what firmness settings can be applied in different sleep states (e.g., phases) that the user may or will experience. The successive phases can include an initial sleep phase, a middle sleep phase, and a near-wakeup phase. The successive phases can include one or more additional or fewer phases.

In some implementations, the initial sleep phase can specify (i) an NREM sleep state for less than a threshold time period and (ii) a user-specified pressure setting. Therefore, when the user is identified to be in the initial sleep phase, the controller 1902 can determine that the mattress firmness may remain at the user-specified pressure setting and/or be set to the user-specified pressure setting. During the initial sleep phase, the user may be in a light sleep and/or may otherwise have muscle tone. Therefore, adjustments to the mattress firmness may not be required to accommodate for changes in the user's body based on the sleep stage. Moreover, in some implementations, the threshold time period can be 30 minutes. The 30 minutes can be calculated from a time of sleep onset.

The middle sleep phase can specify (i) an NREM sleep state for greater than the threshold time period and (ii) an increased pressure setting that is greater than the user-specified pressure setting. The increased pressure setting can be calculated at a time at which firmness of the mattress should be increased. Calculating the pressure setting can be advantageous to allow for dynamic generation of the increased pressure setting based on changes in user-defined or user-preferred firmness settings. User-defined or user-preferred settings can change often when the user goes through rapid physiological change, such as pregnancy or recovery from injuries. The increased pressure setting can also be predetermined ahead of time and stored in memory. Predetermining this setting can be advantageous to use less processing power and resources in real-time. The predetermined setting can include increasing the pressure by 10% from (i) the user-defined or user-preferred setting or (ii) a pressure setting of the mattress in the sleep phase before the middle sleep phase.

The user can enter the middle sleep phase approximately 30 to 60 minutes after sleep onset. During the middle sleep phase, the user can enter a deeper sleep and can lose or otherwise lack muscle tone. To compensate for the lack of muscle tone and to improve or otherwise maintain sleep quality and comfortability, the controller 2104 can determine that the mattress firmness should be increased. Increasing mattress firmness can therefore improve spinal alignment and ensure that the user continues to be comfortable during the middle sleep phase of the sleep session.

The near-wakeup sleep phase can specify (i) an REM sleep less than a threshold period of time near a scheduled wake-up time and (ii) the user-specified pressure setting. The threshold period of time can be 30 to 60 minutes before the scheduled wake-up time. In some implementations, the user-specified pressure setting can be the same as the increased pressure setting or other pressure settings that are stored in memory or otherwise associated with a profile of the user. The user-specified pressure setting can be a same value as the increased pressure setting or other pressure settings in order to conserve processing resources and memory. Therefore, as an example, when the user is detected to be within 30 to 60 minutes from the wakeup alarm, the controller 2104 can determine that the mattress firmness should be reset or adjusted to the user-specified pressure setting that the mattress was initially set to when the user was falling asleep.

In some implementations, the user-specified pressure setting can be a different value. In other words, two values can be stored in memory and both can be the same value. However, in such an example, the user can change the user-specified value that is stored in memory. The user can desire to change the value based on, for example, the user finding that a softer bed helps them fall asleep but that a firmer bed in the morning eases their joint pains. Therefore, the user-specified pressure setting for the near-wakeup sleep phase can be different than the initial user-specified pressure setting. As an example, the mattress can initially be set to a pressure setting that is less firm. When the controller 2104 determines that the user is within 30 to 60 minutes from the wakeup alarm, the controller 2104 can determine that the mattress firmness should be adjusted to a different user-specified pressure setting that requires the mattress to be firmer than the initial pressure setting. In some implementations, the different user-specified pressure setting can be the same as a current pressure setting of the mattress, which means that the controller 2104 would not have to determine an adjustment for the mattress. In other implementations, the different user-specified pressure setting can be less than or greater than the current pressure setting of the mattress, which means that the controller 2104 can determine how much to adjust the mattress by to achieve the different user-specified pressure setting.

Still referring to 2116 in the process 2100, tracking the sleep session through the sleep-state schedule can include maintaining identification of the current sleep state as a first phase of the successive phases, determining that the current sleep state matches the one or more values for the current sleep state specified by a second phase, and updating the identification of the current sleep state to a second phase that is successive to the first phase in the successive phases. Therefore, the controller 2104 can update the current sleep state of the user based on values that are defined for different successive sleep phases in the sleep-state schedule.

The controller 2104 can then update, through the sleep session, a target environmental-parameter in 2118. As described herein, the target environmental-parameter can be mattress firmness. The controller 2104 can update the target environmental-parameter based on using the tracking of the sleep session. As the controller 2104 tracks that the user enters different successive sleep phases, the controller 2104 can determine corresponding adjustments to the mattress firmness.

For example, the controller 2104 can determine that the user has entered a sleep stage in which the user's muscle tone is absent. To provide the user with optimal sleep quality and comfort as well as spinal alignment, the controller 2104 can determine that the mattress firmness can be increased. Thus, the controller 2104 can update the target mattress firmness parameter to an increase pressure setting.

As another example, the controller 2104 can determine that the user is 30 minutes away from waking up to an alarm. The controller 2104 can therefore determine that the mattress firmness should be reset to a user-defined or user-preferred firmness setting. The controller 2104 can update the target mattress firmness parameter to an initial value (e.g., the user-defined or user-preferred setting) before the user began the sleep session (e.g., sleep onset).

Updating the target environmental-parameter in 2118 can also include generating instructions that, when executed, cause one or more components of the bed system to make the adjustments to the target environmental-parameter.

In 2120, the controller 2104 can send automation instructions to the environmental controller 2106. The instructions can indicate adjustments to make to the target environmental-parameter (e.g., increase pressure within air chambers of the mattress, decrease pressure within air chambers of the mattress, etc.). The instructions can also indicate which components can be activated to execute the adjustments to the target environmental-parameter (e.g., a pump). The environmental controller 2106 can receive the automation instructions in 2122.

The environmental controller 2106 can then engage one or more devices according to the automation instructions (2124). By engaging the devices, the sleep environment of the user can be updated through the sleep session. Engaging the devices can include actuating a pump to inject additional air (e.g., pressure) into air chambers of the mattress, thereby increasing firmness of the mattress. Engaging the devices can also include opening valves or otherwise actuating the pump to release air or pressure from the air chambers of the mattress, thereby decreasing firmness of the mattress.

The process 2100 can be repeated and continuously performed for as long as the user is within the sleep session. The process 2100 can also be repeated and continuously performed for each sleep session of the user.

Figure 22:
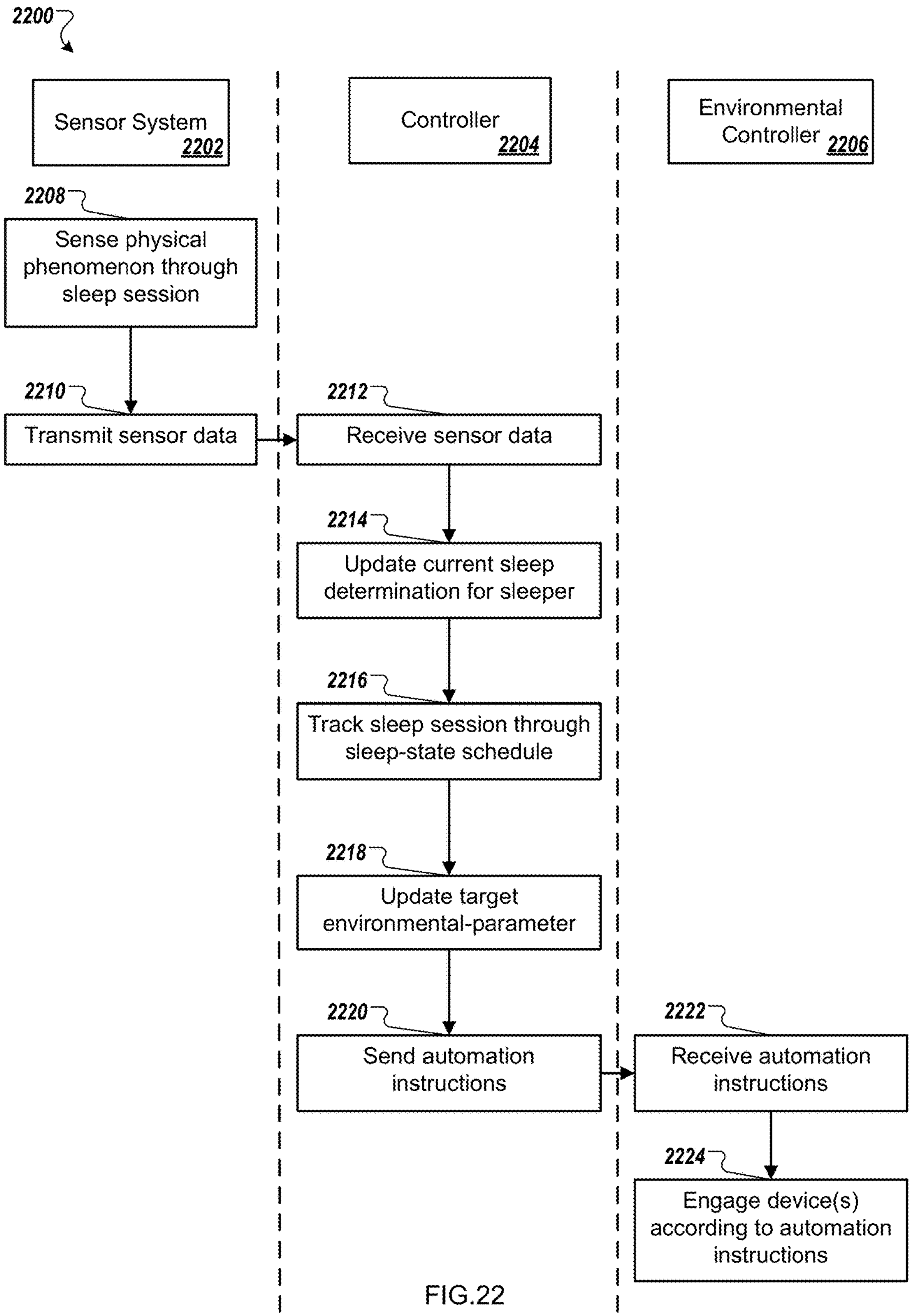
FIG. 22 is a swimlane diagram of an example process for adjusting mattress firmness based on a time-based sleep state determination of a user.

FIG. 22 is a swimlane diagram of an example process 2200 for adjusting mattress firmness based on a time-based sleep state determination of a user (e.g., refer to FIG. 20). For illustrative purposes, the process 2200 is described with reference to a sensor system 2202, a controller 2204, and an environmental controller 2206 (e.g., refer to the sensor system 2102, the controller 2104, and the environmental controller 2106 in FIG. 21). Any one or more of the sensor system 2202, the controller 2204, and the environmental controller 2206 can be components of the data processing system 400 and/or the bed systems described throughout this disclosure. Other system or systems can also be used to perform the same or a similar process.

Referring to the process 2200, the process 2200 can begin, for example, when the sensor system 2202 senses at least one physical phenomenon through a sleep session of the user in 2208 (e.g., refer to 2108 in FIG. 21). The sensor system 2202 can then transmit sensor data to the controller 2204 based on the sensed physical phenomenon through the sleep session in 2210 (e.g., refer to 2110 in FIG. 21). The controller 2204 can receive, through the sleep session, the sensor data in 2212.

The controller 2204 can update, through the sleep session, a current sleep determination for the user (2214). The controller 2204 can update the current sleep determination using the sensor data. The current sleep determination can include possible values of awake and asleep. The sensor data, for example, can include a decrease in heartrate or breathing pattern, which can be indicative that the user has fallen asleep. The controller 2204 can therefore update the current sleep determination to indicate that the user is currently asleep. At this point in the process 2200, the controller 2204 may not determine what sleep stage the user is currently in. Rather, the controller 2204 may only determine that the user is asleep rather than awake.

Until the controller 2204 receives sensor data indicating that the user may be sleeping (e.g., lower heartrate and/or respiration rate), the current sleep determination of the user can have a value of awake. Once the controller 2204 receives data indicating that the user may be sleeping, the current sleep determination can be updated to a value of asleep. In some implementations, the controller 2204 can also determine a time at which the current sleep determination value is changed from awake to asleep.

Next, the controller 2204 can track the sleep session through a sleep-state schedule in 2216. The sleep schedule can be defined using successive phases, as described in reference to FIG. 21. Each phase can specify (i) one or more values for the current sleep determination and (ii) one or more values for a target environmental-parameter. The successive phases can include (i) an initial sleep phase, (ii) a middle sleep phase, and (iii) a near-wakeup phase. As described in reference to FIG. 21, one or more additional or fewer successive phases can be identified.

In some implementations, the initial sleep phase can specify (i) an NREM sleep state for less than a threshold time period and (ii) a user-specified pressure setting. The middle sleep phase can specify (i) an NREM sleep state for greater than the threshold time period and (ii) an increased pressure setting that is greater than the user-specified pressure setting. The near-wakeup sleep phase can specify (i) an REM sleep less than a threshold period of time near a scheduled wake-up time and (ii) the user-specified pressure setting (e.g., refer to 2116 in FIG. 21).

As an example, once the controller 2204 updates the current sleep determination value from awake to asleep, the controller 2204 can determine how much time passes. If, for example, the controller 2204 determines that 30 to 60 minutes have passed since sleep onset, the controller 2204 can determine that the user has likely entered the middle phase. Thus, the controller 2204 can determine that the mattress firmness (e.g., the target environmental-parameter) can be increased by a predetermined amount. If, for example, the controller 2204 determines that the user is 30 to 60 minutes away from an alarm, then the controller 2204 can identify that the user is likely in the near-wakeup sleep phase. Consequently, the controller 2204 can determine that the mattress firmness can be reset or otherwise adjusted to the user-specified pressure setting.

Still referring to 2216 in the process 2200, tracking the sleep session can include maintaining identification of the current sleep determination as a first phase of the successive phases, determining that the current sleep determination matches the one or more values for the current sleep determination specified by a second phase, and updating the identification of the current sleep determination to a second phase that is successive to the first phase in the successive phases.

Tracking the sleep session can be based on a length of time that has elapsed since the current sleep determination was updated to asleep. For example as described above, bed adjustments may not be made while the user is awake. Rather, adjustments can be taken into consideration only once the user experiences sleep onset.

The controller 2204 can then update, through the sleep session and using the tracking of the sleep session, a target environmental-parameter (2218). As described in reference to FIG. 21, the target environmental-parameter can be mattress firmness of the bed system. Updating the target environmental-parameter can include determining that mattress pressure setting can be increased or decreased based on timing of the sleep session matching a value in the sleep-state schedule that is indicative of a particular sleep stage.

The controller 2204 can also send automation instructions, through the sleep session, to the environmental controller 2206 (2220). The instructions can be based on the update of the target environmental-parameter (e.g., refer to 2120 in FIG. 21). The environmental controller 2206 can receive the automation instructions in 2222. The environmental controller 2206 can then engage one or more devices according to the automation instructions (2224). By engaging the one or more devices, the sleep environment of the user can be updated through the sleep session (e.g., refer to 2124 in FIG. 21).

The process 2200 can be repeated and continuously performed for as long as the user is within the sleep session. The process 2200 can also be repeated and continuously performed for each sleep session of the user.

Figure 23:
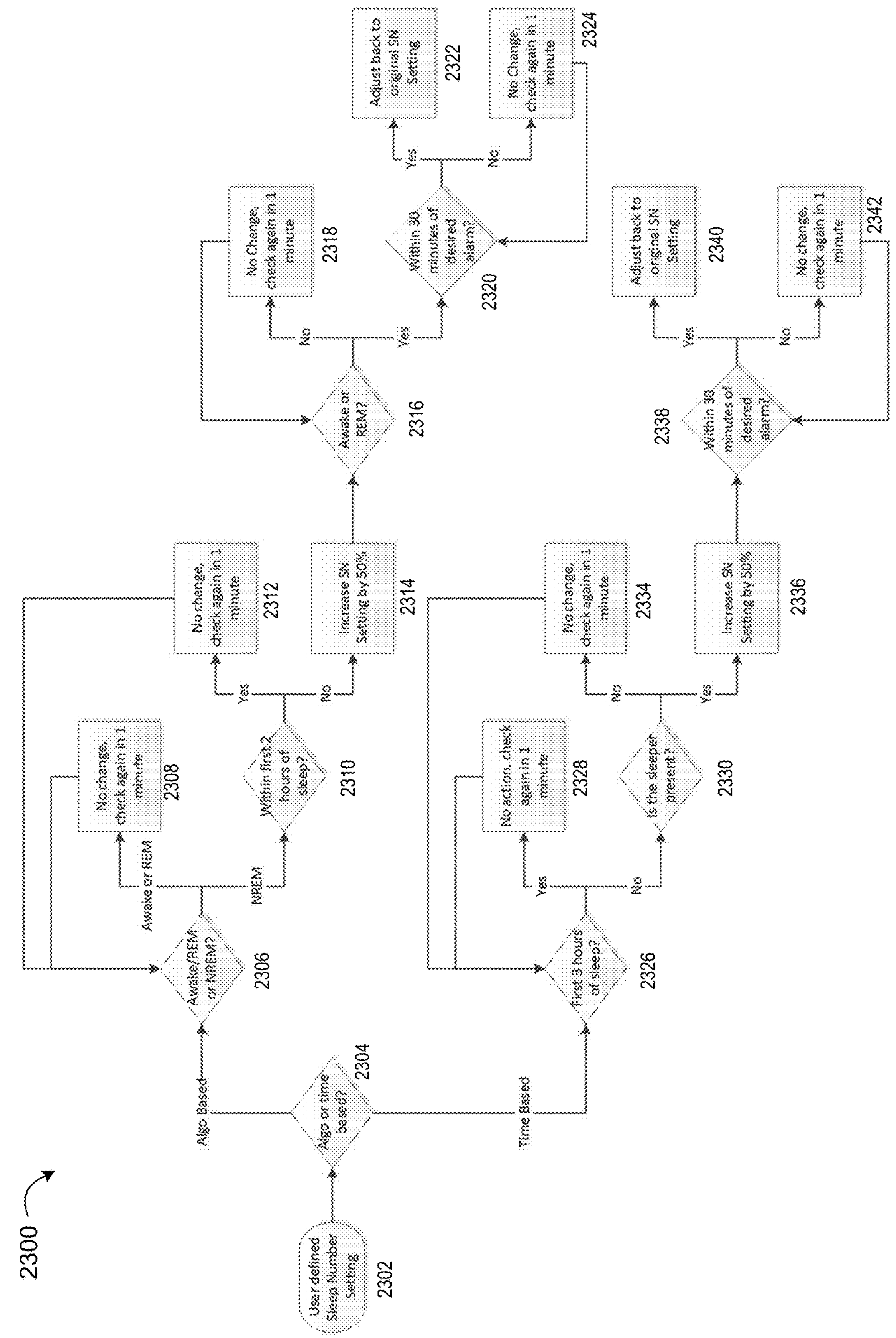
FIG. 23 is a flowchart of an example process for adjusting mattress firmness during different sleep stages of a user.

FIG. 23 is a flowchart of an example process 2300 for adjusting mattress firmness during different sleep stages of a user. As described throughout this disclosure and depicted in FIG. 23, adjusting mattress firmness can be based on a sleep monitoring, state-based algorithm (e.g., refer to the process 2100 in FIG. 21) or a time-based algorithm (e.g., refer to the process 2200 in FIG. 22). The sleep monitoring state-based algorithm can be used to determine which sleep state (e.g., sleep stage, sleep phase) the user is currently in to then determine appropriate mattress adjustments. The time-based algorithm can be used to determine mattress adjustments based on a time of sleep onset and guidelines associated with different sleep stages.

As described herein, the mattress can have a relatively low pressure setting during early sleep onset. Firmness of the mattress can increase (e.g., increase pressure setting of the mattress) during NREM sleep stages to target improved spinal alignment, body support, and overall comfortability and sleep quality. Firmness of the mattress can decrease (e.g., decrease pressure setting of the mattress) during REM sleep stages, at initial sleep onset, and/or within a time period before wakeup to provide continuous spinal alignment, body support, and overall comfortability and sleep quality.

The process 2300 can be performed as either sleep monitoring state-based or time-based. In some implementations, the user can select whether mattress firmness adjustments are determined based on the state-based algorithm or the time-based algorithm. In some implementations, the process 2300 can offer either the state-based algorithm or the time-based algorithm. In yet other implementations, a controller can determine whether to perform the process 2300 using the state-based algorithm or the time-based algorithm.

For clarity, the process 2300 is being described with reference to a controller, such as one of the components of the data processing system 400. The controller can any one of the controllers described herein (e.g., refer to FIGS. 19-22). However, other system or systems can be used to perform the same or a similar process.

Referring to the process 2300 depicted in FIG. 23, a user-defined sleep setting (e.g., sleep number) can be provided to a controller (2302). The sleep setting can indicate a preferred firmness level for the mattress. The sleep setting can also indicate one or more additional preferred firmness levels for different stages of the user's sleep. In some implementations, the sleep setting can be determined by one or more systems as described herein. The sleep setting can be determined based on historic data about the user. The sleep setting can also be determined based on data associated with a general population of users.

Next, the controller can determine whether to determine firmness adjustments based on the sleep state-based algorithm or the time-based algorithm, as described above (2304). In some implementations, the controller can determine that the controller may or may not be receiving sensor signals from one or more components of the bed. Thus, the controller can select the state-based algorithm.

When the sleep state-based algorithm is selected, the controller can determine whether the user is awake, in REM sleep, or in NREM sleep (2306). If the user is awake or in REM sleep, the controller can determine that no change should be made to the mattress firmness (2308). The controller can also check the sleep state of the user again after a length of time (e.g., 30 seconds) has passed. In some implementations, the time interval can be different. The controller can return to 2306.

If the user is in NREM sleep, then the controller can determine whether the user is in a first 2 hours of sleep (2310). If the user is within the first 2 hours of sleep, the controller can determine that no change should be made to the mattress firmness (2312). The controller can also check the sleep state of the user again after 1 minute has passed. The controller can return to 2306. If the user is not within the first 2 hours of sleep, the controller can increase the mattress firmness setting by 10% (2314). In other words, the controller can increase a pressure level of air chambers within the mattress by 10% from the user-defined sleep setting. As a result, the mattress can become more firm to accommodate for changes in the user's body during deeper sleep stages.

Once the mattress firmness setting is increased by 10%, the controller can determine whether the user is awake or in REM sleep (2316). If the user is neither awake nor in REM sleep, the controller can determine that no change should be made to the mattress firmness (2318). The controller can also check the sleep state of the user again after 1 minute has passed. The controller can return to 2316.

If the user is either awake or in REM sleep, the controller can determine whether the user is within 30 minutes of a desired alarm (2320). If the user is within 30 minutes of the desired alarm, the controller can adjust the mattress firmness setting back to the original user-defined sleep setting (2322). If the user is not within 30 minutes of the desired alarm, the controller can determine that no change should be made to the mattress firmness (2324). The controller can also check again in 1 minute whether the user is within 30 minutes of the desired alarm. The controller can return to 2320.

Still referring to the process 2300, when the time-based algorithm is selected in 2304 (or otherwise when the controller is only presented with the option of using the time-based algorithm), the controller can determine whether the user is in a first 3 hours of sleep (2326).

If the user is within the first 3 hours of sleep, the controller can determine that no change should be made to the mattress firmness (2328). The controller can check again in 1 minute whether the user is within the first 3 hours of sleep. The controller can then return to 2326.

If the user is not within the first 3 hours of sleep, the controller can determine whether the user is present in the bed (2330). In other words, the controller can determine whether the user is occupying the bed or whether the user is out of the bed. The controller can make such a determination based on received, sensed pressure values from pressure sensors or other sensors of the bed. The controller can compare pressure values that were previously received with current pressure values to determine whether a change in pressure indicates that the user is currently present in the bed.

If the sleeper is not present in the bed, the controller can determine that no change should be made to the mattress firmness (2334). The controller can check again in 1 minute whether the user is within the first 3 hours of sleep. The controller can then return to 2326.

If the sleeper is present in the bed, the controller can increase the mattress firmness setting by 10% (2336). In other words, the controller can increase a pressure level of air chambers within the mattress by 10% from the user-defined sleep setting.

Next, the controller can determine whether the user is within 30 minutes of a desired alarm (2338). If the user is within 30 minutes of the desired alarm, the controller can adjust the mattress firmness setting back to the original, user-defined sleep setting (2340). If the user is not within 30 minutes of the desired alarm, the controller can determine that no change should be made to the mattress firmness (2342). The controller can check again in 1 minute whether the user is within 30 minutes of the desired alarm. The controller can then return to 2338. The process 2300 can be repeated for as long as the user is within a sleep session.

Figure 24:
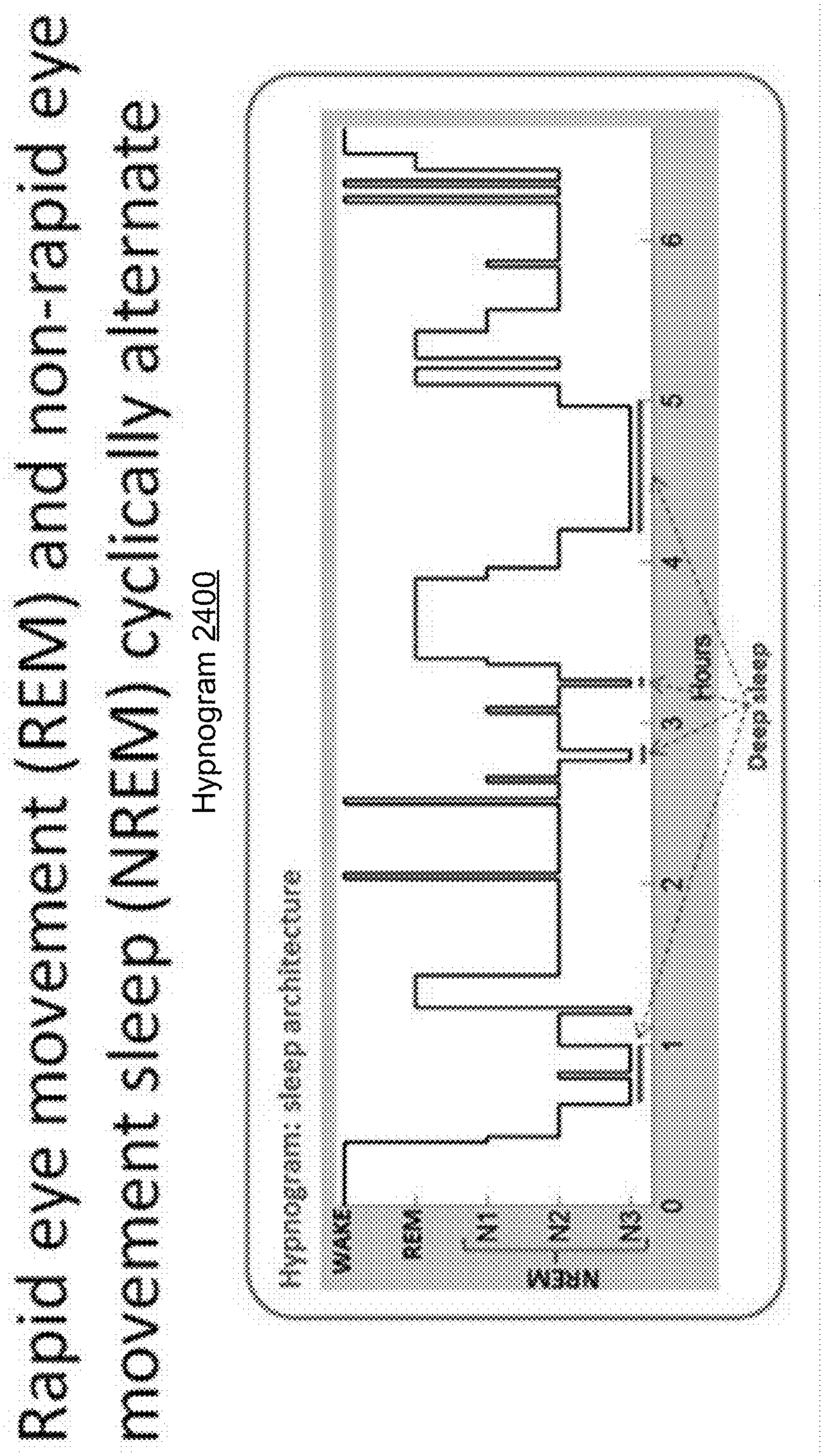
FIG. 24 is a hypnogram depicting timing at which a user is in different sleep stages.

FIG. 24 is a hypnogram 2400 depicting timing at which a user is in different sleep stages. The hypnogram 2400 depicts rapid eye movement (REM) and non-rapid eye movement (NREM) as they cyclically alternate while the user sleeps. As shown, the user can experience deep sleep, N3, at time intervals such as 40 minutes into sleep, 15 minutes before 3 hours of sleep, 15 minutes after 3 hours of sleep, and between 4 to 5 hours of sleep. Moreover, as depicted, REM sleep occurs typically in a second half of the user's sleep, between 3 to 4 hours after sleep onset.

Mattress firmness can be modulated according to these timings. As described above, mattress firmness can be increased when the user is in NREM, deep sleep states and mattress firmness can be decreased when the user is in REM sleep states. During the deep sleep states, the user may lack muscle tone and otherwise may experience lower comfortability in a less firm, softer mattress. During lighter sleep states, the user may have muscle tone and otherwise may experience greater or constant comfortability in a less firm, softer mattress.

Figure 25:
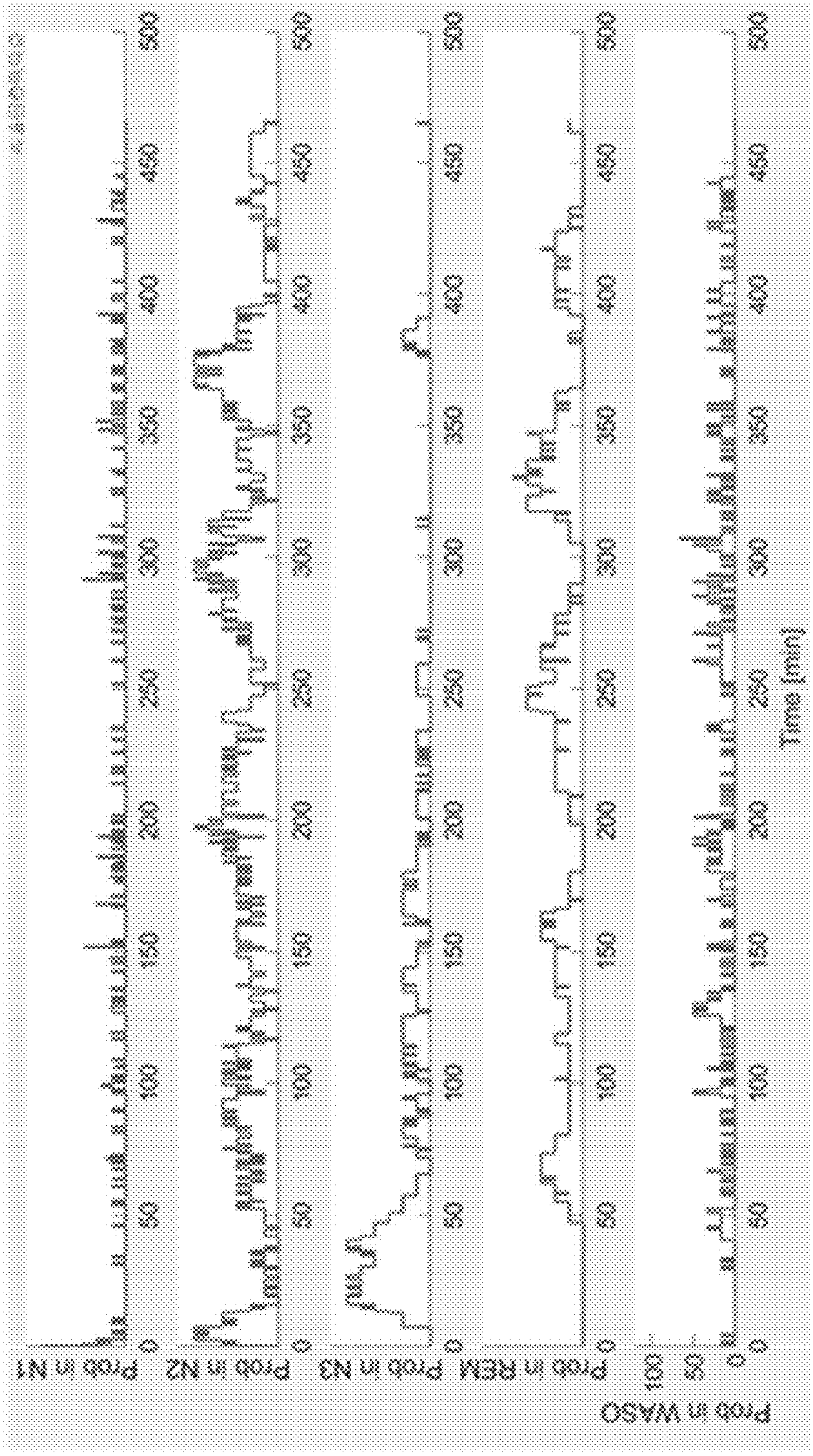
FIG. 25 is a graph depicting time-dependent sleep stage probabilities.

FIG. 25 is a graph 2500 depicting time-dependent sleep stage probabilities. These time-dependent sleep stage probabilities can be empirically obtained for a specific user or at a population level using demographic segments. These sleep stage probabilities can be used in a time-based algorithm or approach to determining bed adjustments (e.g., refer to FIGS. 20, 22, and 23). As shown in the graph 2500, deep sleep is most probable 30 minutes after sleep onset. Thus, adjustments to the mattress firmness may not be made during a first 30 minutes of a user's sleep. Adjustments to the mattress firmness can be made during other time intervals when the user is most likely in deep sleep. As described herein, mattress firmness can be increased when it is determined that the user has been asleep in different sleep stages for predetermined amounts of time.

What is claimed is:

1. A system comprising:

a bed having a mattress configured to support a sleeper in a sleep environment;

a sensor system configured to:

sense at least one physical phenomenon through a sleep session;

transmit sensor data to a controller based on the sensed physical phenomenon through the sleep session; and the controller, wherein the controller comprises at least one processor and memory, the controller configured to:

receive, through the sleep session, the sensor data;

select, from a plurality of algorithms, a selected algorithm based on at least one of the sensor data, user input, and checking a clock, wherein the algorithms include (i) a state-based algorithm and (ii) a schedule-based algorithm;

update, through the sleep session, using the selected algorithm, a current sleep state of the sleeper;

track the sleep session based on the update of the current sleep state of the sleeper through the sleep session;

update, through the sleep session, using the tracking of the sleep session, a target environmental-parameter;

send, through the sleep session, automation instructions to an environmental controller based on the update of the target environmental-parameter;

update, through the sleep session, using the sensor data, a current sleeping determination for the sleeper, the sleeping determination having possible values of awake and asleep; and track the sleep session through a sleep state-time based schedule based on a length of time that has elapsed since the current sleeping determination was updated to asleep;

wherein the sleep state-time based schedule comprises data stored to memory defining a sequence, and an order of the sequence, of phases, each phase specifying i) one or more values for the current sleeping determination; and ii) one or more values for the target environmental-parameter.

2. The system of claim 1, further comprising the environmental controller configured to:

receive the automation instructions from the controller; and engage one or more devices according to the automation instructions in a manner that the sleep environment of the sleeper is updated through the sleep session.

3. The system of claim 2, wherein the mattress includes at least one air chamber, wherein engaging the one or more devices according to the automation instructions include engaging a pump to increase pressure to the at least one air chamber of the mattress in a manner that a firmness of the mattress is increased.

4. The system of claim 3, wherein engaging the one or more devices according to the automation instructions includes engaging the pump to decrease pressure to the at least one air chamber of the mattress in a manner that the firmness of the mattress is decreased.

5. The system of claim 1, wherein the target environmental-parameter is a firmness of the mattress.

6. The system of claim 1, wherein the at least one physical phenomenon includes a heartrate, a respiration rate, a breathing rate, snoring, bodily movement of the sleeper, a determination that the sleeper has fallen asleep, a duration of time that has passed since sleep onset, a pressure change in the mattress, a temperature of the sleeper, and a temperature of a top surface of the mattress.

7. The system of claim 1, wherein the selected algorithm is the state-based algorithm, wherein the controller is configured to:

update, through the sleep session, using the sensor data, the current sleep state of the sleeper; and track the sleep session through a sleep-state schedule based on the update of the current sleep state of the sleeper through the sleep session.

8. The system of claim 7, wherein the sleep-state schedule is defined using successive phases, each phase specifying i) one or more values for the current sleep state; and ii) one or more values for the target environmental-parameter.

9. The system of claim 8, wherein tracking the sleep session through the sleep-state schedule based on the update of the current sleep state of the sleeper through the sleep session comprises:

maintaining identification of the current sleep state as a first phase of the successive phases;

determining that the current sleep state matches the one or more values for the current sleep state specified by a second phase; and updating the identification of the current sleep state to a second phase that is successive to the first phase in the successive phases.

10. The system of claim 8, wherein the successive phases comprise i) an initial sleep phase, ii) a middle sleep phase, and iii) a near-wakeup phase.

11. The system of claim 10, wherein the initial sleep phase is at least thirty minutes after the sleeper has entered the bed.

12. The system of claim 10, wherein the near-wakeup phase is between thirty and forty minutes before an alarm set by the sleeper.

13. The system of claim 10, wherein:

the initial sleep phase specifies i) an NREM sleep state for less than a threshold time period; and ii) a user-specified pressure setting;

the middle sleep phase specifies i) an NREM sleep state for greater than the threshold time period; and ii) an increased pressure setting that is greater than the user-specified pressure setting; and the near-wakeup sleep phase specifies i) an REM sleep less than a threshold period of time near a scheduled wake-up time; and ii) the user-specified pressure setting.

14. The system of claim 1, wherein tracking the sleep session through the sleep state-time based schedule based on the length of time that has elapsed since the current sleeping determination was updated to asleep comprises:

maintaining identification of the current sleeping determination as a first phase of the successive phases;

determining that the current sleeping determination matches the one or more values for the current sleeping determination specified by a second phase; and updating the identification of the current sleeping determination to the second phase that is successive to the first phase in the successive phases.

15. The system of claim 1, wherein the controller is at least one of a home automation device, a mobile device, and a remote server that is in data communication with the sensor system and the environmental controller.

16. The system of claim 1, wherein the controller includes the environmental controller.

17. A system comprising:

a bed having a mattress configured to support a sleeper in a sleep environment;

a sensor system configured to:

sense at least one physical phenomenon through a sleep session;

transmit sensor data to a controller based on the sensed physical phenomenon through the sleep session;

the controller, wherein the controller comprises at least one processor and memory, the controller configured to:

receive, through the sleep session, the sensor data;

update, through the sleep session, using the sensor data, a current sleep state of the sleeper;

track the sleep session through a sleep-state schedule based on the update of the current sleep state of the sleeper through the sleep session, wherein the sleep state schedule comprises data stored to memory defining a sequence, and an order of the sequence, of phases, each phase specifying i) one or more values for the current sleeping determination; and ii) one or more values for the target environmental-parameter;

update, through the sleep session, using the tracking of the sleep session, a target environmental-parameter; and send, through the sleep session, automation instructions to an environmental controller based on the update of the target environmental-parameter; and the environmental controller configured to:

receive the automation instructions; and engage one or more devices according to the automation instructions in a manner that the sleep environment of the sleeper is updated through the sleep session.

18. A system comprising:

a bed having a mattress configured to support a sleeper in a sleep environment;

a sensor system configured to:

sense at least one physical phenomenon through a sleep session;

transmit sensor data to a controller based on the sensed physical phenomenon through the sleep session;

the controller, wherein the controller comprises at least one processor and memory, the controller configured to:

receive, through the sleep session, the sensor data;

update, through the sleep session, using the sensor data, a current sleeping determination for the sleeper, the sleeping determination having possible values of awake and asleep;

track the sleep session through a sleep-state schedule based on a length of time that has elapsed since the current sleeping determination was updated to asleep, wherein the sleep state schedule comprises data stored to memory defining a sequence, and an order of the sequence, of phases, each phase specifying i) one or more values for the current sleeping determination; and ii) one or more values for the target environmental-parameter;

update, through the sleep session, using the tracking of the sleep session, a target environmental-parameter; and send, through the sleep session, automation instructions to an environmental controller based on the update of the target environmental-parameter; and the environmental controller configured to:

receive the automation instructions; and engage one or more devices according to the automation instructions in a manner that the sleep environment of the sleeper is updated through the sleep session.

* * * * *